(12) United States Patent
Lee et al.

(10) Patent No.: US 10,787,448 B2
(45) Date of Patent: Sep. 29, 2020

(54) INDOLIZINO [3,2-C] QUINOLINE-BASED FLUORESCENT PROBE

(71) Applicants: SEOUL NATIONAL UNIVERSITY R & DB FOUNDATION, Seoul (KR); INDUSTRY-ACADEMIC COOPERATION FOUNDATION YONSEI UNIVERSITY, Seoul (KR)

(72) Inventors: Jeeyeon Lee, Seoul (KR); Ikyon Kim, Seoul (KR); Soonbum Kwon, Seoul (KR); Bumhee Lim, Seoul (KR)

(73) Assignees: SEOUL NATIONAL UNIVERSITY R & DB FOUNDATION, Seoul (KR); INDUSTRY-ACADEMIC COOPERATION FOUNDATION YONSEI UNIVERSITY, Seoul (KR)

( * ) Notice: Subject to any disclaimer, the term of this patent is extended or adjusted under 35 U.S.C. 154(b) by 282 days.

(21) Appl. No.: 15/877,872

(22) Filed: Jan. 23, 2018

(65) Prior Publication Data
US 2018/0230144 A1    Aug. 16, 2018

Related U.S. Application Data

(63) Continuation-in-part of application No. PCT/KR2016/008059, filed on Jul. 22, 2016.

(30) Foreign Application Priority Data

Jul. 23, 2015 (KR) ........................ 10-2015-0104107
Jul. 21, 2016 (KR) ........................ 10-2016-0092867

(51) Int. Cl.
*C07D 471/04* (2006.01)
*C07D 487/04* (2006.01)
(Continued)

(52) U.S. Cl.
CPC ......... *C07D 471/04* (2013.01); *C07D 487/04* (2013.01); *C12Q 1/68* (2013.01);
(Continued)

(58) Field of Classification Search
CPC .... C07D 471/04; C07D 487/04; G01N 21/64; G01N 33/58; G01N 33/582;
(Continued)

(56) References Cited

U.S. PATENT DOCUMENTS

| 6,218,393 | B1 * | 4/2001 | Ryder ................. | C07D 401/12 514/249 |
| 8,420,647 | B2 * | 4/2013 | Bissantz ................ | A61P 1/04 514/249 |
| 9,296,751 | B1 * | 3/2016 | Kim ..................... | C07D 471/14 |
| 10,457,662 | B2 * | 10/2019 | Neamati ............ | A61K 31/5377 |

(Continued)

FOREIGN PATENT DOCUMENTS

| KR | 10-2016-0044750 A | 4/2016 |
| WO | 92/07856 A1 | 5/1992 |

OTHER PUBLICATIONS

Search notes from EIC 1700, conducted on Jan. 9, 2020 (Year: 2020).*

(Continued)

*Primary Examiner* — Lore R Jarrett
(74) *Attorney, Agent, or Firm* — Vorys, Sater, Seymour & Pease LLP; Mih Suhn Koh

(57) ABSTRACT

Provided is a fluorescent probe composition including an indolizino[3,2-c]quinoline-based compound, and a nucleic acid/protein/cell imaging method using the same. Since the compound of the present invention demonstrates excellent environmental sensitivity, fluorescence intensity, photostability, nucleic acid/protein binding, intracellular permeability, etc., the compound may be effectively used for various studies of protein/cell functions and imaging technologies, (Continued)

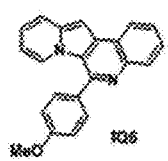 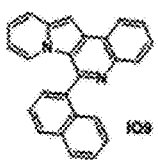 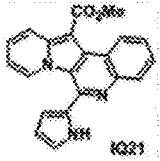

[FORMULA 2]    [FORMULA 3]    [FORMULA 4]

[FORMULA 5]    [FORMULA 6]

such as nucleic acid/protein kinetics, drug-protein interactions, and intracellular protein imaging.

13 Claims, 38 Drawing Sheets

Specification includes a Sequence Listing.

(51) Int. Cl.
 C12Q 1/68 (2018.01)
 G01N 21/64 (2006.01)
 G01N 33/58 (2006.01)
(52) U.S. Cl.
 CPC ............ *G01N 21/64* (2013.01); *G01N 33/58* (2013.01); *Y02A 50/58* (2018.01)
(58) Field of Classification Search
 CPC .. G01N 21/6486; G01N 21/6458; C12Q 1/68; C12Q 2563/107; C12Q 1/6876; Y02A 50/58
 See application file for complete search history.

(56) References Cited

U.S. PATENT DOCUMENTS

| | | | |
|---|---|---|---|
| 2004/0077674 A1* | 4/2004 | Curran | A61P 35/00 514/285 |
| 2005/0142162 A1* | 6/2005 | Hunter | A61N 1/05 424/423 |
| 2013/0252924 A1* | 9/2013 | Penninger | A61P 25/02 514/81 |
| 2015/0065436 A1* | 3/2015 | Arora | C07K 7/06 514/21.6 |

OTHER PUBLICATIONS

Peng et al., "Rhodium-catalyzed annulation between 2-arylimidazo[1,2-a]pyridines and alkynes leading to pyrido[1,2-a]benzimidazole derivatives", Org. Biomol. Chem., 2015, 13, 5354-5357.
Park et al., "When Indolizine Meets Quinoline: Diversity-Oriented Synthesis of New Polyheterocycles and Their Optical Properties", ACS Comb. Sci., 2015, 17, 459-469.
Frolov, "Effect of Methanesulfonyl Group on the Regioselectivity of Photocyclization of Arylheterylamine Derivatives", Russian Journal of General Chemistry, vol. 69, No. 8, pp. 1254-1261, (1999).

* cited by examiner

[FIG. 1]
[FORMULA 2] 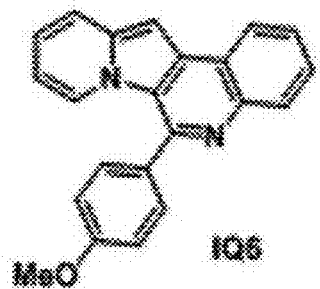
[FORMULA 3] 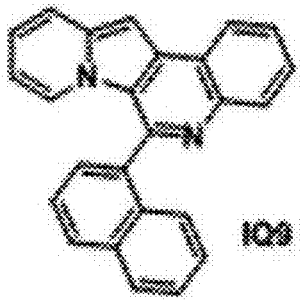
[FORMULA 4] 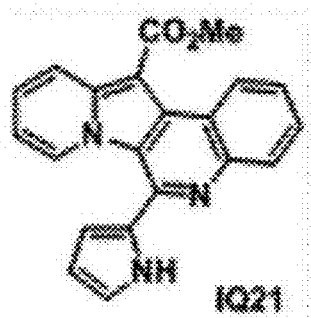
[FORMULA 5] 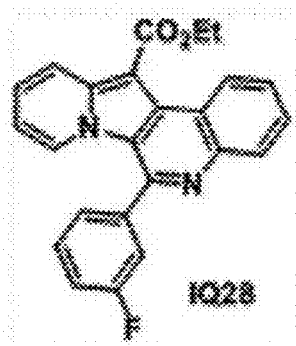
[FORMULA 6] 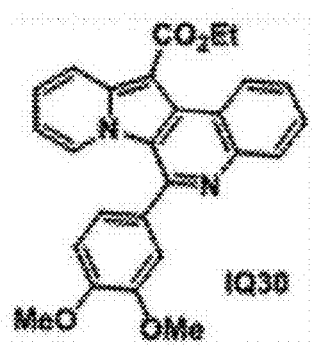

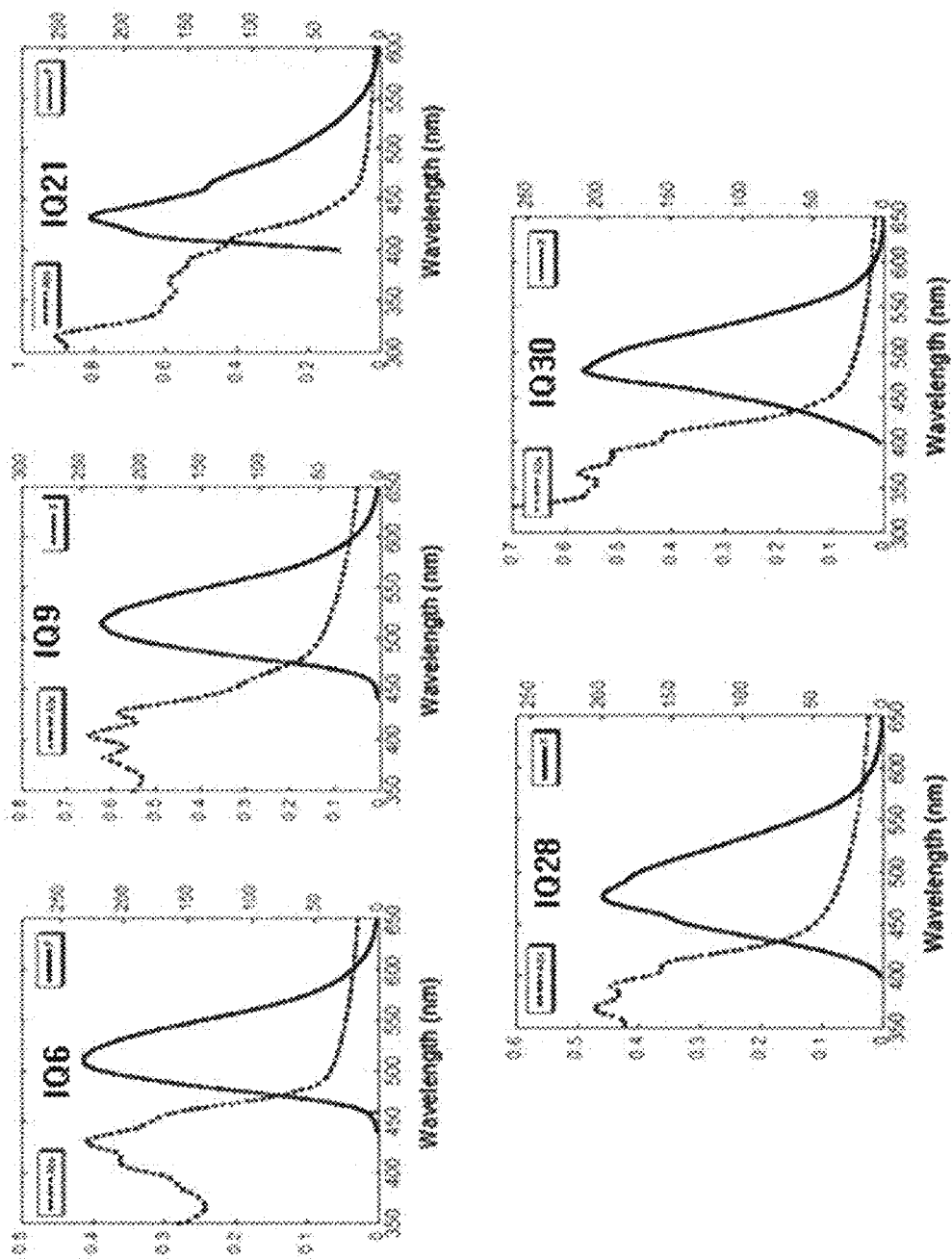
[FIG. 2]

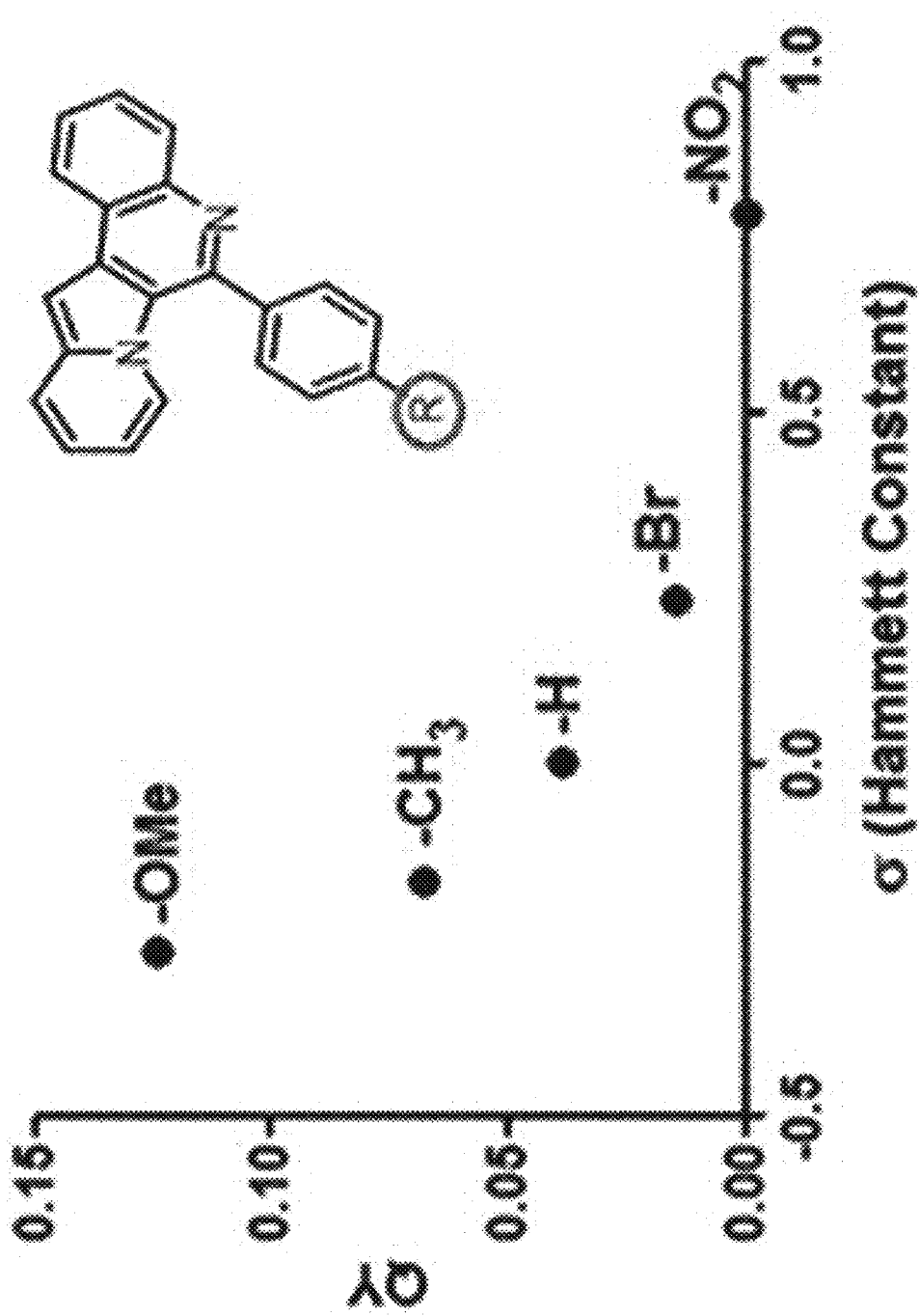
[FIG. 3]

[FIG. 4]
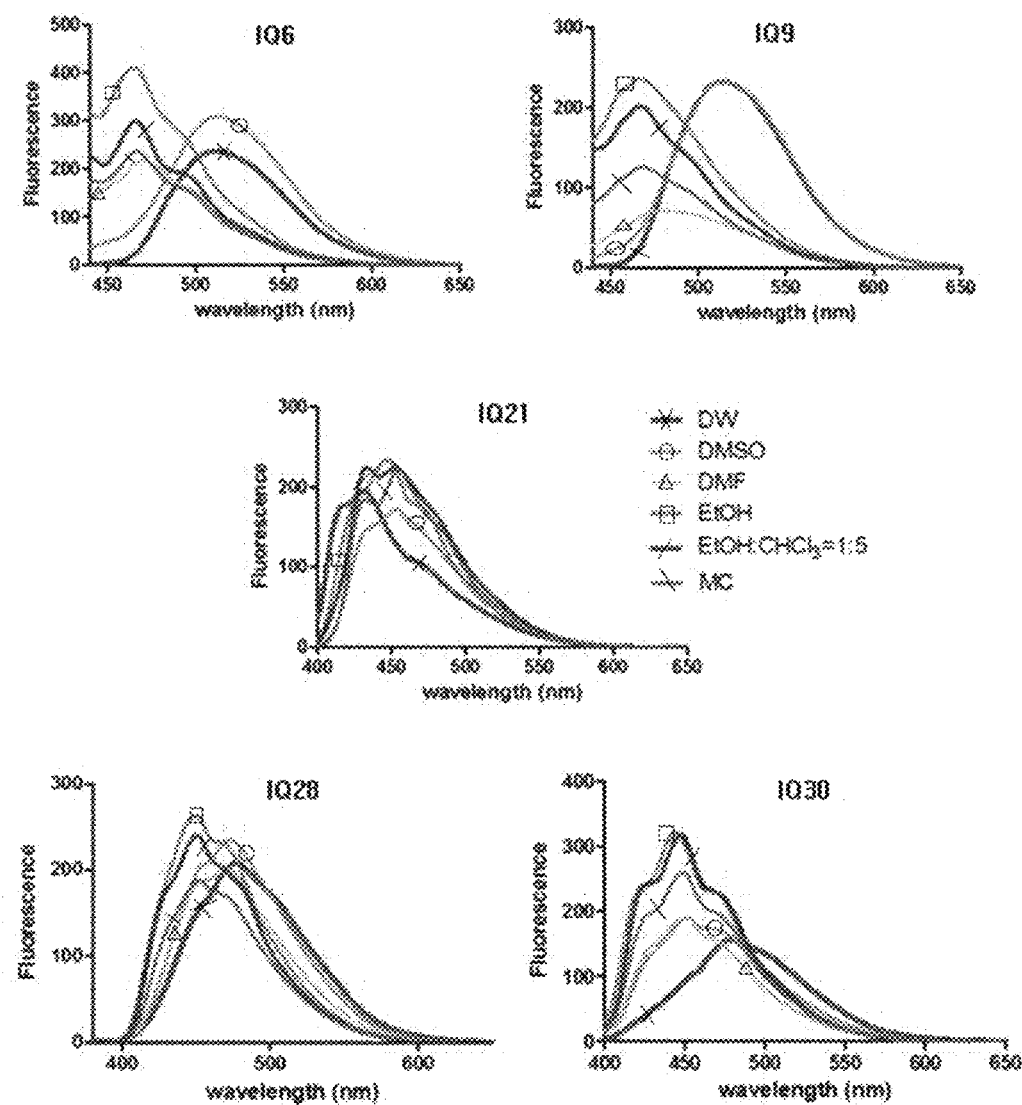

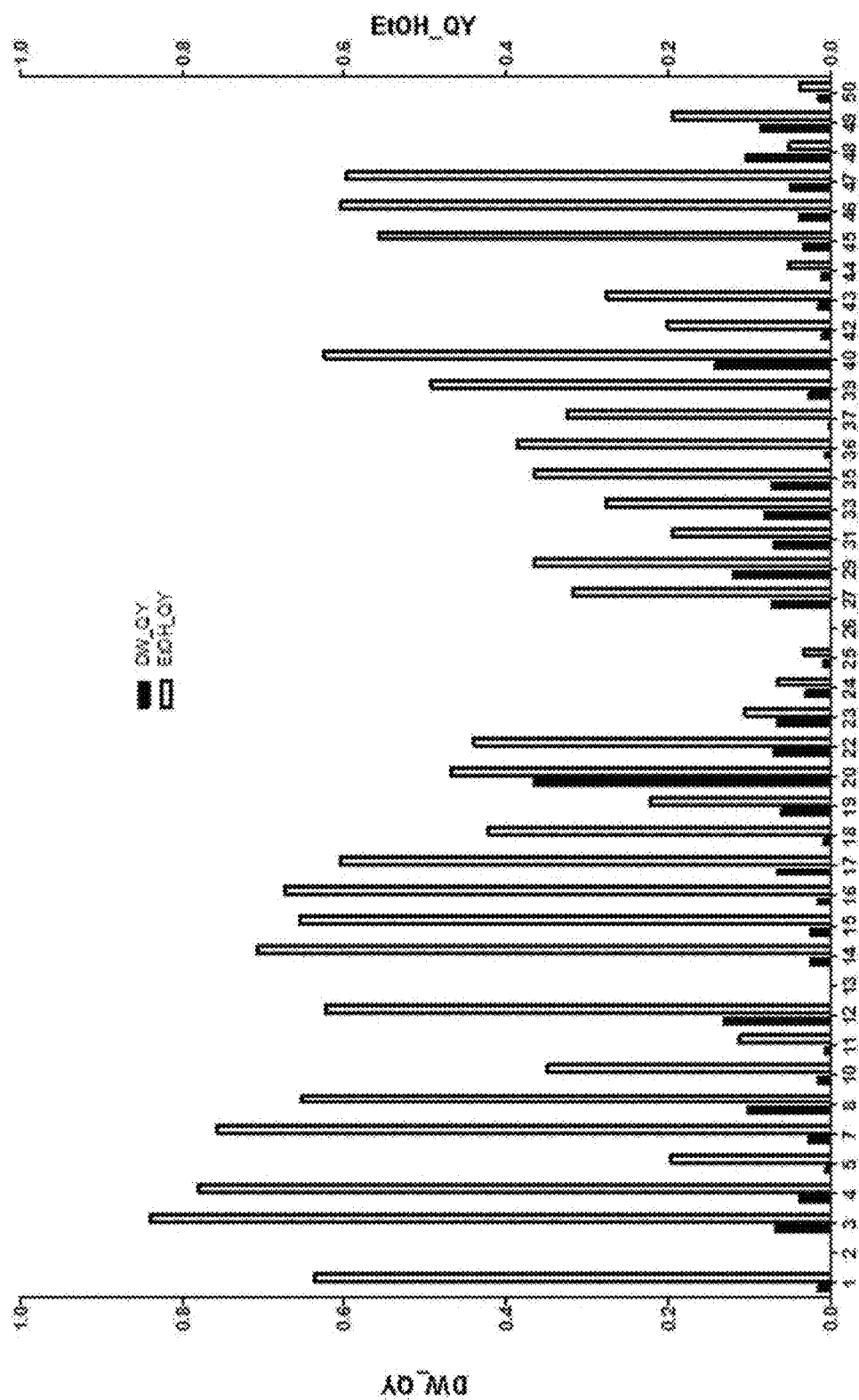
[FIG. 5a]

[FIG. 5b]
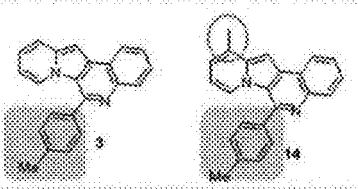

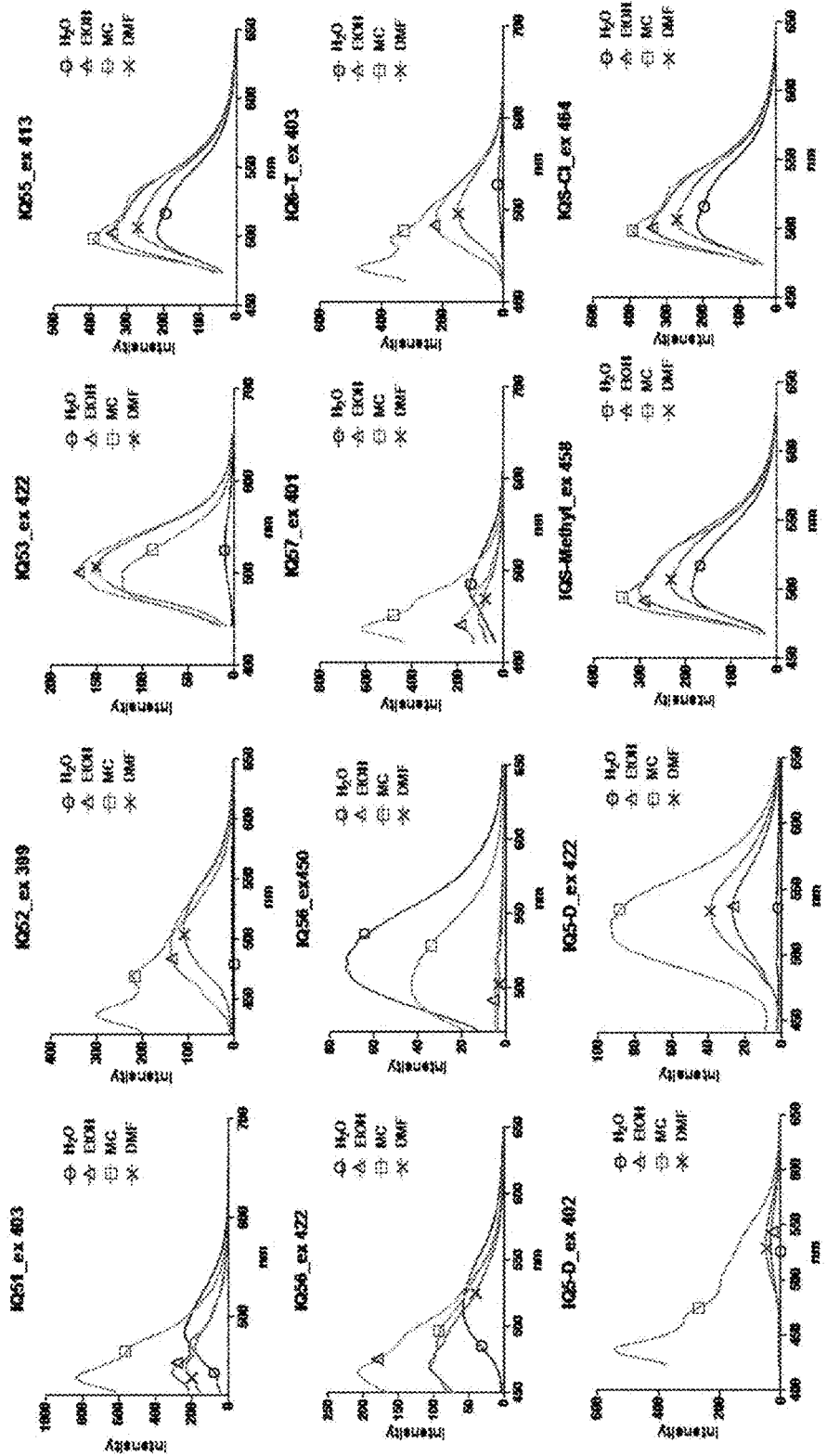
[FIG. 5c]

[FIG. 5d]
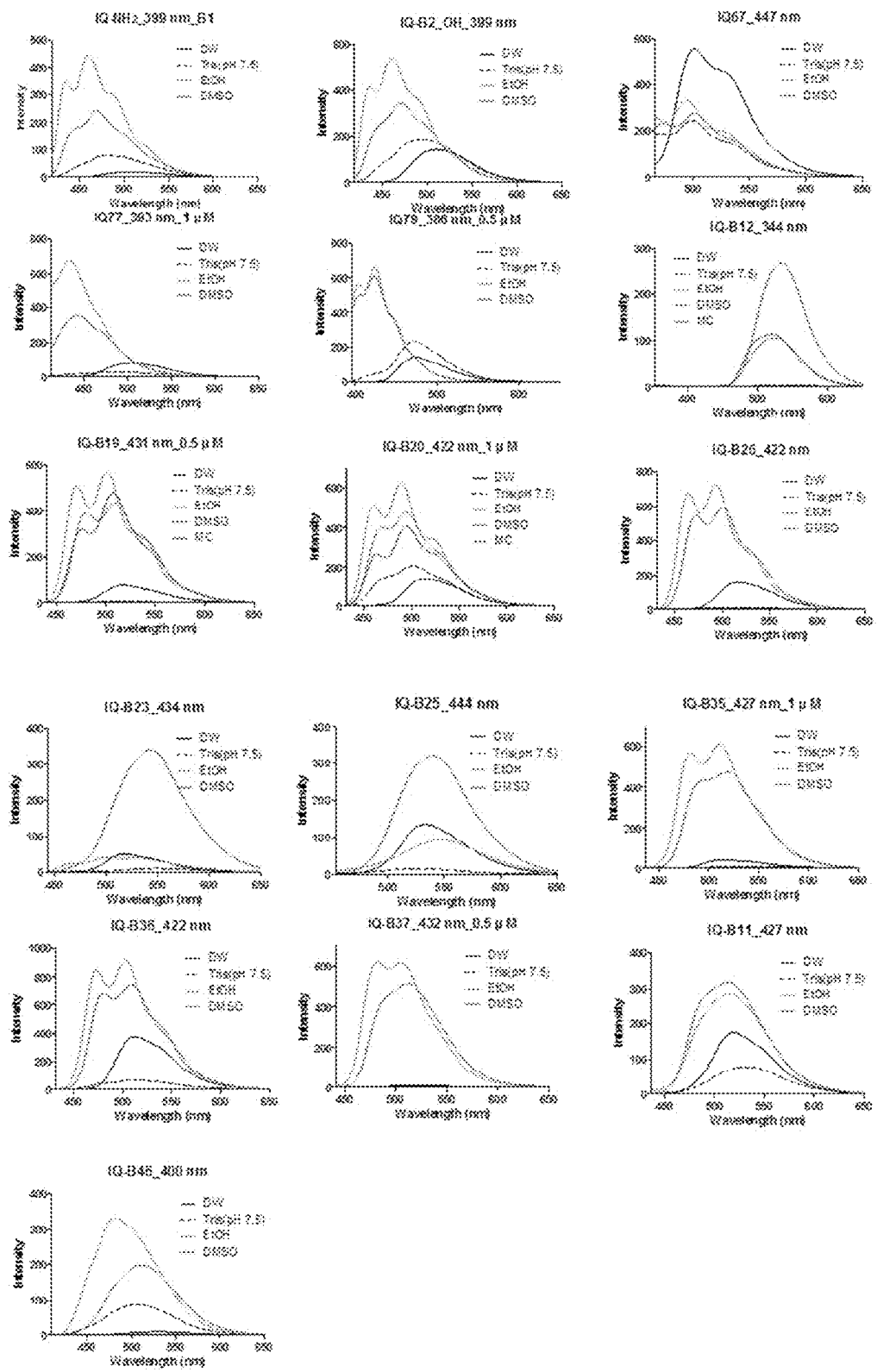

[FIG. 6]
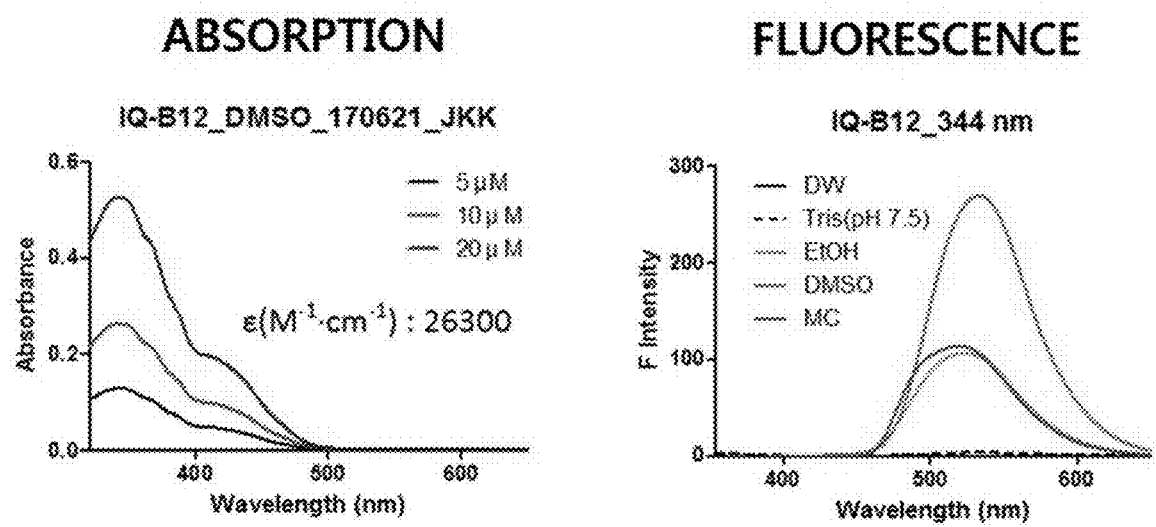

[FIG. 7a]
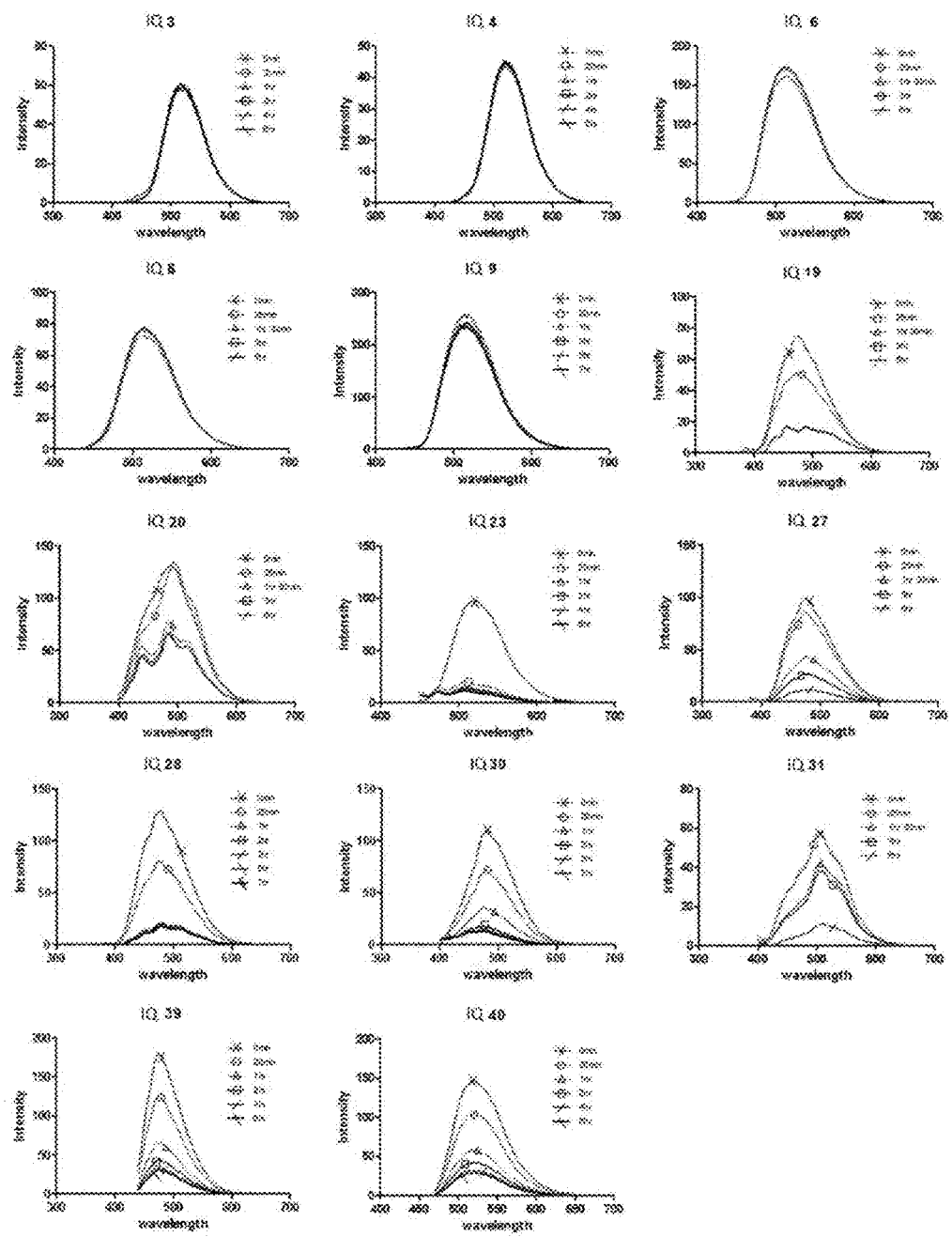

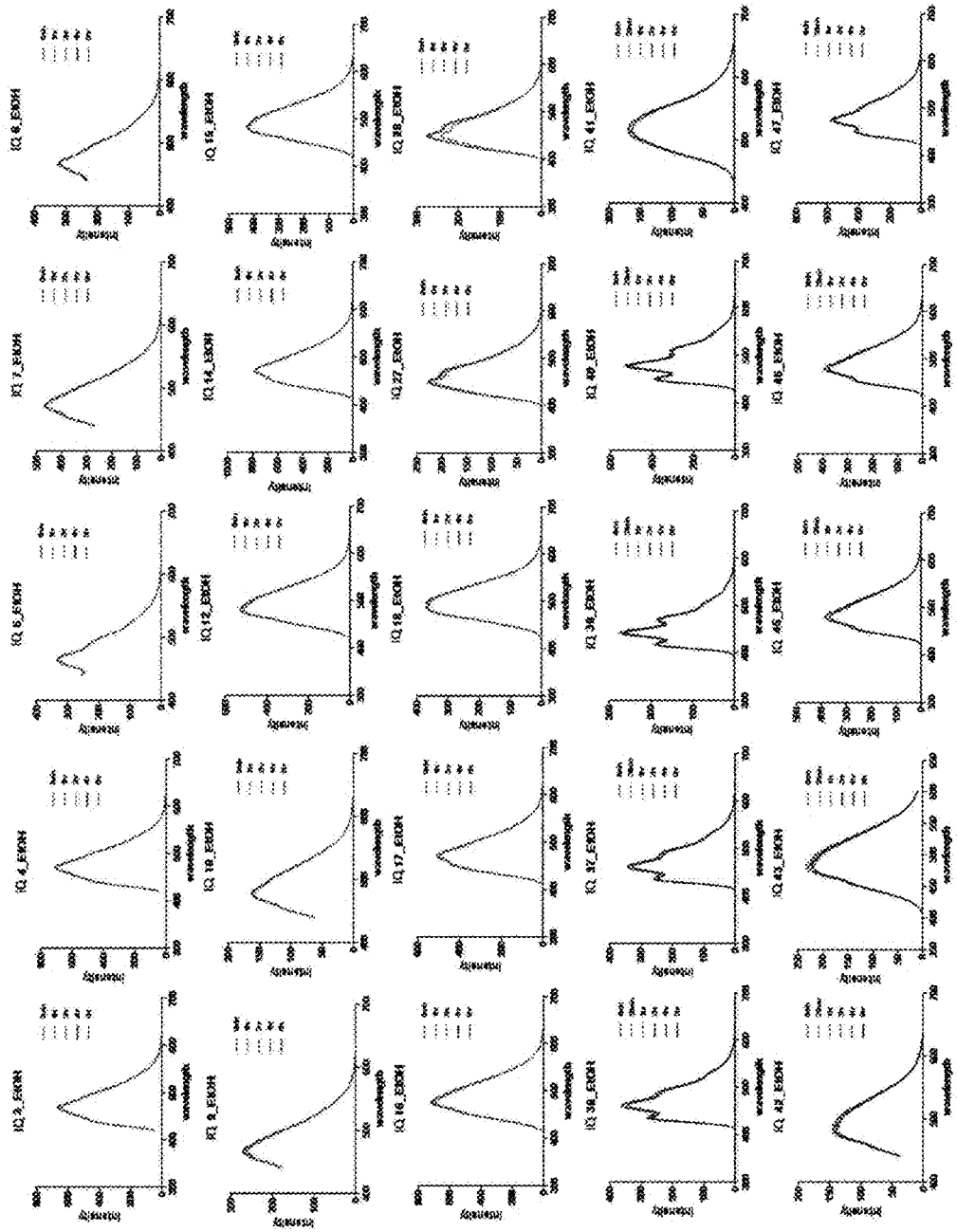
[FIG. 7b]

[FIG. 7c]
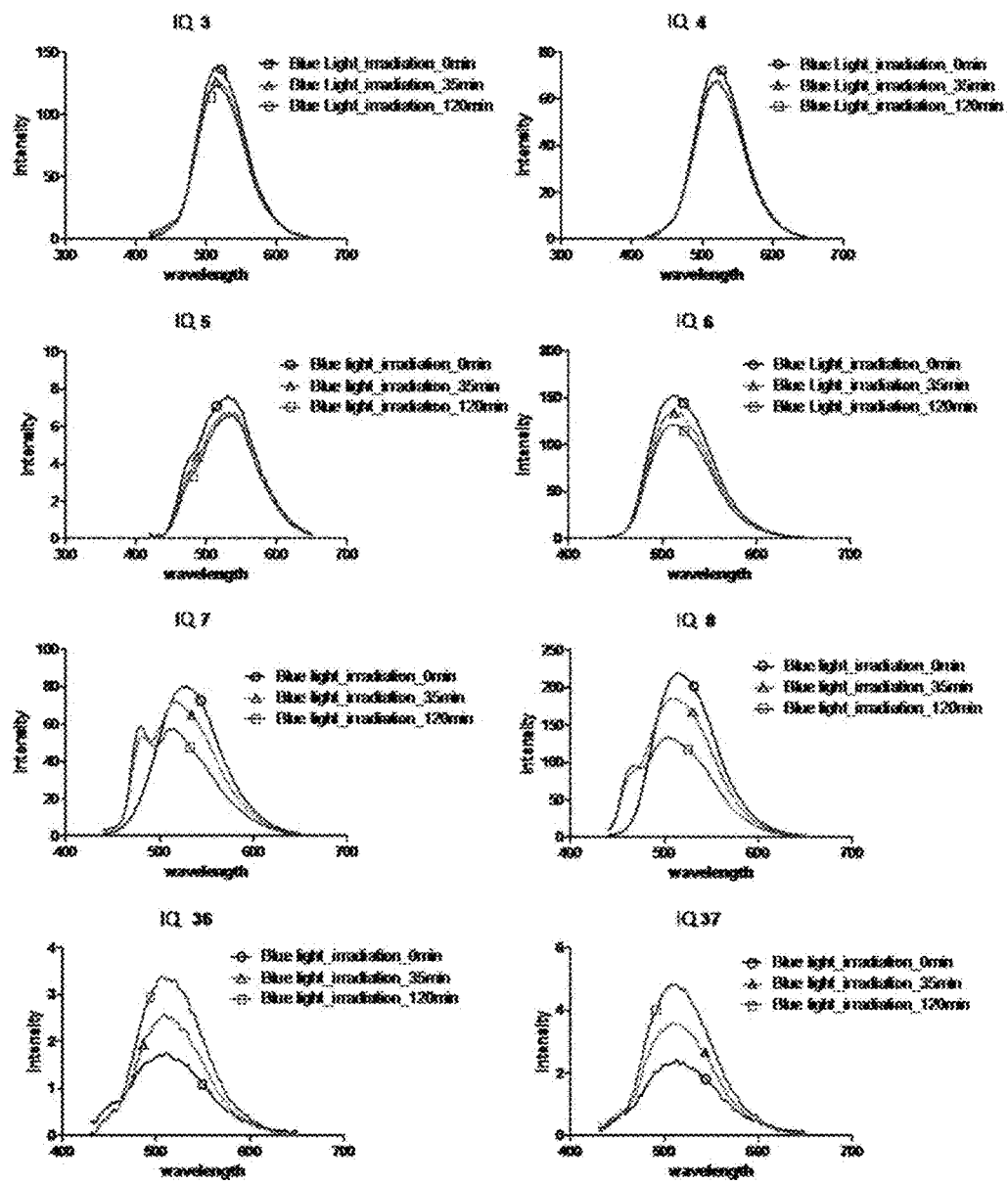

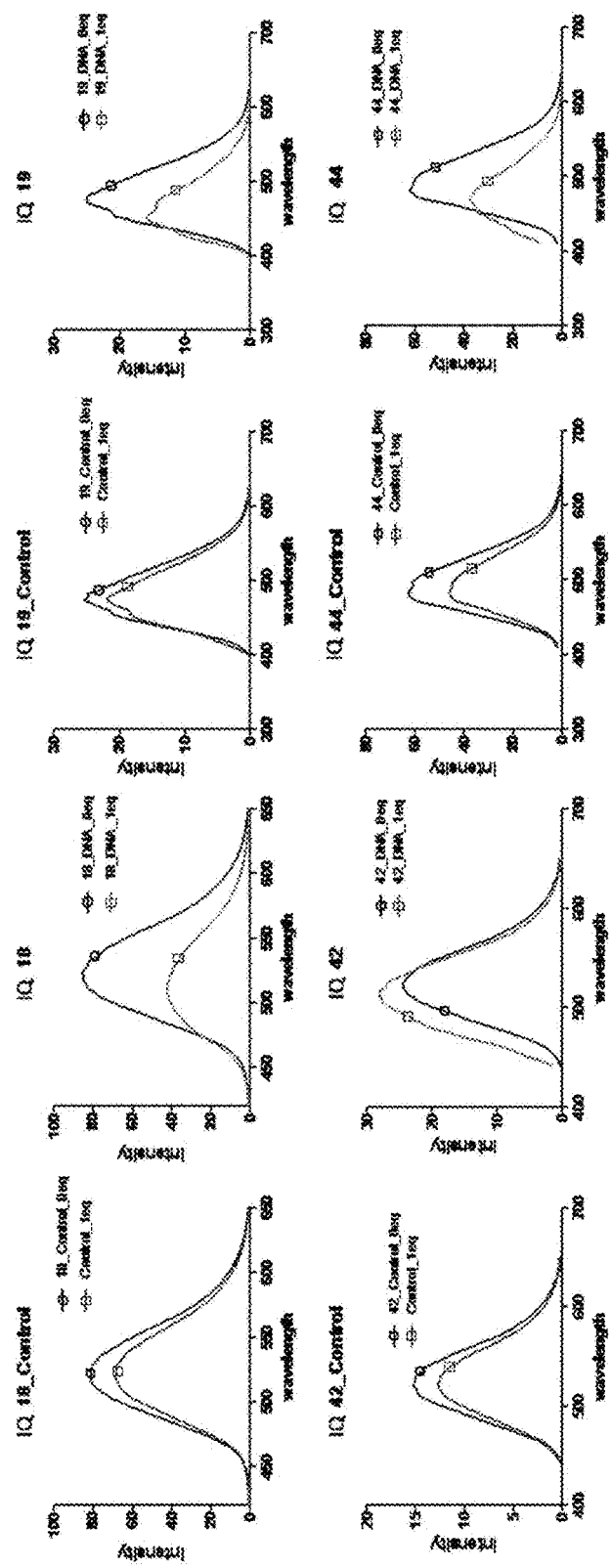
[FIG. 8a]

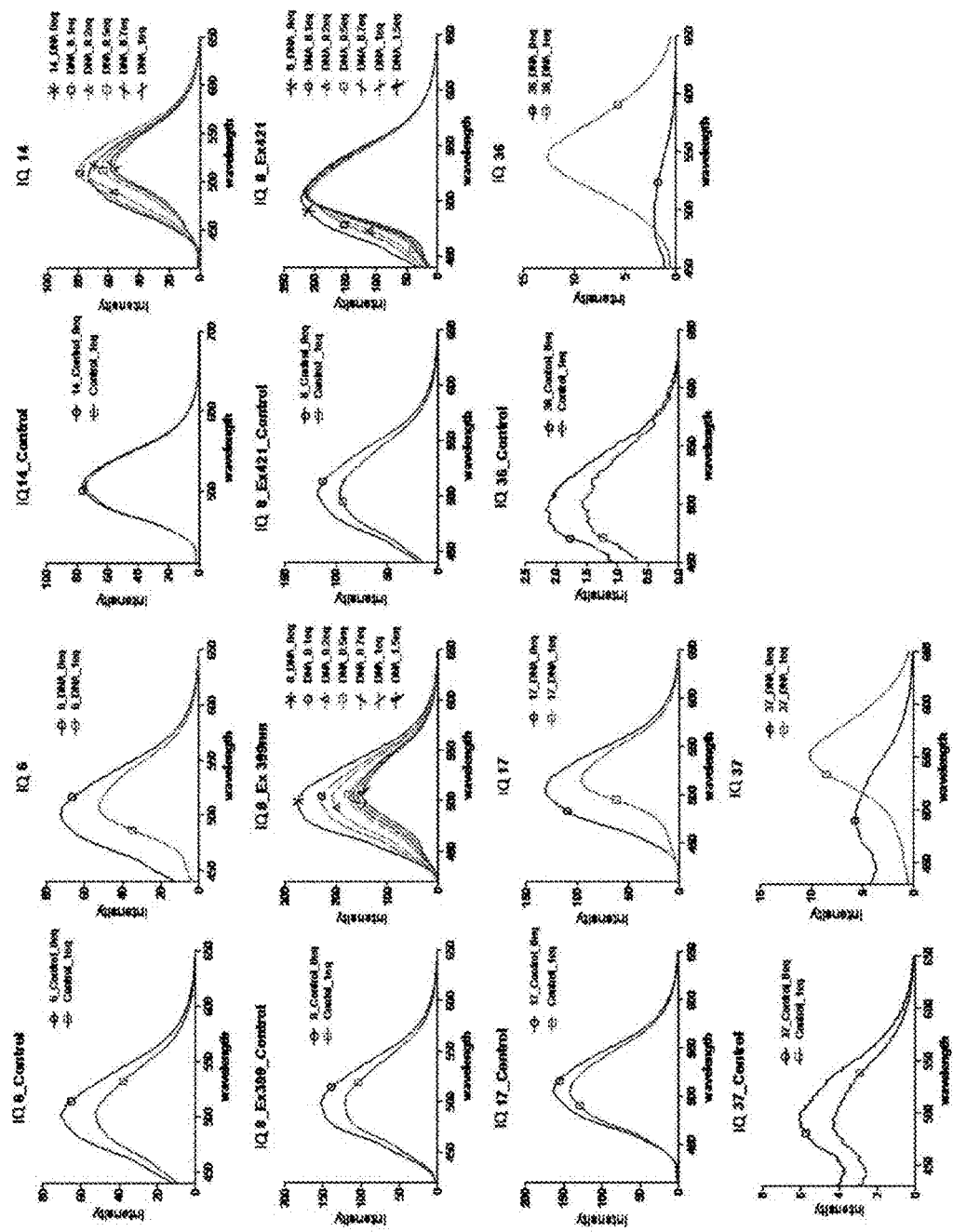
[FIG. 8b]

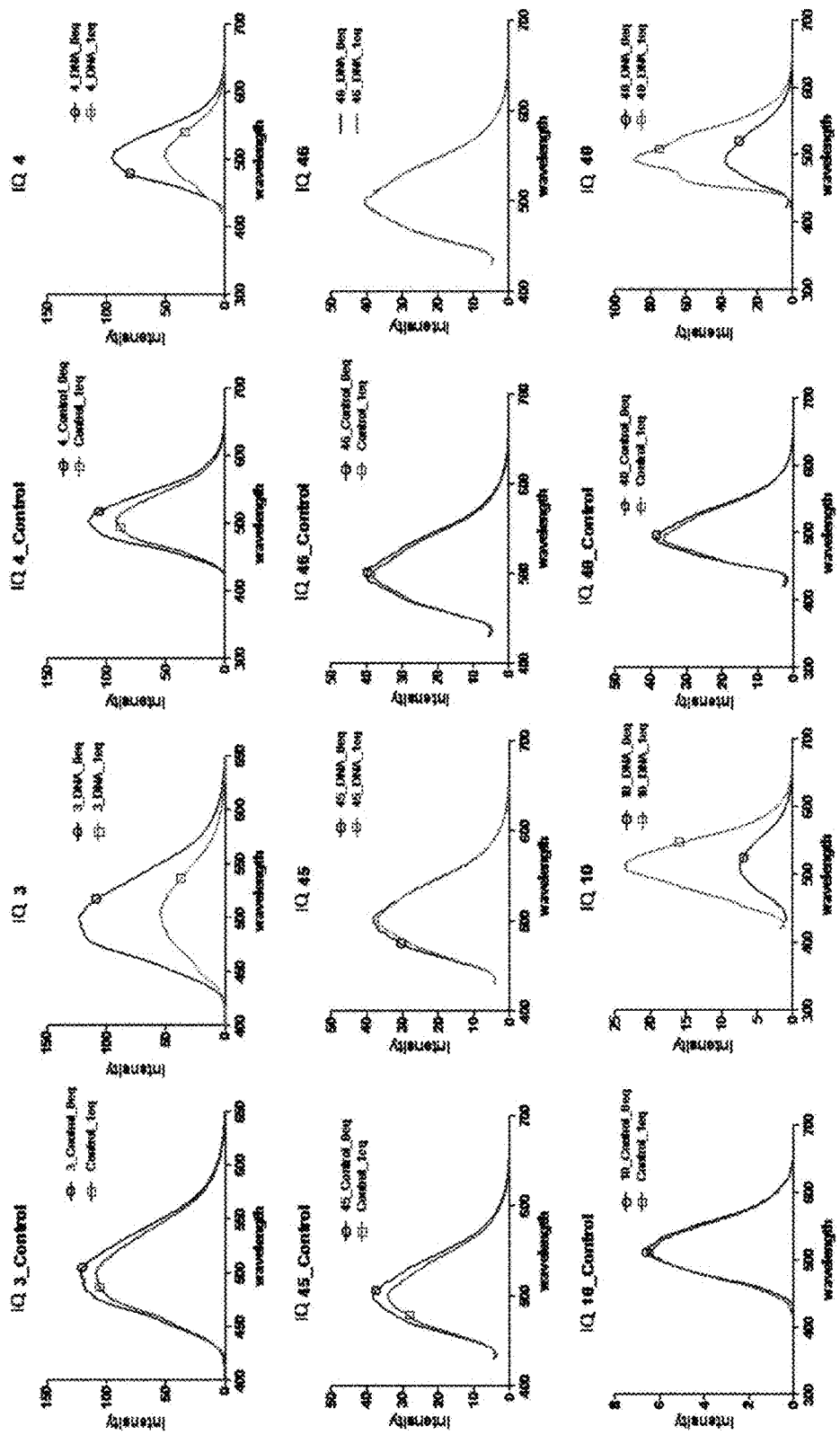
[FIG. 8c]

[FIG. 8d]
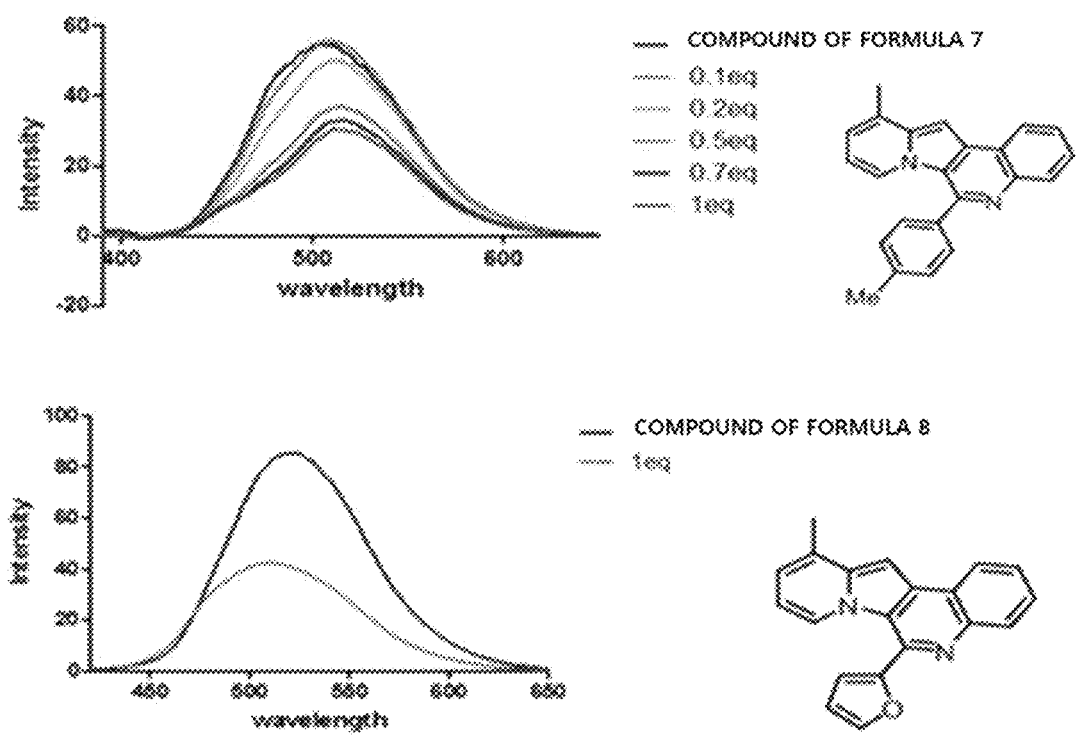

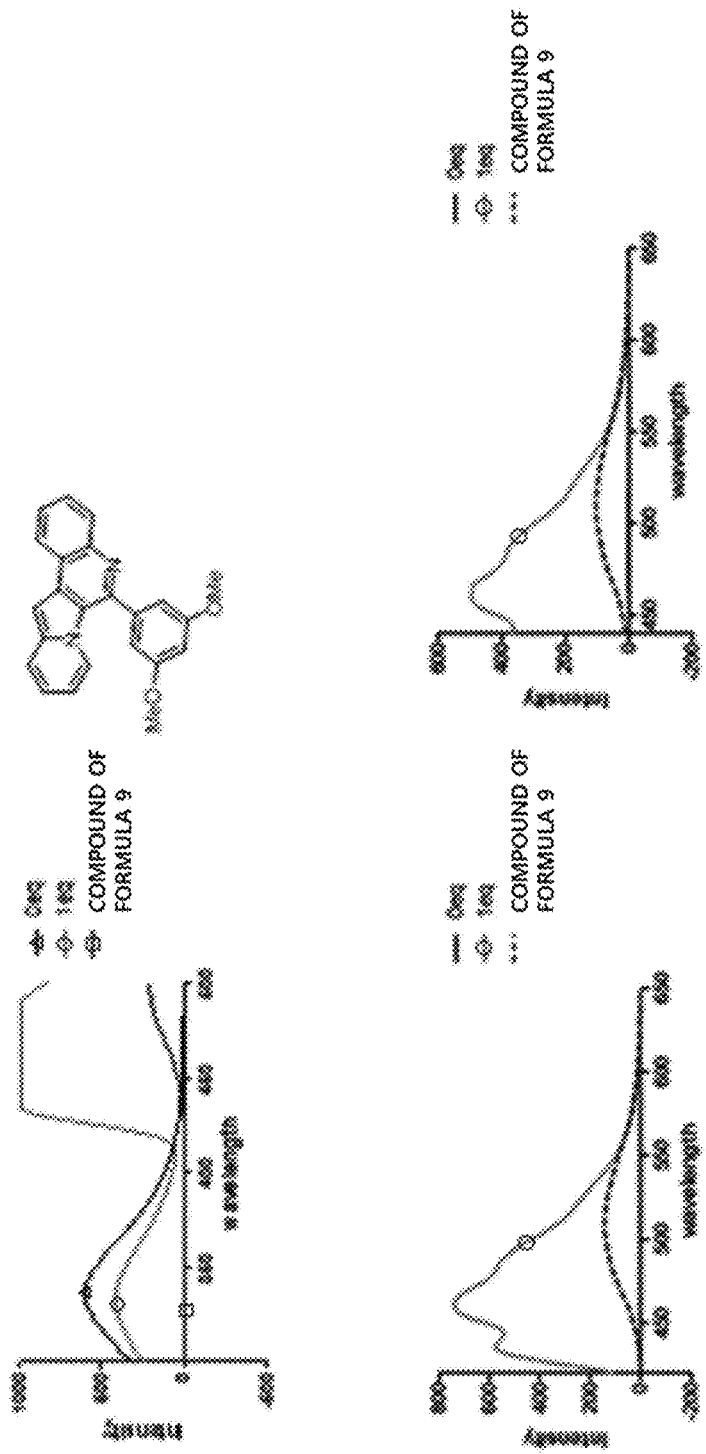
[FIG. 9]

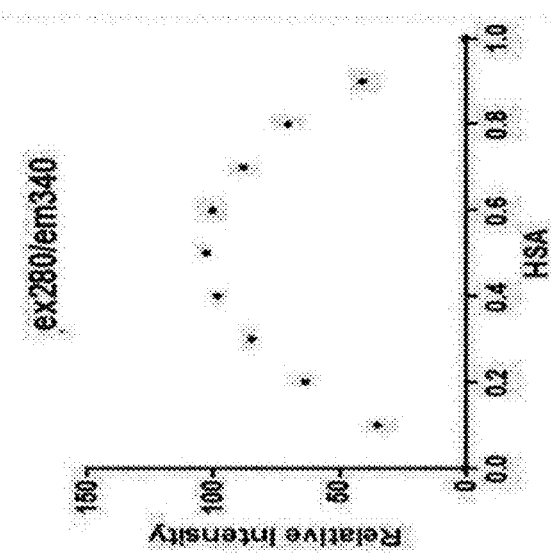
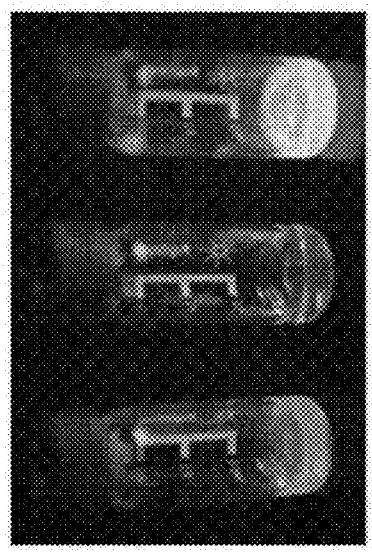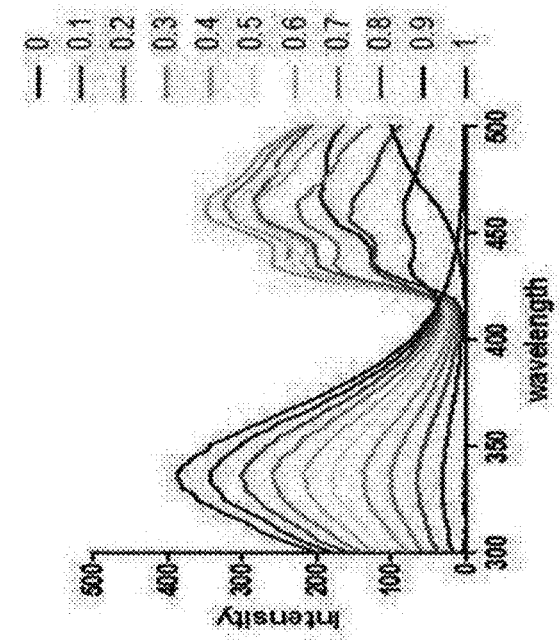
[FIG. 10]

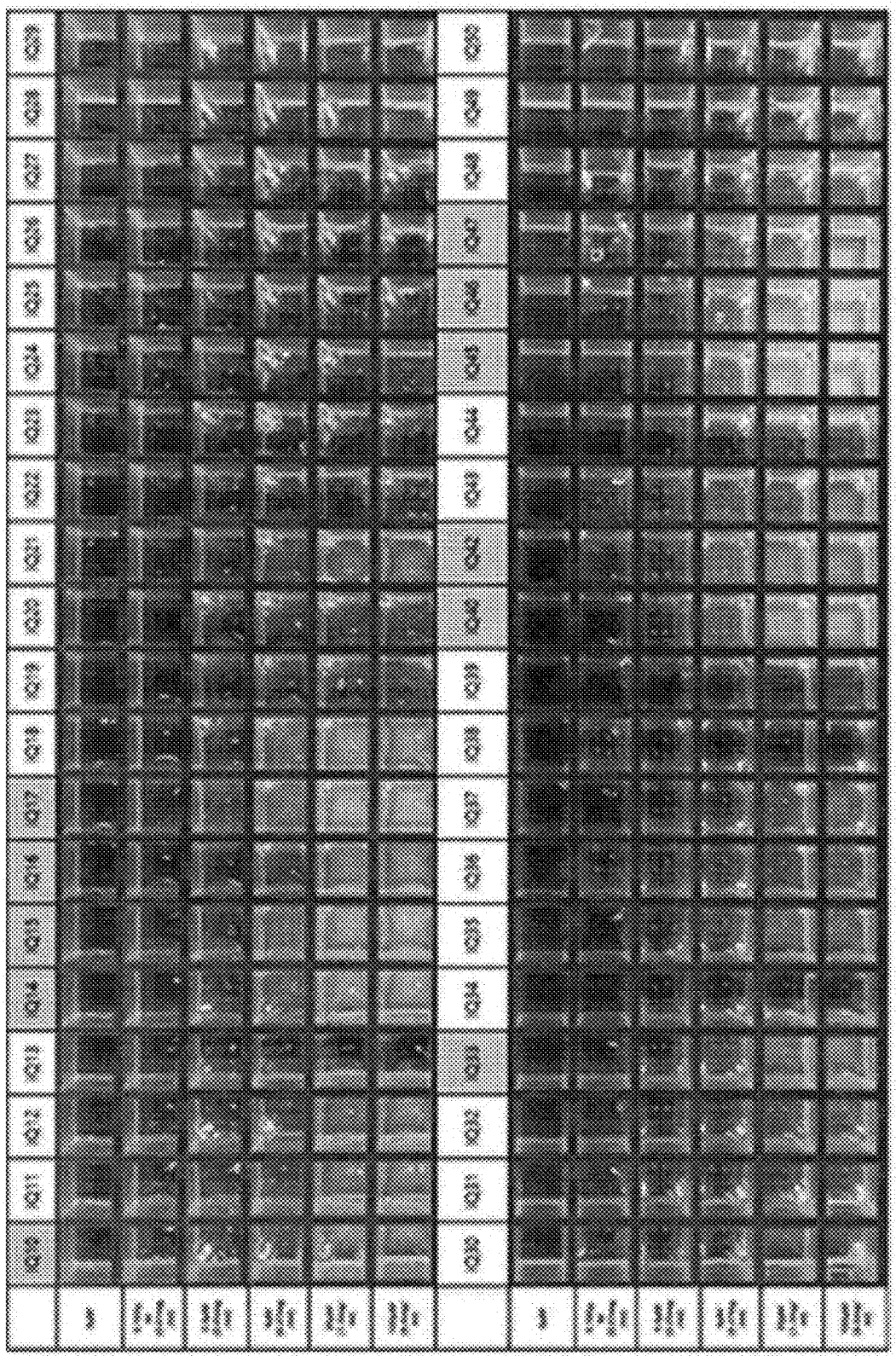
[FIG. 11]

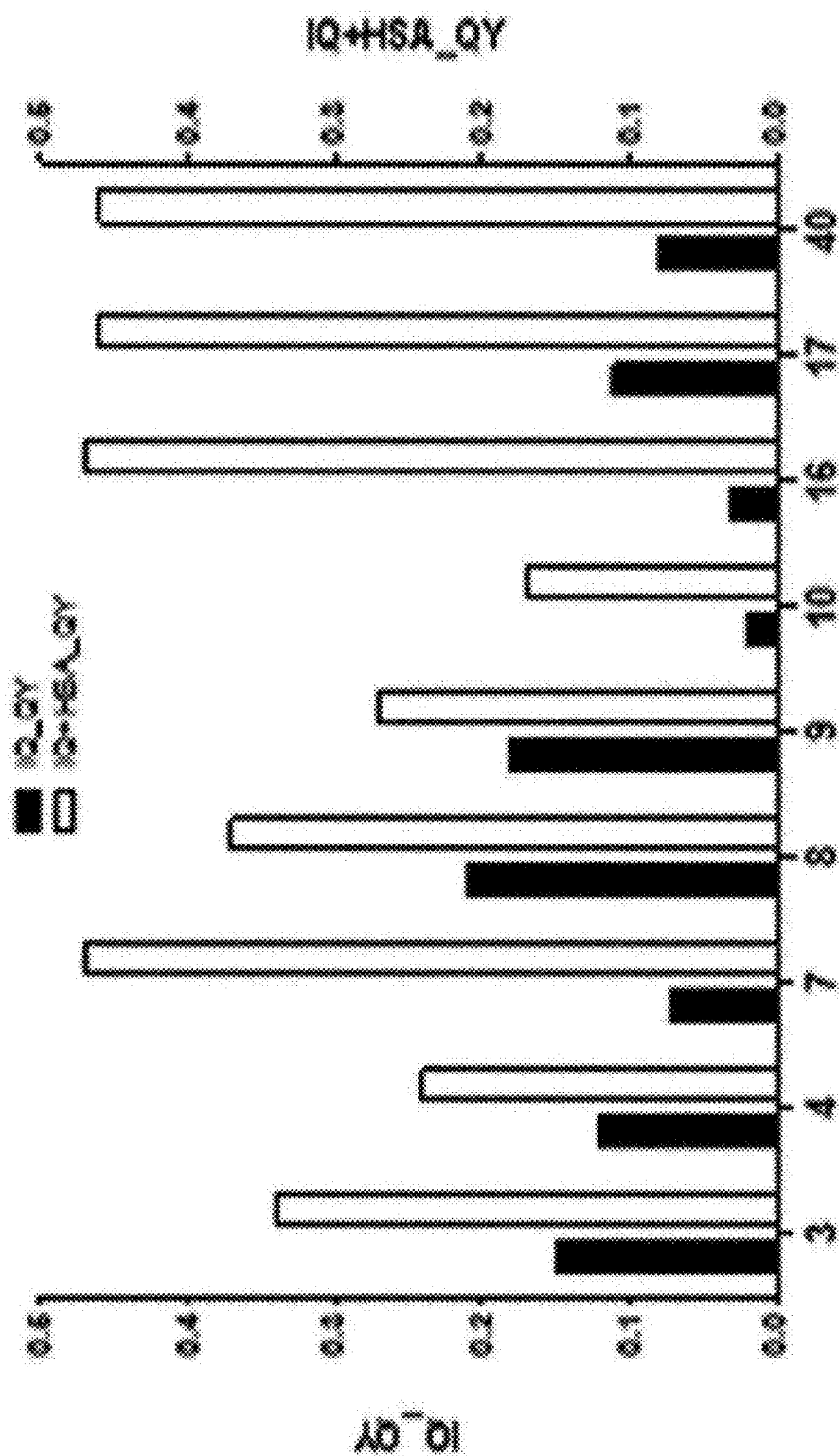
[FIG. 12]

[FIG. 13]
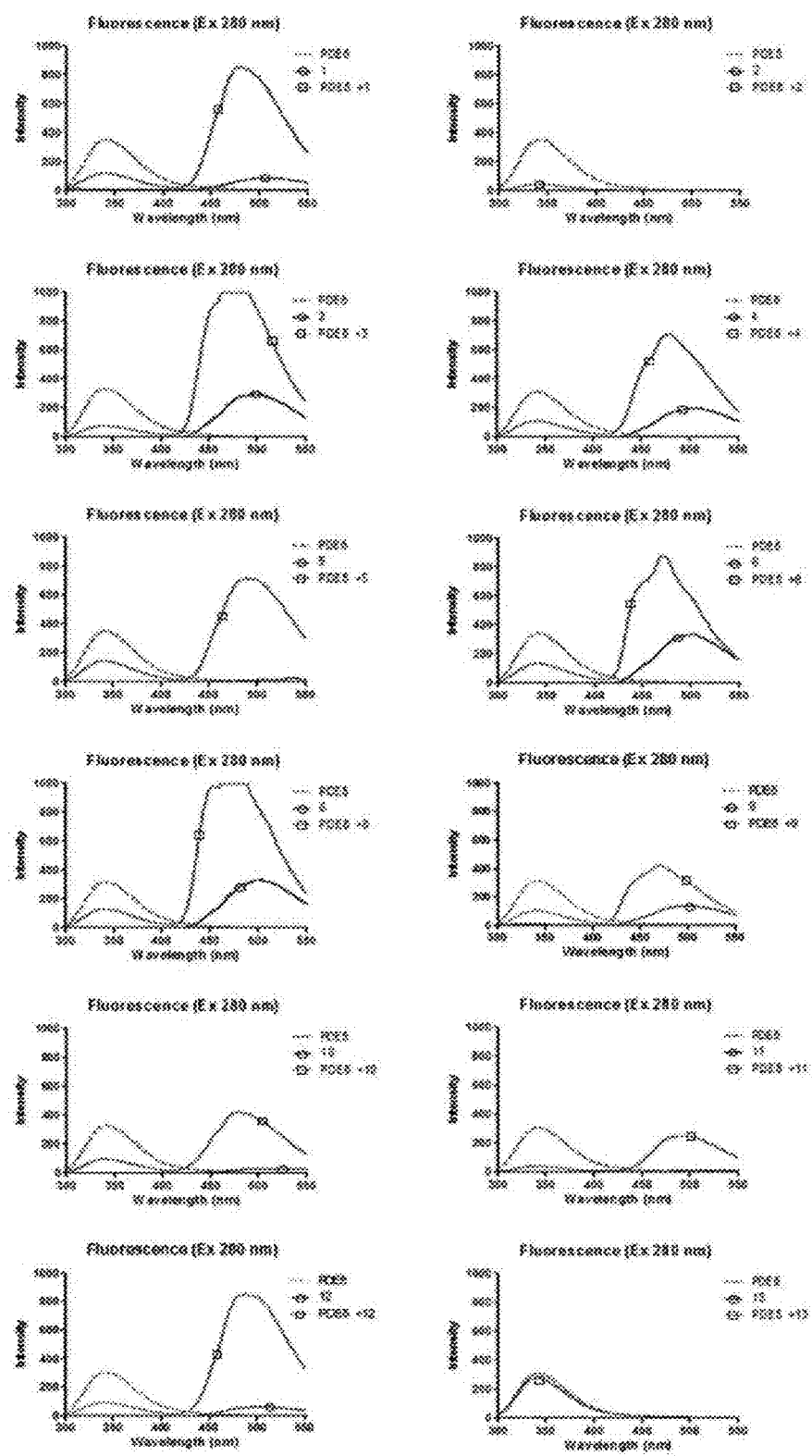

[FIG. 14]
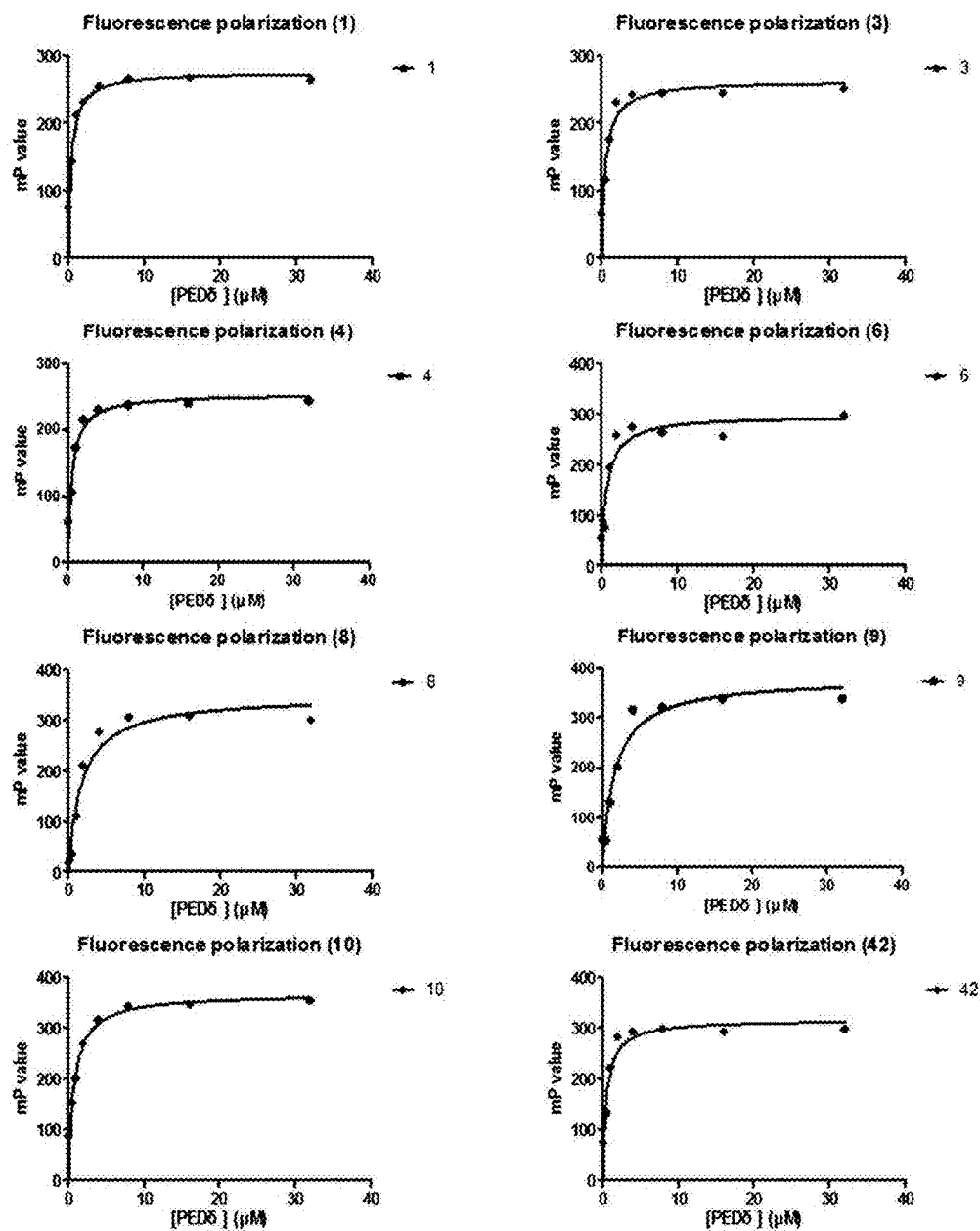

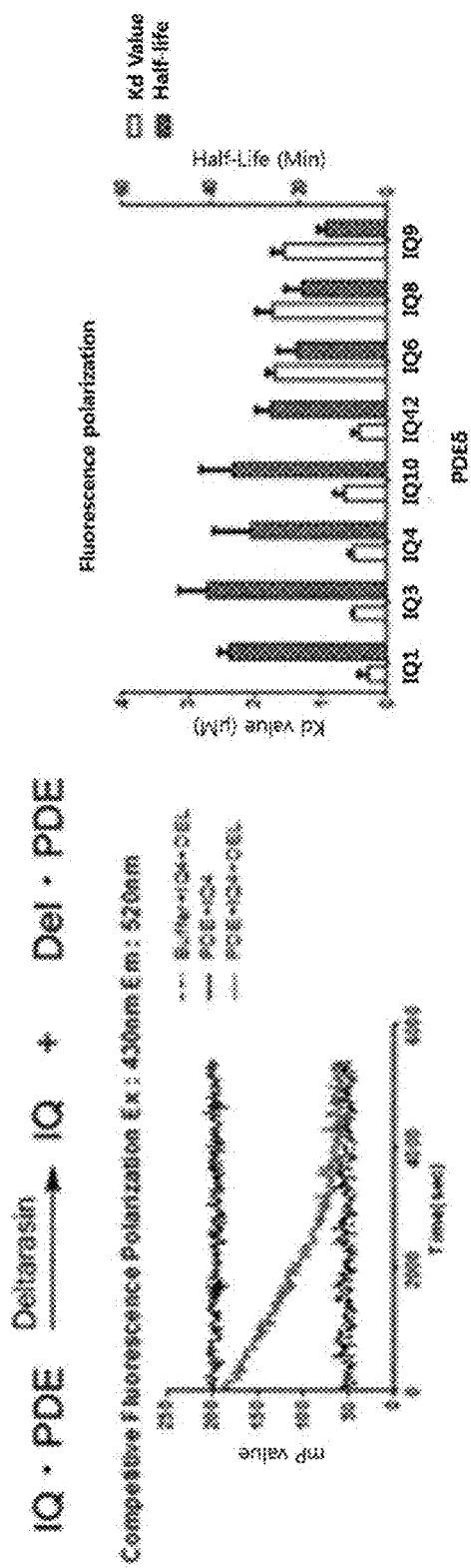
[FIG. 15]

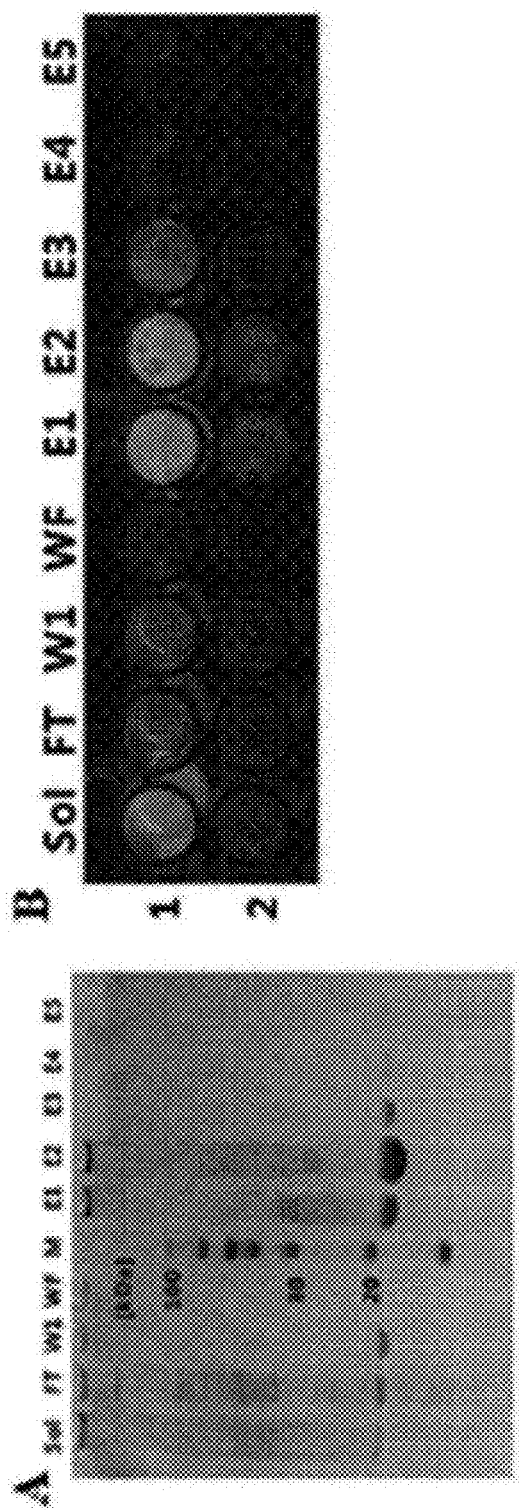
[FIG. 16]

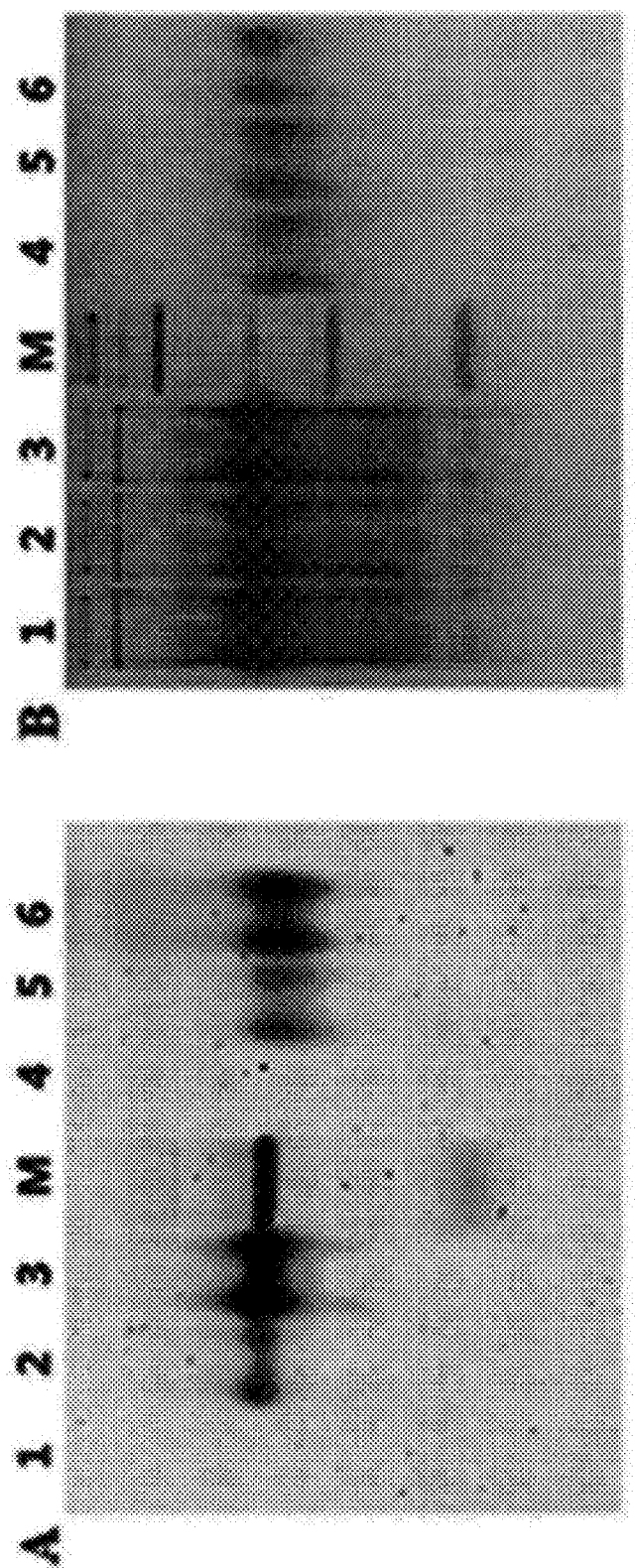
[FIG. 17]

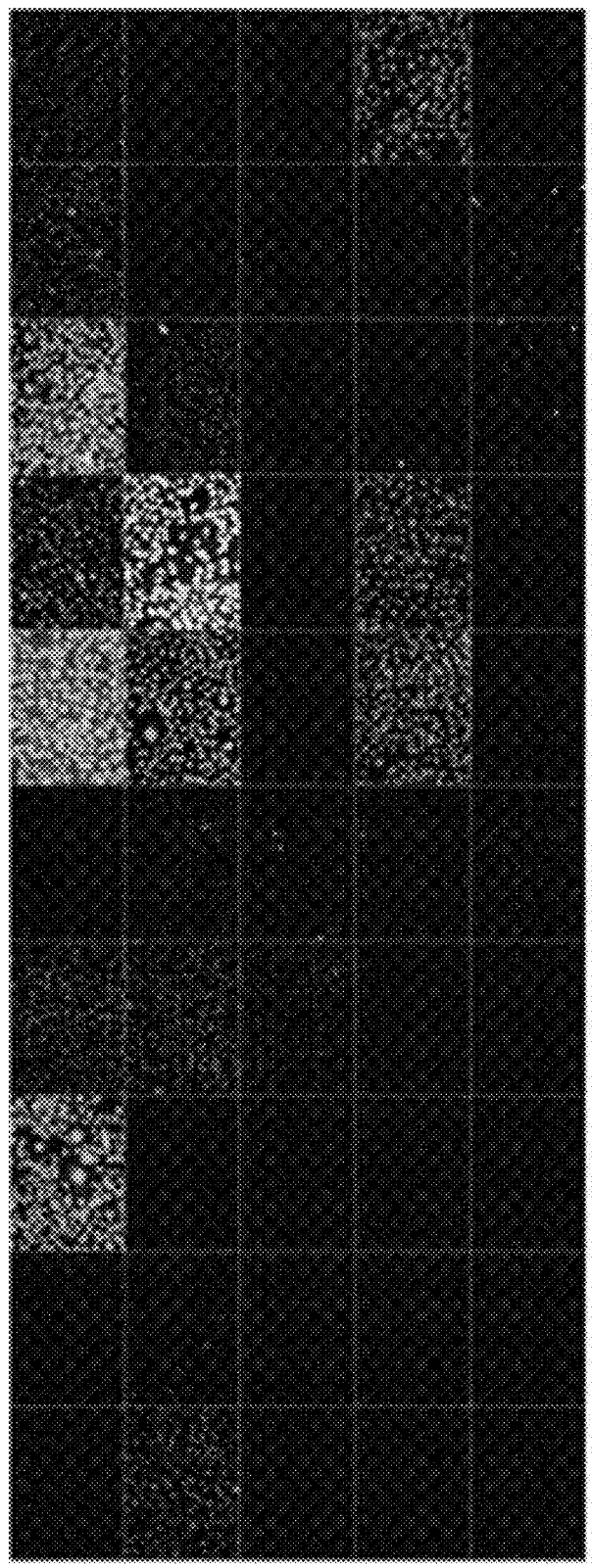
[FIG. 18]

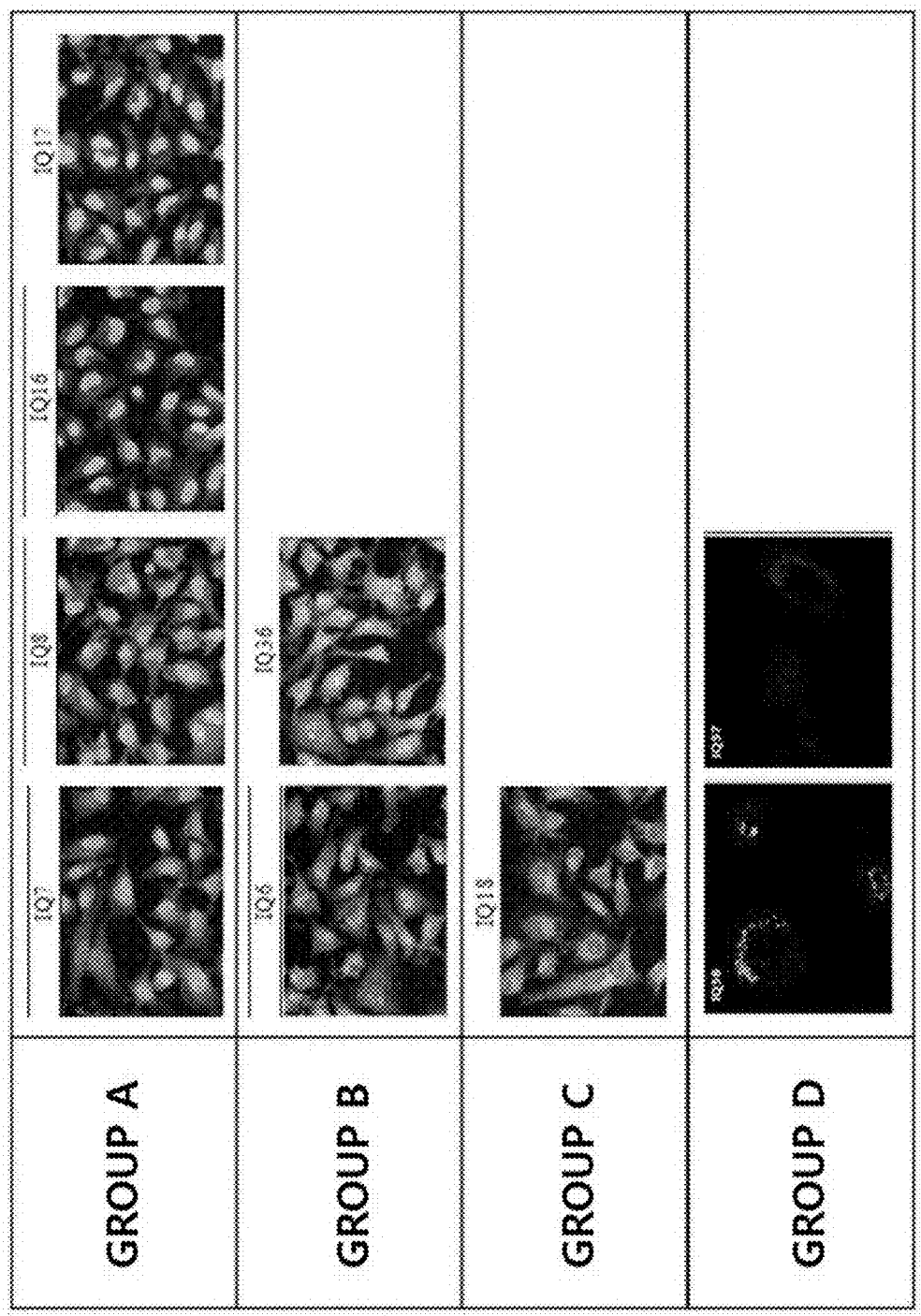
[FIG. 19]

[FIG. 20]
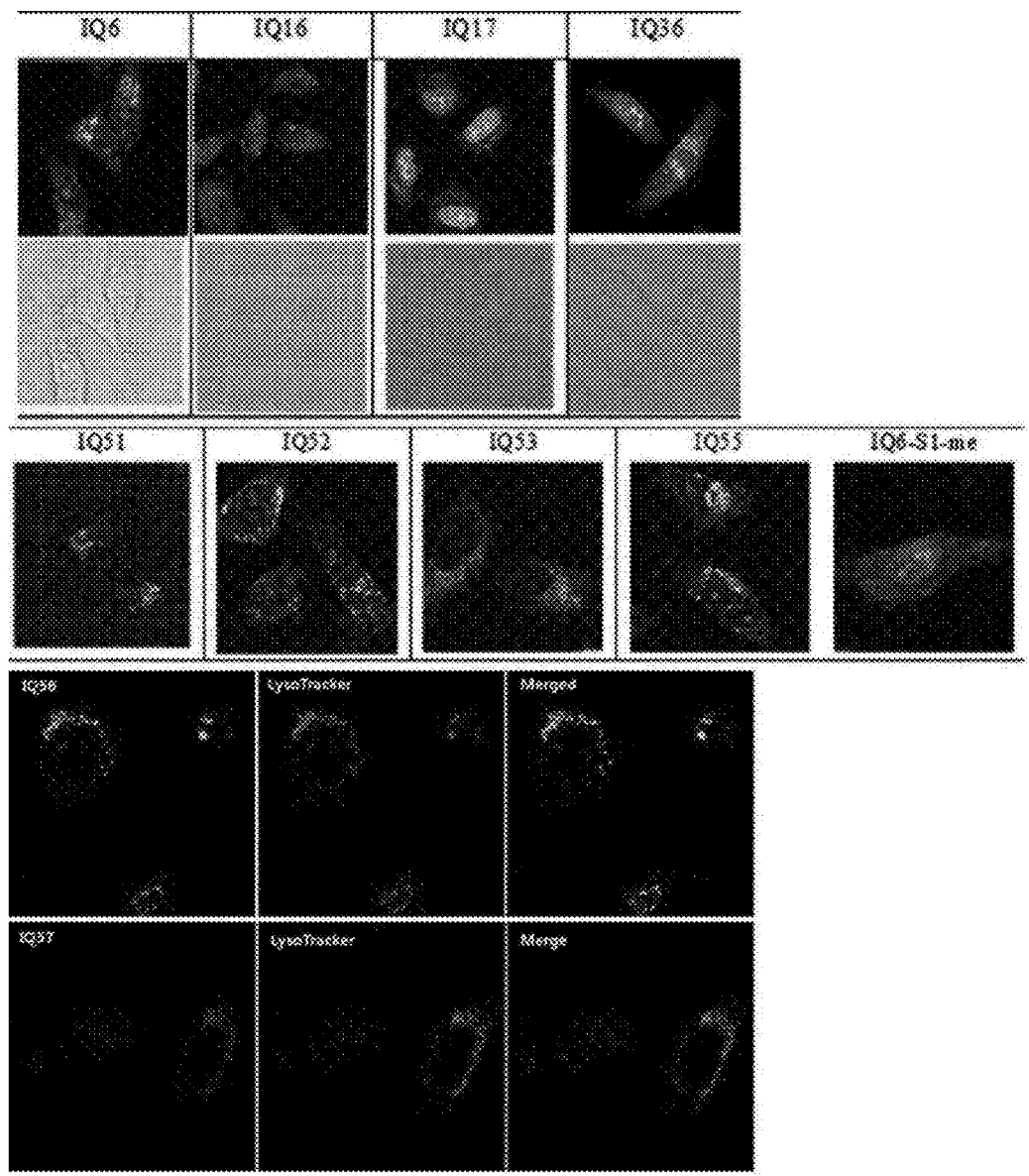

[FIG. 21]
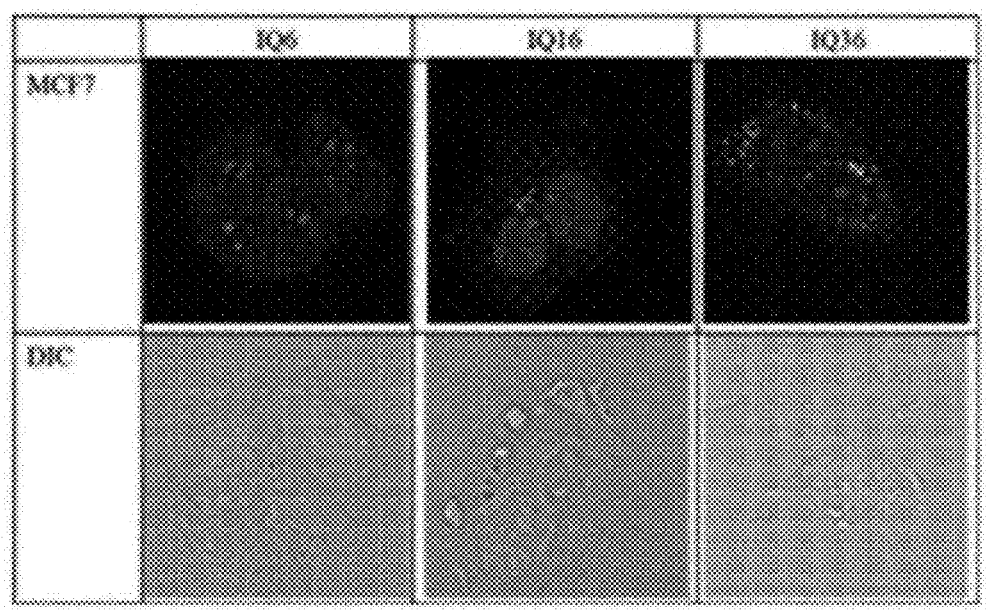
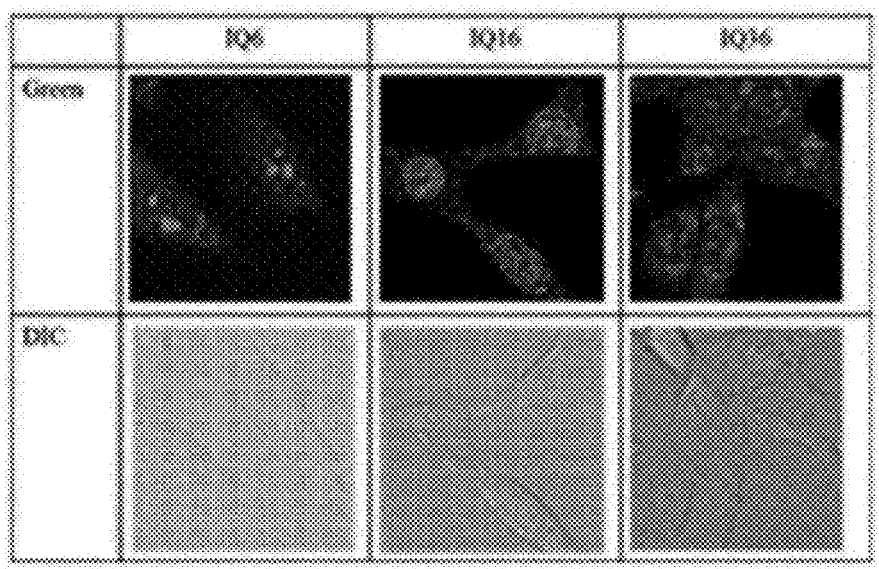

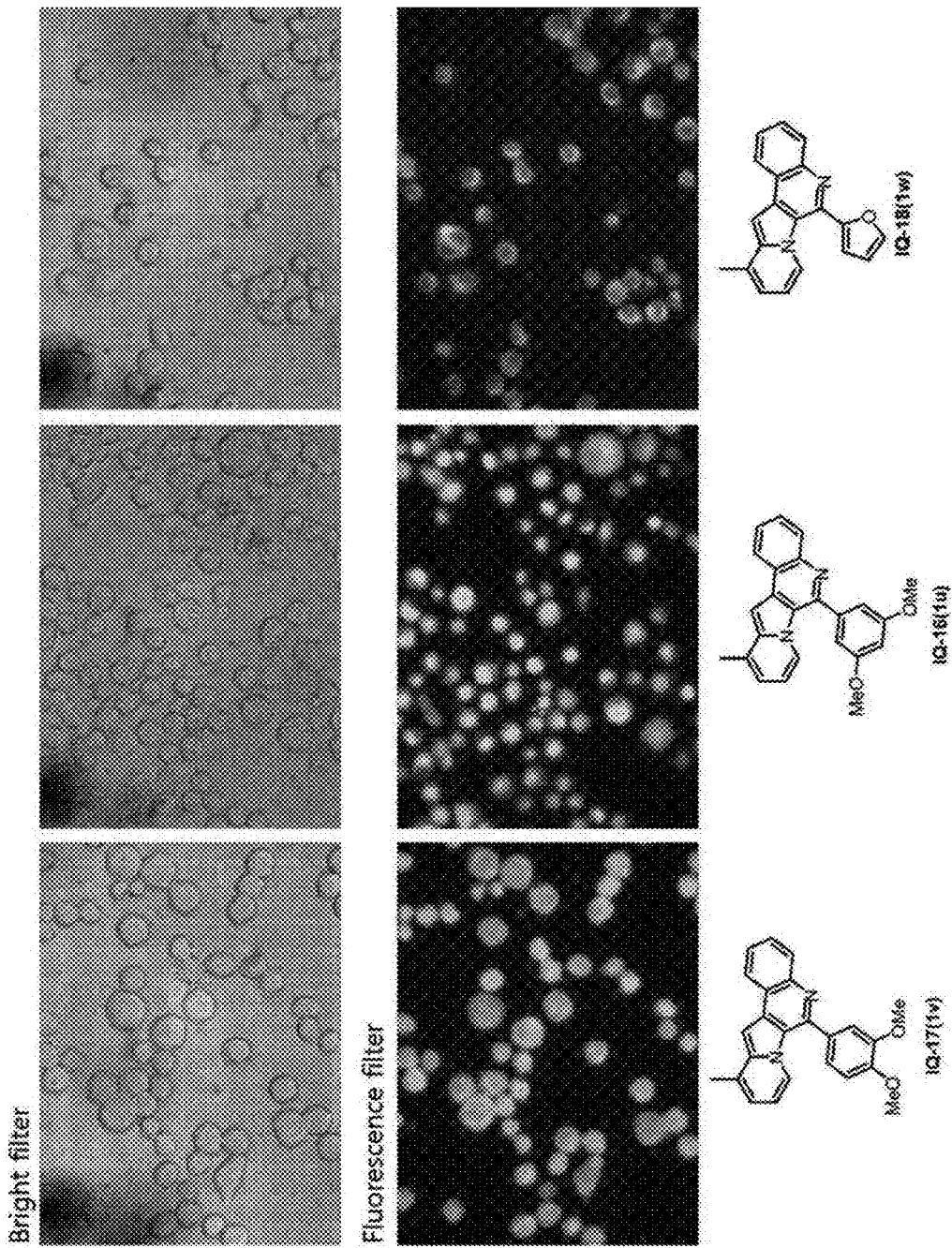
[FIG. 22]

[FIG. 23]
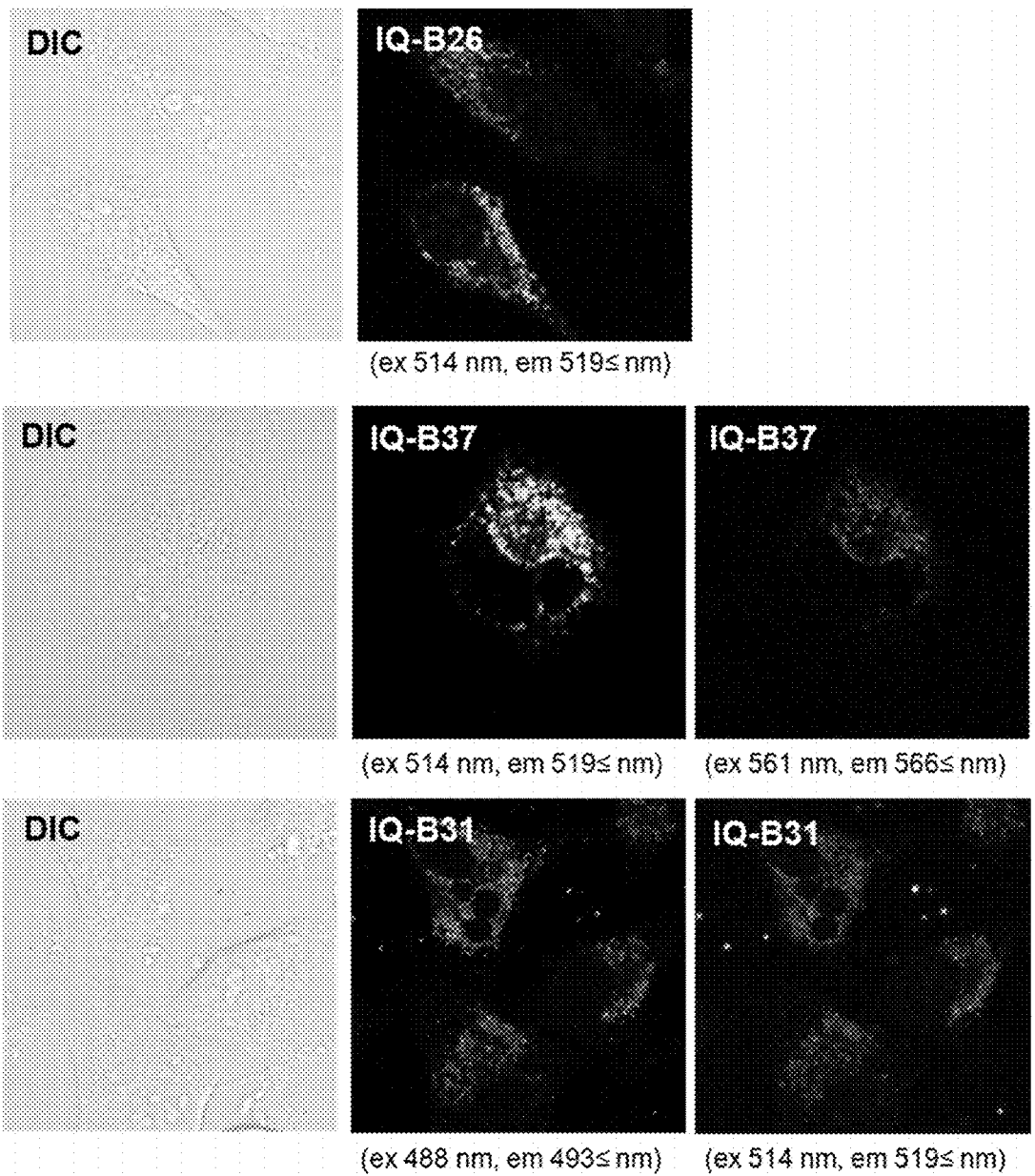

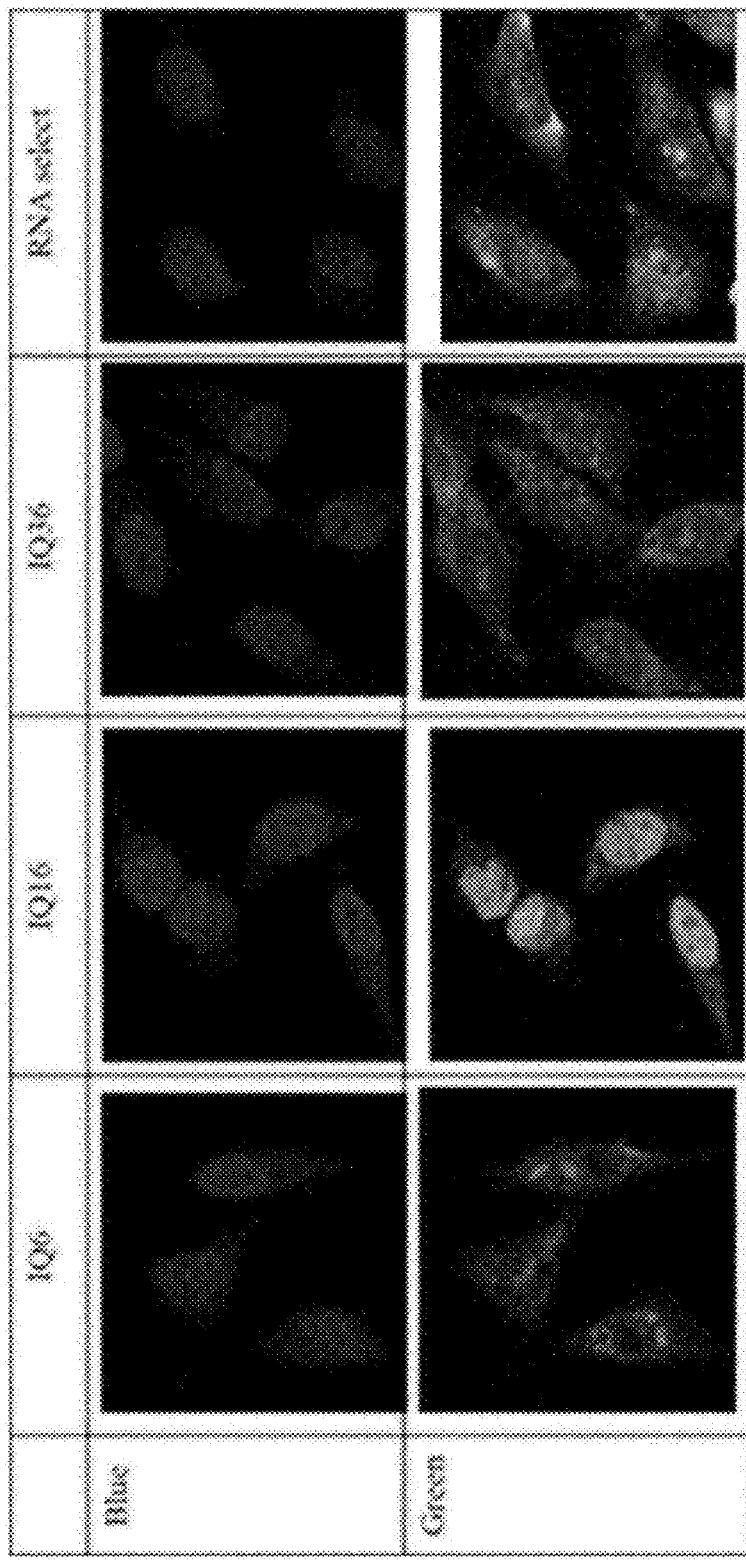
[FIG. 24]

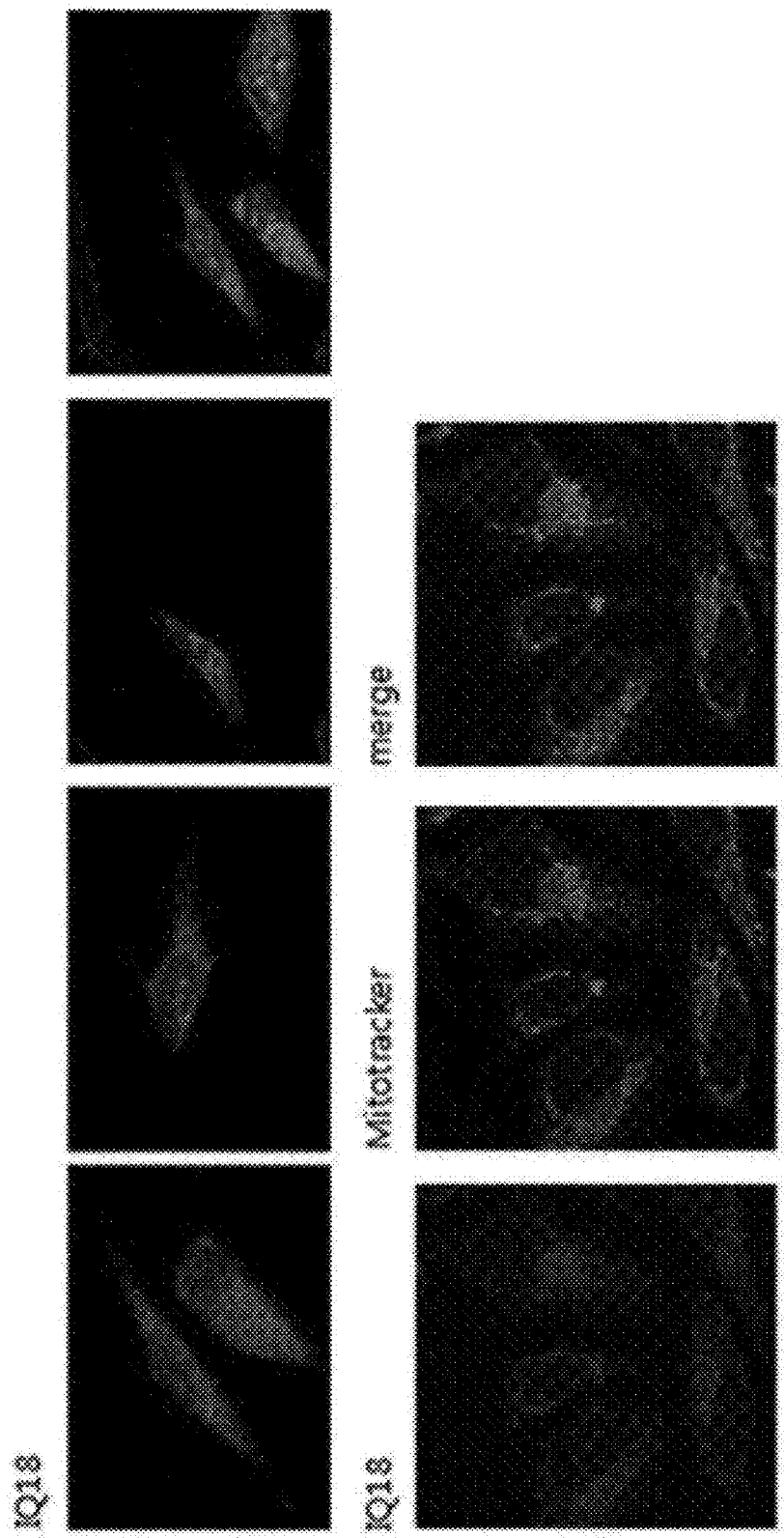
[FIG. 25a]

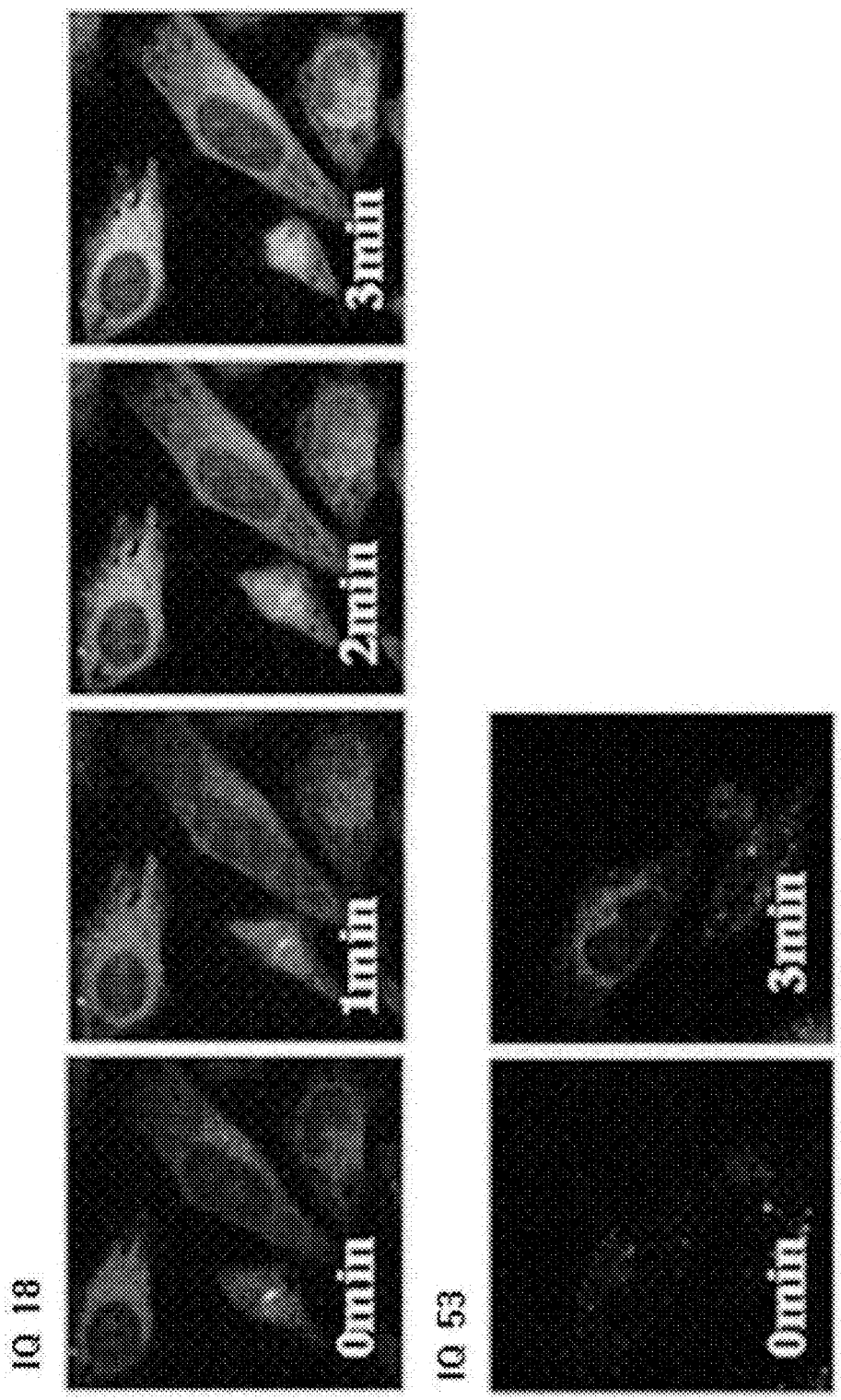
[FIG. 25b]

[FIG. 25c]
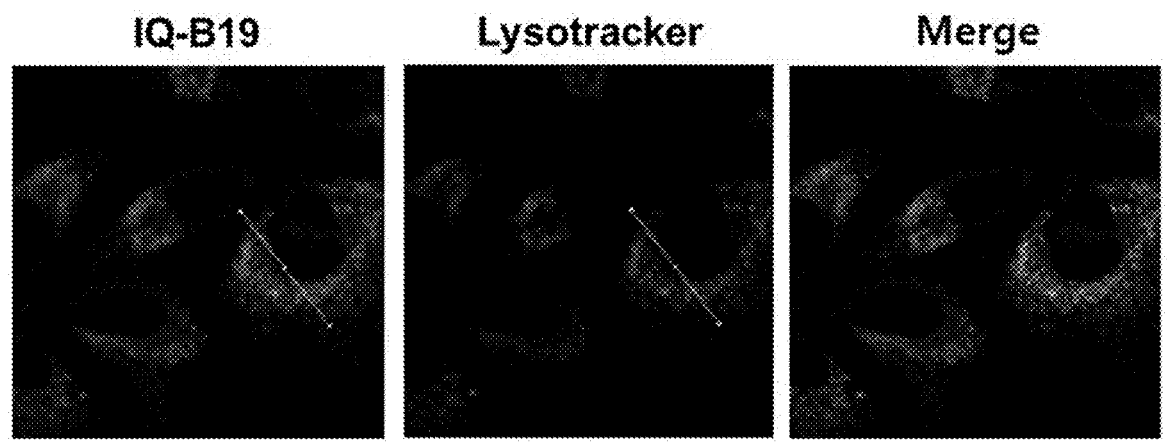

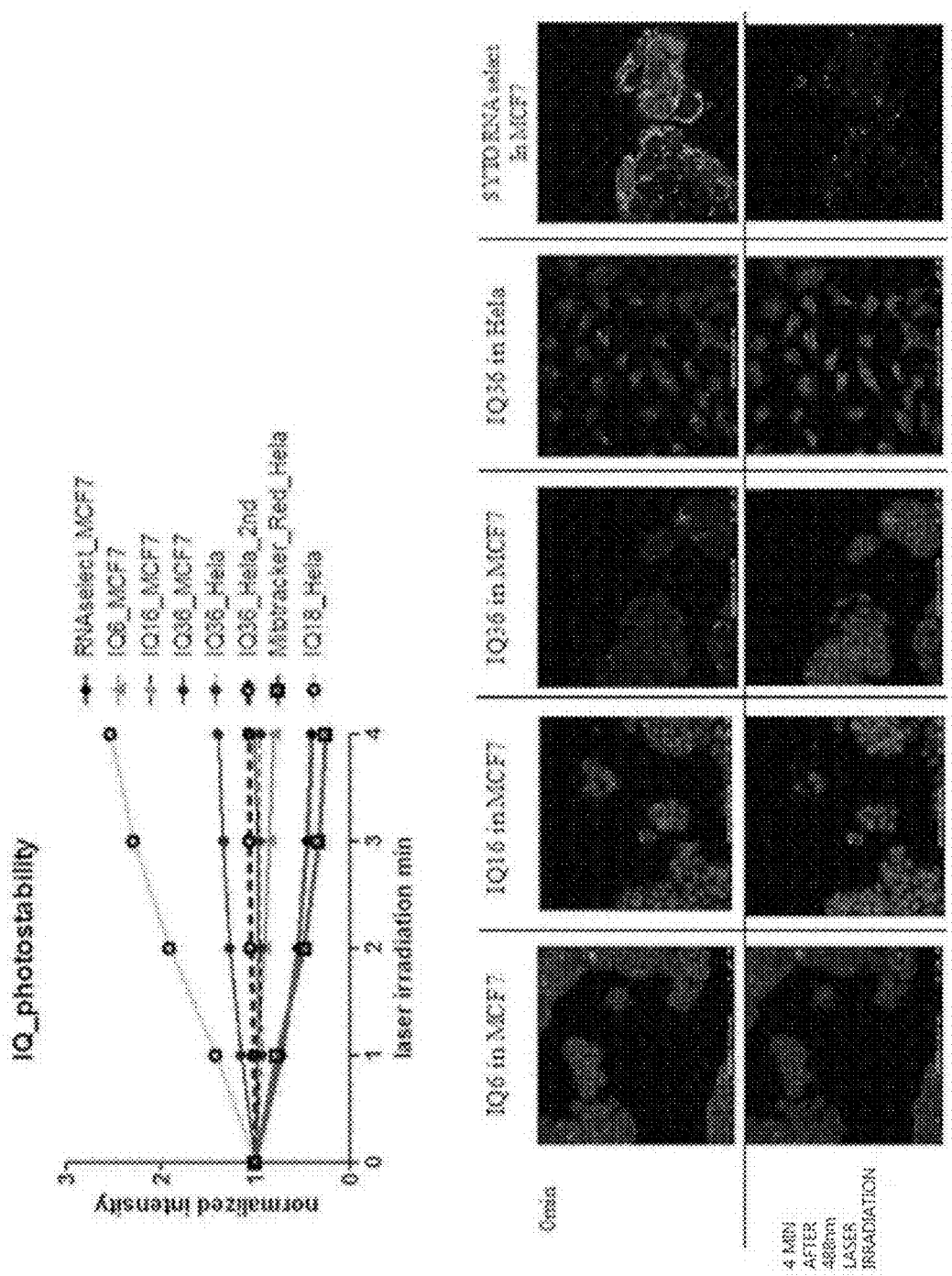
[FIG. 26]

[FIG. 27a]
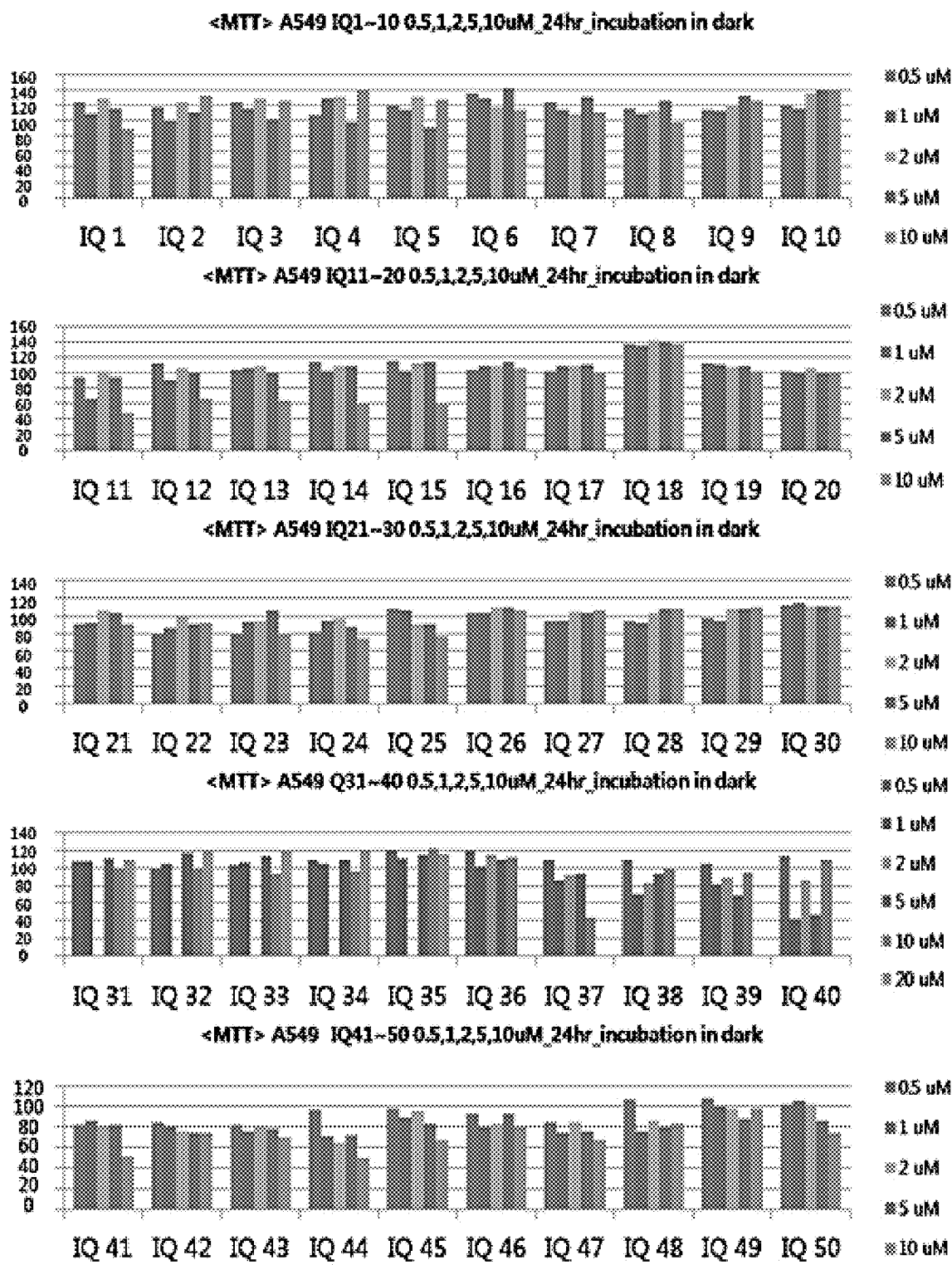

[FIG. 27b]
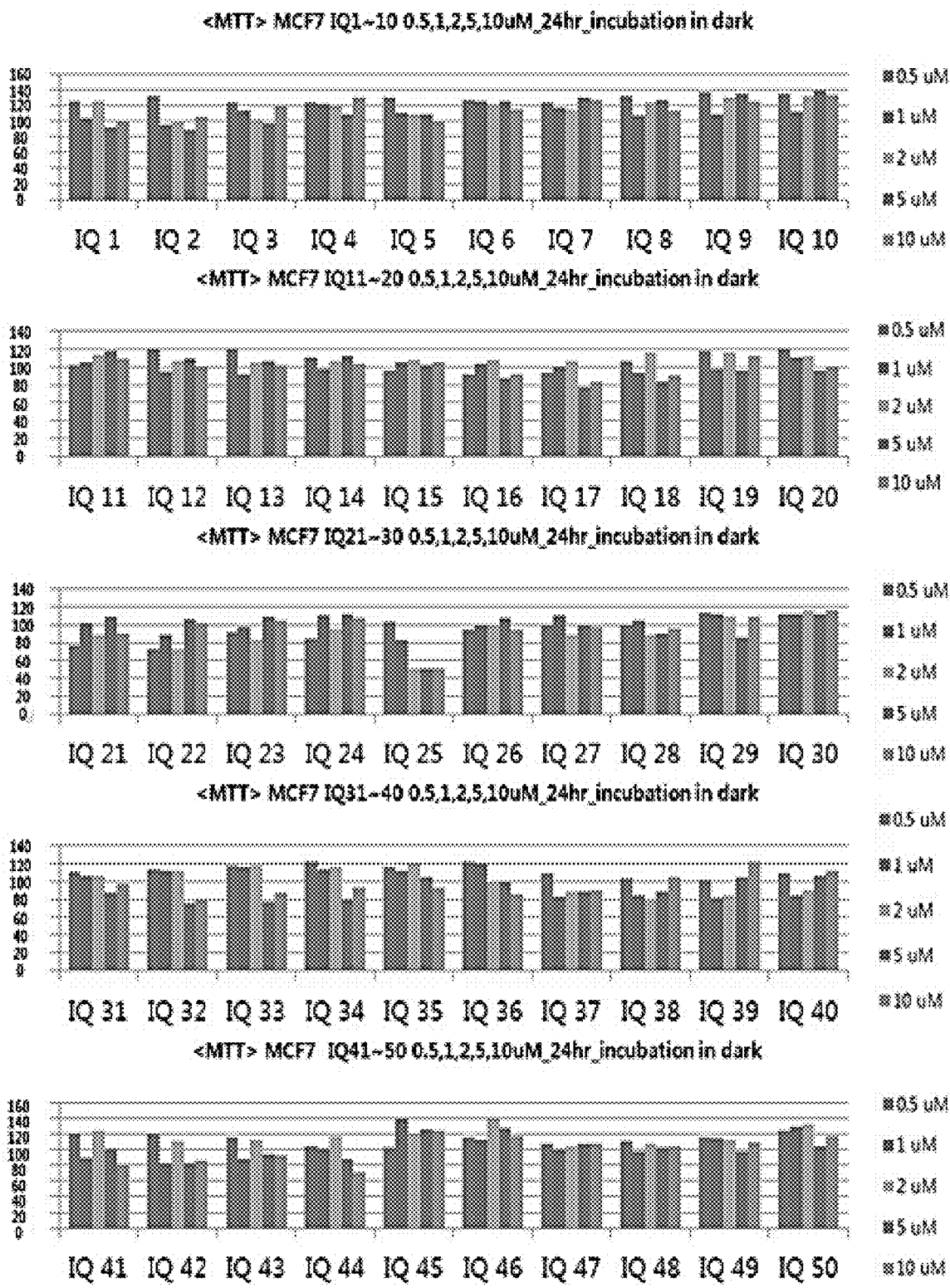

INDOLIZINO [3,2-C] QUINOLINE-BASED FLUORESCENT PROBE

STATEMENT REGARDING GOVERNMENT RIGHTS

The present invention was undertaken with the support of 1) Development of efficient probes for target identification of biologically active small molecules No. NRF-2015R1A2A2A01007646 grant funded by the National Research foundation of Korea and 2) Construction of novel chemical libraries based on bioactive natural products No. NRF-2017R1A2A2A05069364 grant funded by the National Research foundation of Korea.

CROSS-REFERENCE TO RELATED APPLICATION

This application claims priority to and the benefit of Korean Patent Application No. 10-2015-0104107 filed on Jul. 23, 2015, Korean Patent Application No. 10-2016-0092867 filed on Jul. 21, 2016 and International Patent Application No. PCT/KR2016/008059, filed on Jul. 22, 2016, the disclosure of which is incorporated herein by reference in its entirety.

SEQUENCE LISTING

The Sequence Listing submitted in text format (.txt) filed on May 2, 2018, named "SequenceListing.txt", created on May 2, 2018 (651 bytes), is incorporated herein by reference.

TECHNICAL FIELD

The present invention relates to a fluorescent probe composition including an indolizino[3,2-c]quinoline compound, and a nucleic acid/protein/cell imaging method using the same.

BACKGROUND ART

Representative molecules targeted in the development of various small-molecule drugs are indolizine- and quinoline-based compounds. These compounds have different pharmacological characteristic according to an aromatic ring-binding substituent pattern, and thus can be used in various applications, and as examples of the compounds, an antifungal agent, an antimalaria agent, an apoptosis inducer, and an EGFG kinase inhibitor have been reported.

In an effort to design a novel chemical scaffold, a hybrid structure in which the indolizine compound binds to the quinoline compound has attracted attention. Particularly, since 3-acylindolizine and 2-arylquinoline are known to have anticancer activity, it has been suggested that a novel heteroaromatic compound as the hybrid structure of the 3-acylindolizine and the 2-arylquinoline can have the activity of a fluorescent sensor in addition to the anticancer activity.

Meanwhile, since a heterocyclic system exhibiting strong fluorescence can be used as a molecular probe that can monitor a reaction with a target molecule in biochemical research, there is an increasing demand for novel fluorophores having an intrinsic photophysical characteristic. Particularly, to monitor the interaction between a ligand and a target, there is a demand for the development of environment-sensitive fluorophores changed in optical characteristics according to a physicochemical property of an environment surrounding molecules.

In addition, the development of an organic fluorophores is technology essential for cell imaging and protein function research, and it is necessary to develop fluorophores applicable to an aqueous solution which emits fluorescence with respect to light with a specific wavelength and is free from interference by other components in a cell. Most organic fluorophores that have been developed until now aggregate themselves due to poor solubility in an aqueous solution or cause aggregation of proteins. That is, there is an increasing demand for fluorophores which can compensate for the disadvantages of conventional fluorophores, can also be used in an aqueous solution and under buffer conditions, do not cause protein aggregation, and have high brightness. For example, a conventionally used fluorescent material such as Alexa 488 or fluorescein has a disadvantage that quenching occurs on its own due to an excitation wavelength and a wavelength exhibiting fluorescence being so close, and RNASelect or LysoTracker also has low photostability in cell staining, and therefore it is necessary to develop a new fluorophores overcoming such disadvantages (see Korean Patent No. 10-1019390).

DISCLOSURE

Technical Problem

To solve the above-mentioned problems, the inventors have conducted research to develop a fluorescent probe having further improved characteristics, and thus found that some indolizino[3,2-c]quinoline-based compounds exhibit preferable optical characteristics, and provide an aqueous solution system and a bio-friendly and useful fluorophores platform.

Therefore, the present invention is directed to providing compounds with excellent environment-sensitivity, fluorescence intensity, photostability, nucleic acid/protein bindability and intracellular permeability, and a nucleic acid-, protein- or cell-imaging method using the same.

However, technical problems to be solved in the present invention are not limited to the above-described problems, and other problems which are not described herein will be fully understood by those of ordinary skill in the art from the following description.

Technical Solution

The present invention provides a fluorescent probe composition, which includes an indolizino[3,2-c]quinoline compound represented by Formula 1 below or a pharmaceutically acceptable salt thereof:

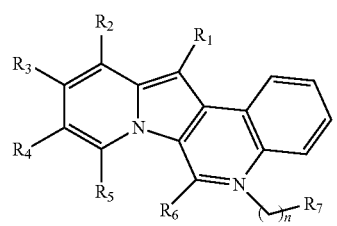

[Formula 1]

In Formula 1,

R$_1$, R$_4$ and R$_5$ are each independently selected from the group consisting of hydrogen, halogen, C$_{1-12}$ alkyl, C$_{1-12}$ alkoxy, COOR$_8$, substituted or unsubstituted C$_{6-20}$ aryl, substituted or unsubstituted C$_{2-20}$ alkoxy, heteroaryl,

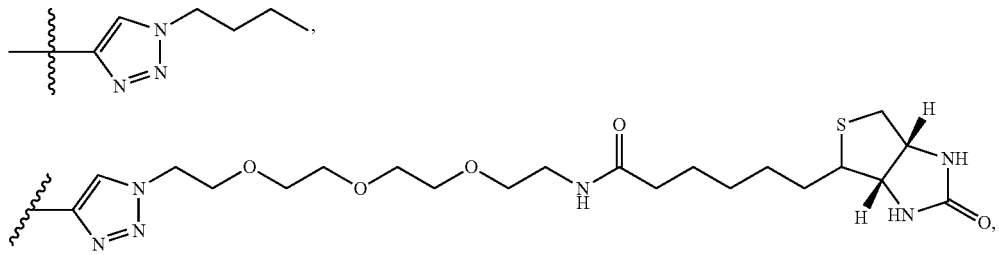

C$_{2-12}$ alkynyl, substituted C$_{2-12}$ alkenyl, amine, hydroxyl, aldehyde, nitrile, amide, phenoxy and boronic ester, R$_2$ and R$_3$ are bound with each other to form an aromatic ring, or each independently selected from the group consisting of hydrogen, halogen, C$_{1-12}$ alkyl, C$_{1-12}$ alkoxy, COOR$_8$, substituted or unsubstituted C$_{6-20}$ aryl, substituted or unsubstituted C$_{2-20}$ heteroaryl,

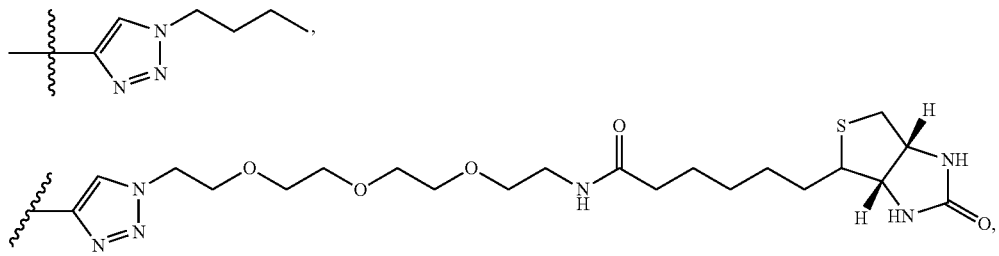

C$_{2-12}$ alkynyl, substituted C$_{2-12}$ alkenyl, amine, hydroxyl, aldehyde, nitrile, amide, phenoxy and boronic ester, R$_6$ is selected from the group consisting of C$_{1-12}$ alkyl, substituted C$_{2-12}$ alkenyl,

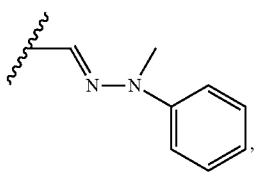

substituted or unsubstituted C$_{6-20}$ aryl, and substituted or unsubstituted C$_{2-20}$ heteroaryl, n is 0, 1, 2 or 3, R$_7$ is selected from the group consisting of hydrogen, hydroxyl, halogen and C$_{1-12}$ alkyl, and R$_8$ is selected from the group consisting of hydrogen, C$_{1-12}$ alkyl and C$_{2-12}$ alkynyl.

In one exemplary embodiment of the present invention, R$_1$, R$_4$ and R$_5$ are each independently selected from the group consisting of hydrogen, C$_{1-12}$ alkyl, COOR$_8$, and an amine, R$_2$ and R$_3$ are bound with each other to form an aromatic ring, or each independently selected from the group consisting of hydrogen, aldehyde, C$_{1-12}$ alkyl, substituted C$_{2-12}$ alkenyl, substituted or unsubstituted C$_{6-20}$ aryl, substituted or unsubstituted C$_{2-20}$ heteroaryl and a nitrile, R$_6$ is selected from the group consisting of C$_{1-12}$ alkyl, substituted C$_{2-12}$ alkenyl, substituted or unsubstituted C$_{6-20}$ aryl, and substituted or unsubstituted C$_{2-20}$ heteroaryl, n is 0, 1, 2 or 3, R$_7$ is selected from the group consisting of hydrogen, hydroxyl, halogen and C$_{1-6}$ alkyl, and R$_8$ is selected from the group consisting of hydrogen, C$_{1-12}$ alkyl and C$_{2-12}$ alkynyl.

In another exemplary embodiment of the present invention, the substituted C$_{2-12}$ alkenyl is linked to a substituent selected from the group consisting of aldehyde, substituted or unsubstituted C$_{6-20}$ aryl, substituted or unsubstituted C$_{2-20}$ heteroaryl, and a nitrile.

In still another exemplary embodiment of the present invention, the substituted C$_{6-20}$ aryl and substituted C$_{2-20}$ heteroaryl are prepared by linking one to three arbitrary carbon atoms each independently to a substituent selected from the group consisting of hydrogen, amine, hydroxyl, aldehyde, halogen, nitro, C$_{2-6}$ alkylester,

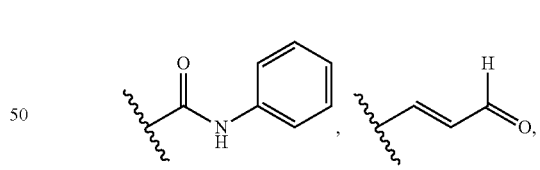

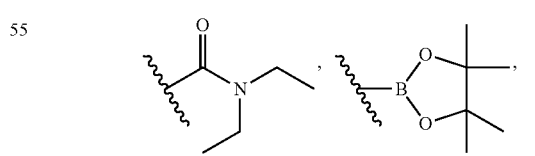

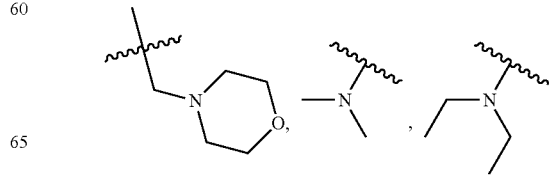

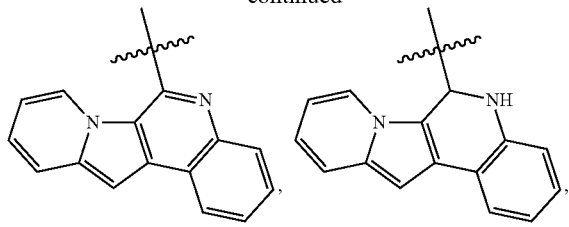

$CF_3$, COO—, $C_{1-6}$ alkyl and $C_{1-6}$ alkoxy.

In yet another exemplary embodiment of the present invention, the aryl is selected from the group consisting of phenyl, naphthyl, anthryl and biaryl.

In yet another exemplary embodiment of the present invention, the heteroaryl is selected from the group consisting of pyridyl, pyrimidyl, thiophenyl, pyrrolyl, furanyl, sulforanyl, morpholinyl, and triazolyl.

In yet another exemplary embodiment of the present invention, $R_1$ is selected from the group consisting of hydrogen, amine and $COOR_8$, $R_6$ is substituted or unsubstituted $C_{6-20}$ aryl or substituted or unsubstituted $C_{2-20}$ heteroaryl, and $R_8$ is hydrogen, $C_{1-12}$ alkyl or $C_{2-12}$ alkynyl.

In yet another exemplary embodiment of the present invention, the compound represented by Formula 1 is any one selected from the group consisting of the following compounds:

6-(4-Methoxyphenyl)indolizino(3,2-c)quinoline (Formula 2:IQ 6);
6-(Naphthalen-1-yl)indolizino[3,2-c]quinoline (Formula 3:IQ 9);
Methyl 6-(1H-pyrrol-2-yl)indolizino[3,2-c]quinoline-12-carboxylate (Formula 4:IQ 21);
Ethyl 6-(3-fluorophenyl)indolizino[3,2-c]quinoline-12-carboxylate (Formula 5:IQ 28);
Ethyl 6-(3,4-dimethoxyphenyl)indolizino[3,2-c]quinoline-12-carboxylate (Formula 6:IQ 30);
11-Methyl-6-(p-tolyl)indolizino[3,2-c]quinoline (Formula 7:IQ 15);
6-(Furan-2-yl)-11-methylindolizino[3,2-c]quinoline (Formula 8:IQ 18);
6-(3,5-Dimethoxyphenyl)indolizino[3,2-c]quinoline (Formula 9:IQ 7);
6-(3,4-Dimethoxyphenyl)-11-methylindolizino[3,2-c]quinoline (Formula 10:IQ 17);
6-(3,5-Dimethoxyphenyl)-11-methylindolizino[3,2-c]quinoline (Formula 11:IQ 16);
4-(Indolizino[3,2-c]quinolin-6-yl)-N,N-dimethylaniline (Formula 12:IQ 36);
6-(p-Tolyl)indolizino[3,2-c]quinoline (Formula 13:IQ 3);
11-methyl-6-(thiophen-2-yl)indolizino[3,2-c]quinoline (Formula 14:IQ 52);
6-(5-chlorofuran-2-yl)-11-methylindolizino[3,2-c]quinoline (Formula 15:IQ 53);
12-ethynyl-6-(4-methoxyphenyl)indolizino[3,2-c]quinoline (Formula 16:IQ 55);
4-(5-(indolizino[3,2-c]quinolin-6-yl)-2-methoxybenzyl)morpholine (Formula 17:IQ 56);
ethyl 6-(4-methoxy-3-(morpholinomethyl)phenyl) indolizino[3,2-c]quinoline-12-carboxylate (Formula 18:IQ 57);
2,6-bis(indolizino[3,2-c]quinolin-6-yl)pyridine (Formula 19:IQ 5-D);
6-(4-methoxyphenyl)-5-methylindolizino[3,2-c]quinolin-5-ium methyl sulfate (Formula 20:IQ 6-S1-Me);
5-(2-chloroethyl)-6-(4-methoxyphenyl)indolizino[3,2-c]quinolin-5-ium trifluoromethanesulfonate (Formula 21:IQ 6-S2-Cl);
6-(4-methoxyphenyl)indolizino[3,2-c]quinoline-10-carbonitrile (Formula 22:IQ 67);
6-(4-methoxyphenyl)benzo[7,8]indolizino[3,2-c]quinoline (Formula 23:IQ 77);
6-ethylbenzo[7,8]indolizino[3,2-c]quinoline (Formula 24:IQ 79);
4-(indolizino[3,2-c]quinolin-6-yl)aniline (Formula 25:IQ-B1);
4-(indolizino[3,2-c]quinolin-6-yl)phenol (Formula 26:IQ-B2);
(E)-6-(4-methoxyphenyl)-10-styrylindolizino[3,2-c]quinoline (Formula 27:IQ-B19);
(E)-10-(2-(1H-imidazol-1-yl)vinyl)-6-(4-methoxyphenyl) indolizino [3,2-c]quinoline (Formula 28:IQ-B20);
4-(6-(4-methoxyphenyl)indolizino[3,2-c]quinolin-10-yl) benzaldehyde (Formula 29:IQ-B23);
(E)-3-(6-(4-methoxyphenyl)indolizino[3,2-c]quinolin-10-yl)acrylaldehyde (Formula 30:IQ-B25);
6-(4-methoxyphenyl)indolizino[3,2-c]quinoline-10-carbaldehyde (Formula 31:IQ-B11);
(E)-6-(4-methoxystyryl)indolizino[3,2-c]quinoline (Formula 32:IQ-B12)
6,10-bis(4-methoxyphenyl)indolizino[3,2-c]quinoline (Formula 33:IQ-B26);
(E)-3-(4-(6-(4-methoxyphenyl)indolizino[3,2-c]quinolin-10-yl)phenyl)acrylaldehyde (Formula 34:IQ-B31);
4-(6-(4-methoxyphenyl)indolizino[3,2-c]quinolin-10-yl)-N,N-dimethylaniline (Formula 35:IQ-B37);
4-(6-(4-methoxyphenyl)indolizino[3,2-c]quinolin-10-yl)-N-phenylbenzamide (Formula 36:IQ-B35); and
N,N-diethyl-4-(6-(4-methoxyphenyl)indolizino[3,2-c]quinolin-10-yl)benzamide (Formula 37:IQ-B36).

In addition, the present invention provides a nucleic acid-, protein- or cell-detecting reagent including the composition.

Further, the present invention provides a nucleic acid-, protein- or cell-imaging method using the composition.

Furthermore, the present invention provides an indolizino [3,2-c]quinoline compound represented by Formula 38 or a pharmaceutically acceptable salt thereof:

[Formula 38]

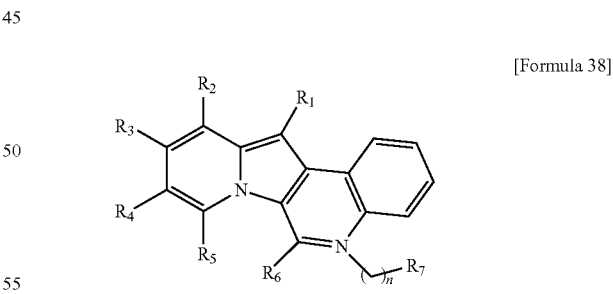

In Formula 38, $R_1$ is hydrogen, $C_{2-12}$ alkynyl or amine, $R_2$ and $R_3$ are bound with each other to form an aromatic ring, or each independently selected from the group consisting of hydrogen, substituted $C_{6-20}$ aryl, substituted $C_{2-12}$ alkenyl, amine, hydroxyl, aldehyde, nitrile, amide, phenoxy and boronic ester, $R_4$, $R_5$, and $R_7$ are each independently hydrogen, $R_6$ is selected from the group consisting of $C_{1-12}$ alkyl, substituted $C_{2-12}$ alkenyl,

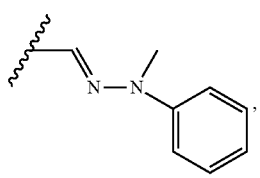 [SMILES: */C=N/N(C)c1ccccc1]

and substituted $C_{6-20}$ aryl, n is 0, 1, 2 or 3, the substituted $C_{2-12}$ alkenyl is linked to a substituent selected from the group consisting of aldehyde, substituted or unsubstituted $C_{6-20}$ aryl, substituted or unsubstituted $C_{2-20}$ heteroaryl and a nitrile, and the substituted or unsubstituted $C_{6-20}$ aryl and substituted $C_{2-20}$ heteroaryl are prepared by linking one to three arbitrary carbon atoms, each independently, to a substituent selected from the group consisting of hydrogen, amine, hydroxyl, aldehyde, halogen, nitro, $C_{2-6}$ alkylester,

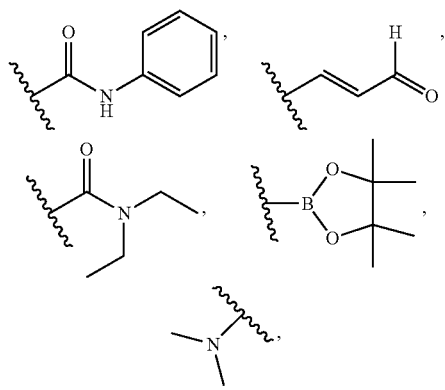

and $C_{1-6}$ alkoxy.

Advantageous Effects

An indolizino[3,2-c]quinoline compound used in a fluorescent probe of the present invention is a water-soluble fluorescent compound whose fluorescence characteristics and applications range vary greatly depending on the characteristics and position of a functional group binding to a hetero ring, can improve the shortcomings of a conventional organic fluorophore, and thus can be applied in various fields.

In addition, the fluorescent probe of the present invention binds to a nucleic acid or protein, so that it can be applied to various nucleic acid/protein function studies on its movement, drug-protein interactions, etc., and imaging technologies.

In addition, the fluorescent probe of the present invention can minimize self-quenching due to a large difference between an excitation wavelength and a fluorescence wavelength (Stokes shift).

In addition, since the fluorescent probe of the present invention has a different wavelength range of fluorescence and sensitivity to a surrounding environment depending on a substituent, it can be controlled to maximize fluorescence in an organic solvent and exhibit strong fluorescence in an aqueous solution (solvatochromic).

In addition, the fluorescent probe of the present invention can exhibit high fluorescence even in water or a buffer, have high solubility, and minimize a problem causing the aggregation of a protein.

In addition, the fluorescent probe of the present invention has excellent intracellular permeability, and is useful for imaging technologies in cells or tissue, and analysis of enzyme activity in cells.

BRIEF DESCRIPTION OF DRAWINGS

FIG. 1 shows the formulas of 5 types of compounds having high fluorescence intensity in an aqueous solution among indolizino[3,2-c]quinoline compounds of the present invention.

FIG. 2 shows absorption and emission spectra measured in water for the 5 types of compounds having high fluorescence intensity in an aqueous solution among the indolizino [3,2-c]quinoline compounds of the present invention.

FIG. 3 shows the relationship between the type of a substituent binding to a phenyl group when the $R_6$ substituent of the indolizino[3,2-c]quinoline compounds of the present invention is a phenyl group, and a fluorescence quantum yield (QY) in an aqueous solution.

FIG. 4 shows the analysis result for spectra of the 5 types of compounds having high fluorescence intensity in an aqueous solution among the indolizino[3,2-c]quinoline compounds of the present invention in various solvents (distilled water (DW), dimethyl sulfoxide (DMSO), dimethyl formamide (DMF), ethanol (EtOH), EtOH:CHCl$_3$=1: 5, and methylene chloride (MC)).

FIG. 5A shows the result of evaluating fluorescence yields of the indolizino[3,2-c]quinoline compounds of the present invention in an aqueous solution or ethanol.

FIG. 5B is a diagram showing quantum yield tendencies in an ethanol solvent for 11 types of compounds with high fluorescence intensities among the indolizino[3,2-c]quinoline compounds of the present invention.

FIGS. 5C and 5D show the results of spectrum analysis in various solvents for the indolizino[3,2-c]quinoline compounds of the present invention.

FIG. 6 shows compounds having a difference between absorption and emission wavelengths (Stokes shift) of less than 180 nm among the indolizino[3,2-c]quinoline compounds of the present invention.

FIGS. 7A to 7C show the results of evaluating photostability of the indolizino[3,2-c]quinoline compounds of the present invention in an aqueous solution (7A) or ethanol (7B), and further show the results of evaluating photostability thereof in an aqueous solution (7C) when irradiated with blue light for 2 hours.

FIGS. 8A to 8D show the results of evaluating binding characteristics of the indolizino[3,2-c]quinoline compounds of the present invention with respect to DNA, which are shown by groups including a compound group (8A) in which the peak emission wavelength shifts towards a shorter wavelength according to the change in fluorescence intensity, a compound group (8B) in which the peak emission wavelength shifts towards a longer wavelength according to the change in fluorescence intensity, a compound group that is only changed in fluorescence intensity and a compound group (8C) having no change, and FIG. 8D shows the results of confirming wavelength shifts of compounds of Formulas 7 and 8.

FIG. 9 shows the results of evaluating binding characteristics of the indolizino[3,2-c]quinoline compounds of the present invention with respect to an HSA protein.

FIG. 10 shows the results of a Job's plot to visually confirm that fluorescence is increased when the indolizino

[3,2-c]quinoline compounds of the present invention bind to HSA, and to confirm whether the compounds selectively bind to a protein one to one.

FIG. 11 visually shows the increases in fluorescence intensity of the indolizino[3,2-c]quinoline compounds of the present invention when binding to an HSA protein.

FIG. 12 shows the result of evaluating the binding characteristics of the indolizino[3,2-c]quinoline compounds of the present invention with respect to an HSA protein.

FIG. 13 shows the results of confirming whether the indolizino[3,2-c]quinoline compound of the present invention binds to a PDEδ protein through FRET phenomena.

FIG. 14 shows the results of fluorescence polarization to confirm whether the indolizino[3,2-c]quinoline compound of the present invention binds to a PDEδ protein, and confirm binding affinities ($K_d$).

FIG. 15 shows the results of a competitive binding experiment with deltarasin through fluorescence polarization to confirm whether the indolizino[3,2-c]quinoline compounds of the present invention bind to a PDEδ protein.

FIGS. 16 and 17 show the results of electrophoresis and fluorescence to confirm whether the indolizino[3,2-c]quinoline compounds of the present invention bind to a PDEδ protein.

FIGS. 18 to 22 show the results of evaluating cell permeability of the indolizino[3,2-c]quinoline compounds of the present invention, and more specifically, FIGS. 18 to 20 show the results of evaluating cell permeability in live HeLa cells, FIG. 21 shows the cell permeability for MCF7 and NIH-3T3 cells, and FIG. 22 shows cell permeability in Sf21 cells.

FIG. 23 shows compounds detected in live HeLa cells using yellow wavelength (ex 514 nm, em 519≤nm) and red wavelength (ex 561 nm, em 566≤nm) filters, among the indolizino[3,2-c]quinoline compounds of the present invention.

FIG. 24 shows cell permeability of the indolizino[3,2-c] quinoline compounds of the present invention, confirmed by co-staining with a conventional dye DAPI.

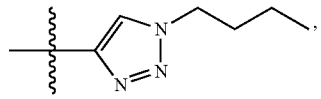

FIGS. 25A and 25C show the result of colocalization experiments with the conventional dyes DAPI, MitoTracker, or LysoTracker to confirm cell permeability of the indolizino [3,2-c]quinoline compounds of the present invention.

FIG. 25B shows the compound increased in fluorescence by light irradiation.

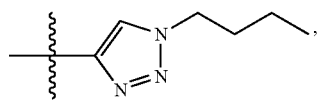

FIG. 26 show the result of comparing fluorescence stability of the indolizino[3,2-c]quinoline compounds of the present invention with that of a conventional dye such as Syto RNASelect or MitoTracker.

FIG. 27a and FIG. 27b show the result of MTT analysis to confirm the cytotoxicity of the indolizino[3,2-c]quinoline compounds of the present invention.

MODES OF THE INVENTION

The present invention provides a fluorescent probe composition, which includes an indolizino[3,2-c]quinoline compound represented by Formula 1 or a pharmaceutically acceptable salt thereof.

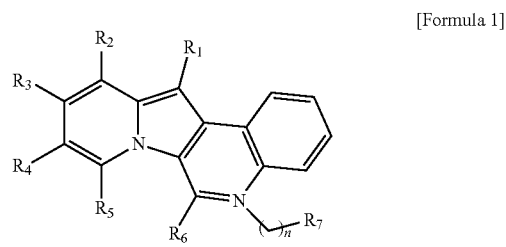

[Formula 1]

In Formula 1, $R_1$, $R_4$ and $R_5$ are each independently selected from the group consisting of hydrogen, halogen, $C_{1-12}$ alkyl, $C_{1-12}$ alkoxy, $COOR_8$, substituted or unsubstituted $C_{6-20}$ aryl, substituted or unsubstituted $C_{2-20}$ heteroaryl,

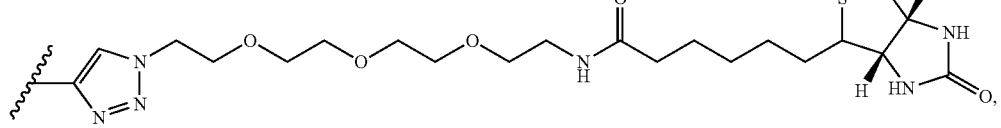

$C_{2-12}$ alkynyl, substituted $C_{2-12}$ alkenyl, amine, hydroxyl, aldehyde, nitrile, amide, phenoxy and boronic ester, $R_2$ and $R_3$ are bound with each other to form an aromatic ring, or each independently selected from the group consisting of hydrogen, halogen, $C_{1-12}$ alkyl, $C_{1-12}$ alkoxy, $COOR_8$, substituted or unsubstituted $C_{6-20}$ aryl, substituted or unsubstituted $C_{2-20}$ heteroaryl, -continued

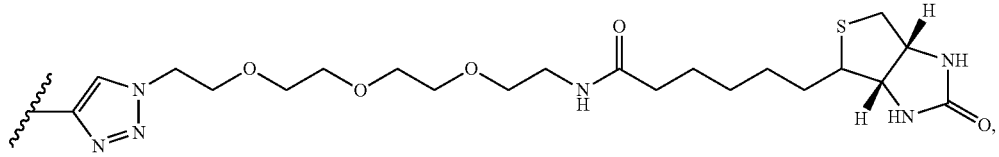

$C_{2-12}$ alkynyl, substituted $C_{2-12}$ alkenyl, amine, hydroxyl, aldehyde, nitrile, amide, phenoxy and boronic ester, $R_6$ is selected from the group consisting of $C_{1-12}$ alkyl, substituted $C_{2-12}$ alkenyl,

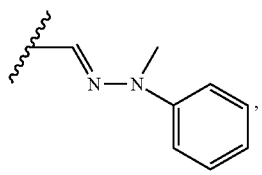 [SMILES: */C=N/N(C)c1ccccc1]

substituted or unsubstituted $C_{6-20}$ aryl, and substituted or unsubstituted $C_{2-20}$ heteroaryl, n is 0, 1, 2 or 3, $R_7$ is selected from the group consisting of hydrogen, hydroxyl, halogen and $C_{1-12}$ alkyl, and $R_8$ is selected from the group consisting of hydrogen, $C_{1-12}$ alkyl and $C_{2-12}$ alkynyl.

In Formula 1, more preferably, $R_1$, $R_4$ and $R_5$ are each independently selected from the group consisting of hydrogen, $C_{1-12}$ alkyl, COOR$_8$, and amine, $R_2$ and $R_3$ are bound with each other to form an aromatic ring, or each independently selected from the group consisting of hydrogen, aldehyde, $C_{1-12}$ alkyl, substituted $C_{2-12}$ alkenyl, substituted or unsubstituted $C_{6-20}$ aryl, substituted or unsubstituted $C_{2-20}$ heteroaryl and nitrile, $R_6$ is selected from the group consisting of $C_{1-12}$ alkyl, substituted $C_{2-12}$ alkenyl, substituted or unsubstituted $C_{6-20}$ aryl, and substituted or unsubstituted $C_{2-20}$ heteroaryl.

In the present invention, the "substituted $C_{2-12}$ alkenyl" may be linked to a substituent selected from the group consisting of an aldehyde, substituted or unsubstituted $C_{6-20}$ aryl, substituted or unsubstituted $C_{2-20}$ heteroaryl and nitrile, but the present invention is not limited thereto.

In the present invention, the "substituted $C_{6-20}$ aryl and substituted $C_{2-20}$ heteroaryl" used herein may be prepared by linking arbitrary one to three carbon atoms each independently to a substituent selected from the group consisting of hydrogen, amine, hydroxyl, aldehyde, halogen, nitro, $C_{2-6}$ alkylester,

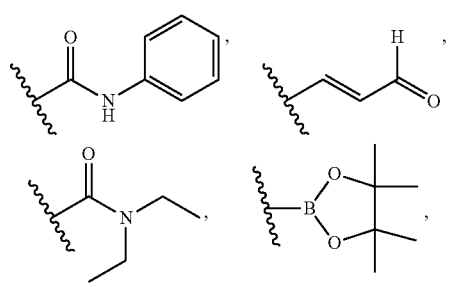

-continued

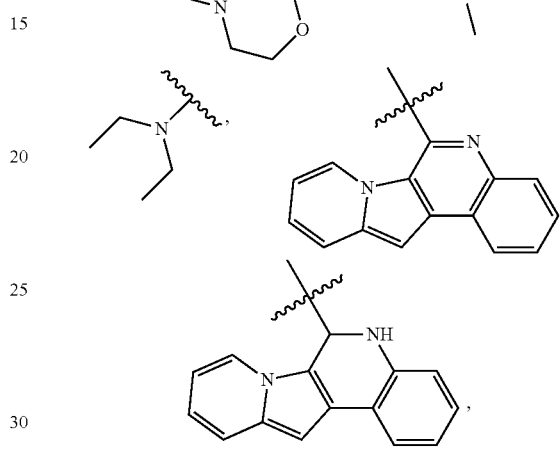

$CF_3$, COO—, $C_{1-6}$ alkyl and $C_{1-6}$ alkoxy, but the present invention is not limited thereto.

In the present invention, the "halogen" may include F, Cl, Br and I.

In the present invention, the "$C_{6-20}$ aryl" may be selected from the group consisting of phenyl, naphthyl, anthryl and biaryl, the "$C_{2-20}$ heteroaryl" may be selected from the group consisting of pyridyl, pyrimidyl, thiophenyl, pyrrolyl, furanyl, sulforanyl, morpholinyl and triazolyl, but the present invention is not limited thereto.

In the present invention, $R_1$ may be hydrogen, amine or COOR$_8$, $R_6$ may be substituted or unsubstituted $C_{6-20}$ aryl, or substituted or unsubstituted $C_{2-20}$ heteroaryl, $R_8$ may be selected from the group consisting of hydrogen, $C_{1-12}$ alkyl and $C_{2-12}$ alkynyl, but the present invention is not limited thereto.

In addition, the "$C_{1-12}$ alkyl" may be linear or branched alkyl, and specifically, is selected from the group consisting of methyl, ethyl, normal-propyl, isopropyl, normal-butyl, isobutyl, tert-butyl, normal-hexyl and isohexyl, but the present invention is not limited thereto.

In the present invention, the "$C_{1-12}$ alkoxy group" may be selected from the group consisting of methoxy, ethoxy, propoxy, butoxy, and pentoxy, but the present invention is not limited thereto.

In the present invention, the "probe" may be manufactured in the form of an oligonucleotide probe, a double-stranded DNA probe, or an RNA probe, and the selection of a suitable probe and hybridization conditions may be modified based on those known in the art. In addition, the probe may be an imaging probe, but the present invention is not limited thereto.

In the present invention, the compound of Formula 1 or pharmaceutically acceptable salt thereof may be any one or two or more selected from the group consisting of, for example, Formulas 2 to 37 listed in Table 1 below, but the present invention is not limited thereto.

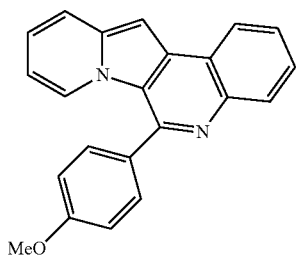 [SMILES: COc1ccc(-c2nc3ccccc3c3cc4ccccn4c23)cc1]
[Formula 2:IQ 6]
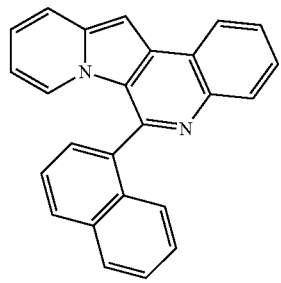 [SMILES: c1ccc2c(-c3nc4ccccc4c4cc5ccccn5c34)cccc2c1]
[Formula 3:IQ 9]
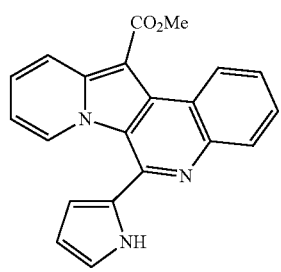 [SMILES: COC(=O)c1c2c3ccccc3nc(-c3ccc[nH]3)c2n2ccccc12]
[Formula 4:IQ 21]
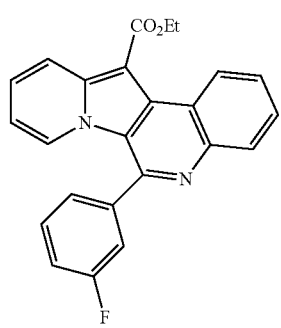 [SMILES: CCOC(=O)c1c2c3ccccc3nc(-c3cccc(F)c3)c2n2ccccc12]
[Formula 5: IQ 28]
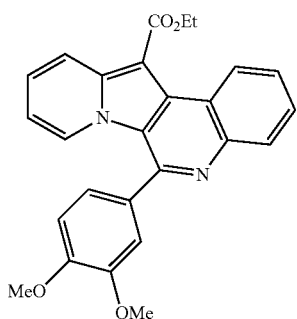 [SMILES: CCOC(=O)c1c2c3ccccc3nc(-c3ccc(OC)c(OC)c3)c2n2ccccc12]
[Formula 6:IQ 30]

-continued
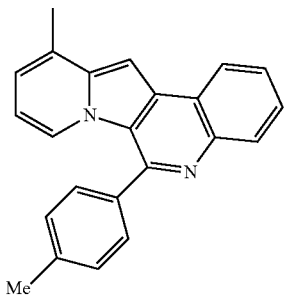 [SMILES: Cc1ccc(-c2nc3ccccc3c3cc4c(C)cccn4c23)cc1]
[Formula 7:IQ 15]
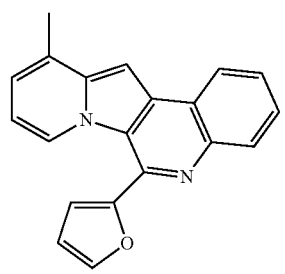 [SMILES: Cc1cccn2c1cc1c3ccccc3nc(-c3ccco3)c12]
[Formula 8:IQ 18]
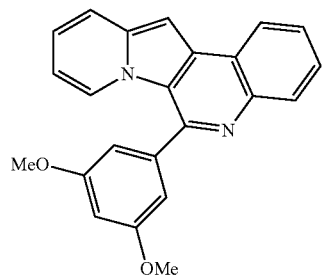 [SMILES: COc1cc(OC)cc(-c2nc3ccccc3c3cc4ccccn4c23)c1]
[Formula 9:IQ 7]
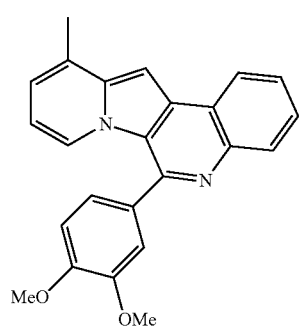 [SMILES: COc1ccc(-c2nc3ccccc3c3cc4c(C)cccn4c23)cc1OC]
[Formula 10:IQ 17]
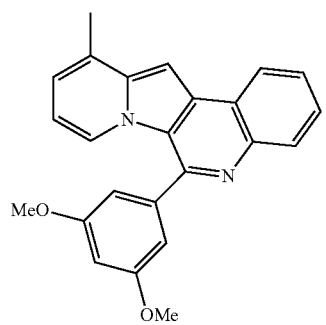 [SMILES: COc1cc(OC)cc(-c2nc3ccccc3c3cc4c(C)cccn4c23)c1]
[Formula 11:IQ 16]

-continued
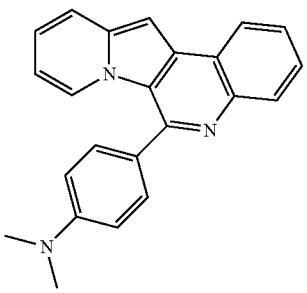 [SMILES: CN(C)c1ccc(-c2nc3ccccc3c3cc4ccccn4c23)cc1]
[Formula 12:IQ 36]
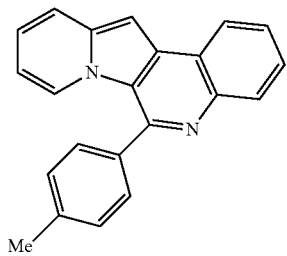 [SMILES: Cc1ccc(-c2nc3ccccc3c3cc4ccccn4c23)cc1]
[Formula 13:IQ 3]
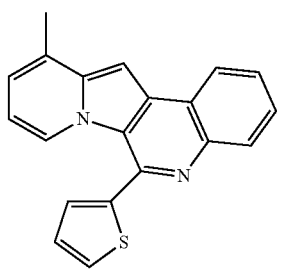
[Formula 14:IQ 52]
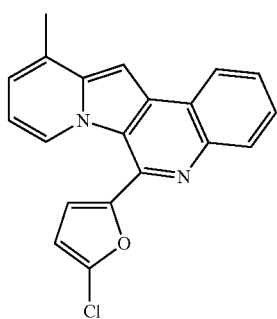 [SMILES: Cc1cccn2c1cc1c3ccccc3nc(-c3ccc(Cl)o3)c12]
[Formula 15:IQ 53]
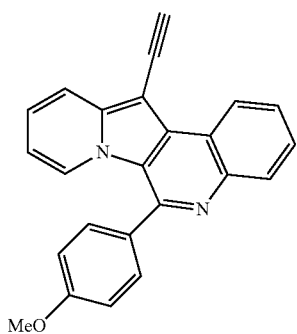 [SMILES: C#Cc1c2c3ccccc3nc(-c3ccc(OC)cc3)c2n2ccccc12]
[Formula 16:IQ 55]

-continued
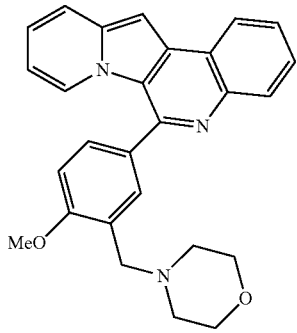 [SMILES: COc1ccc(-c2nc3ccccc3c3cc4ccccn4c23)cc1CN1CCOCC1]
[Formula 17:IQ 56]
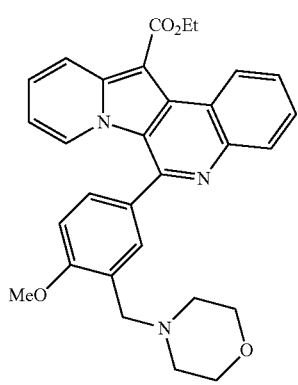 [SMILES: CCOC(=O)c1c2c3ccccc3nc(-c3ccc(OC)c(CN4CCOCC4)c3)c2n2ccccc12]
[Formula 18:IQ 57]
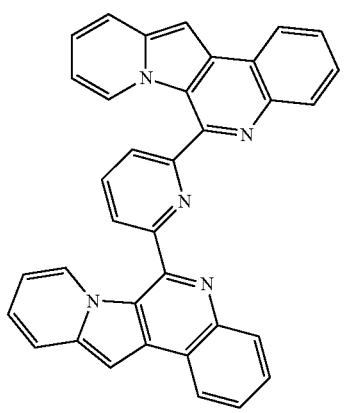 [SMILES: c1cc(-c2nc3ccccc3c3cc4ccccn4c23)nc(-c2nc3ccccc3c3cc4ccccn4c23)c1]
[Formula 19:IQ 5-D]
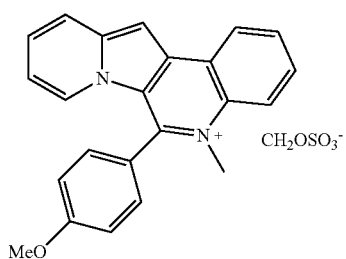
[Formula 20:IQ 6-S1-Me]
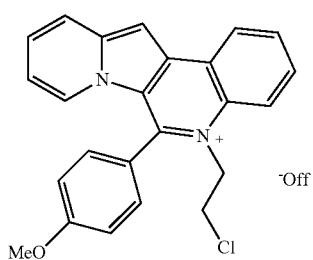
[Formula 21:IQ 6-S2-Cl]

-continued
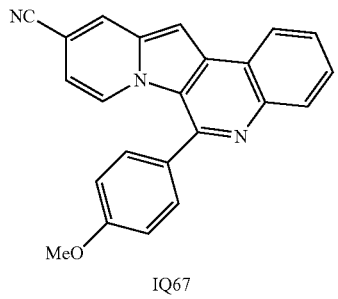
[Formula 22:IQ 67]
IQ67
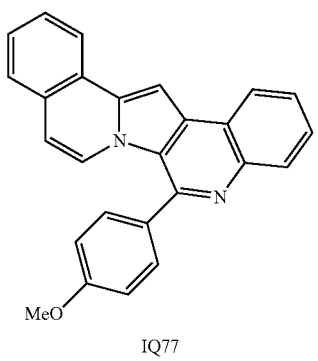
[Formula 23:IQ 77]
IQ77
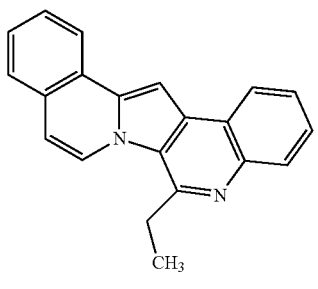
[Formula 24:IQ 79]
IQ79
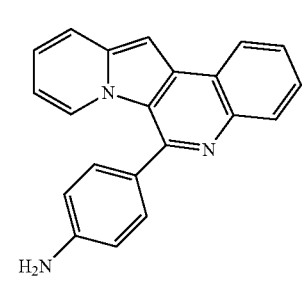
[Formula 25:IQ-B1]
IQ-B1
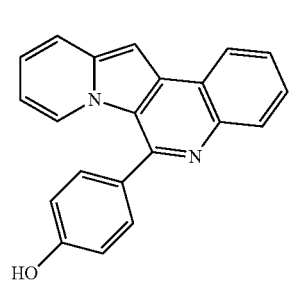
[Formula 26:IQ-B2]
IQ-B2

-continued
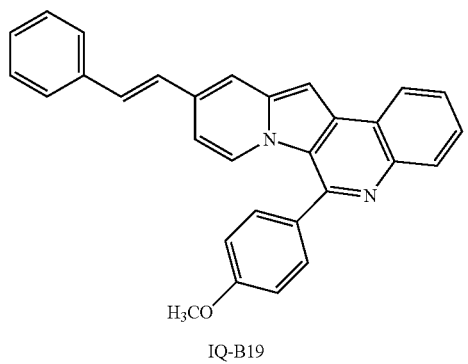 [SMILES: COc1ccc(-c2nc3ccccc3c3cc4cc(/C=C/c5ccccc5)ccn4c23)cc1]
[Formula 27:IQ-B19]
IQ-B19
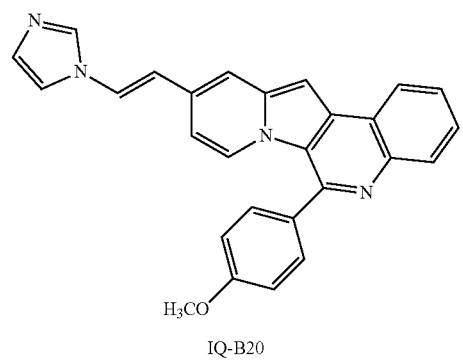 [SMILES: COc1ccc(-c2nc3ccccc3c3cc4cc(/C=C/n5ccnc5)ccn4c23)cc1]
[Formula 28:IQ-B20]
IQ-B20
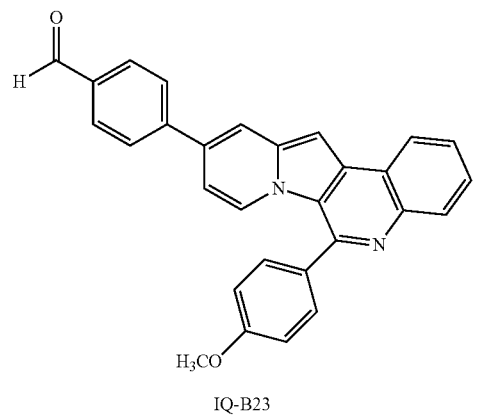 [SMILES: COc1ccc(-c2nc3ccccc3c3cc4cc(-c5ccc(C=O)cc5)ccn4c23)cc1]
[Formula 29:IQ-B23]
IQ-B23
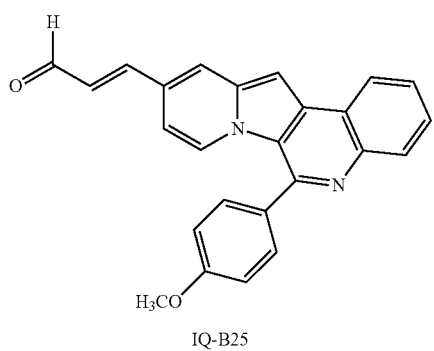 [SMILES: COc1ccc(-c2nc3ccccc3c3cc4cc(/C=C/C=O)ccn4c23)cc1]
[Formula 30:IQ-B25]
IQ-B25

-continued
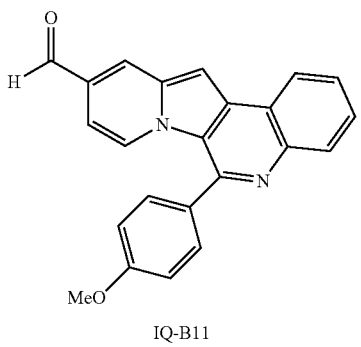 [SMILES: COc1ccc(-c2nc3ccccc3c3cc4cc(C=O)ccn4c23)cc1]
[Formula 31: IQ-B11]
IQ-B11
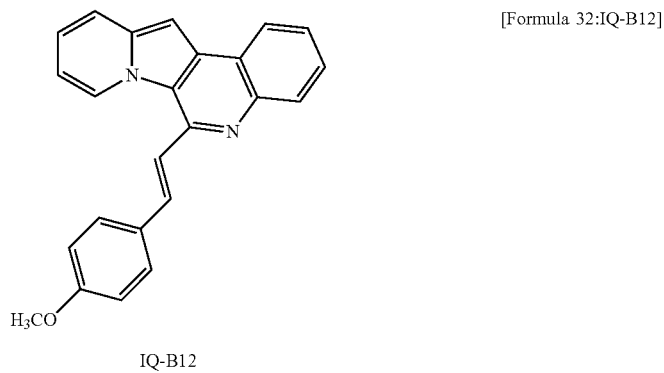
[Formula 32: IQ-B12]
IQ-B12
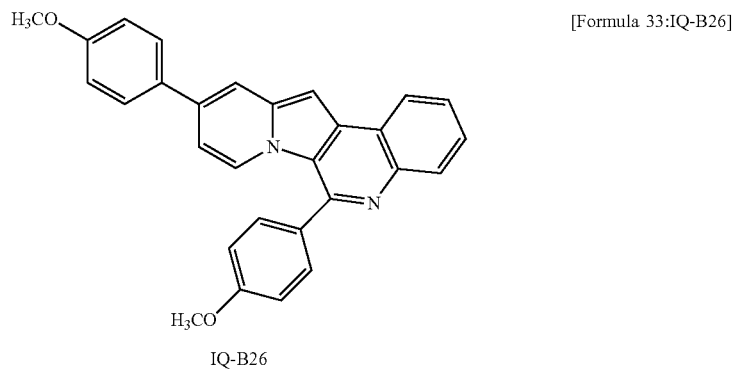
[Formula 33: IQ-B26]
IQ-B26
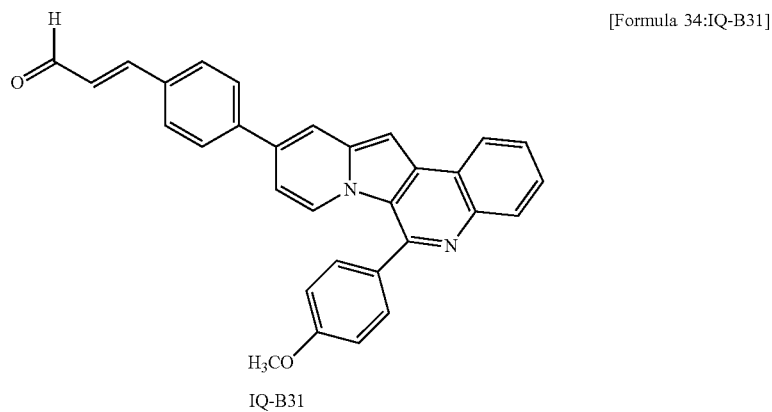
[Formula 34: IQ-B31]
IQ-B31

[Formula 35:IQ-B37]

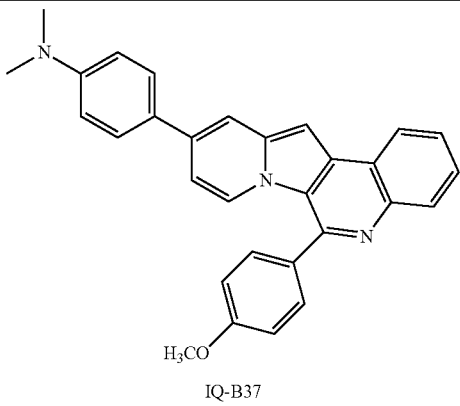

IQ-B37

[Formula 36:IQ-B35]

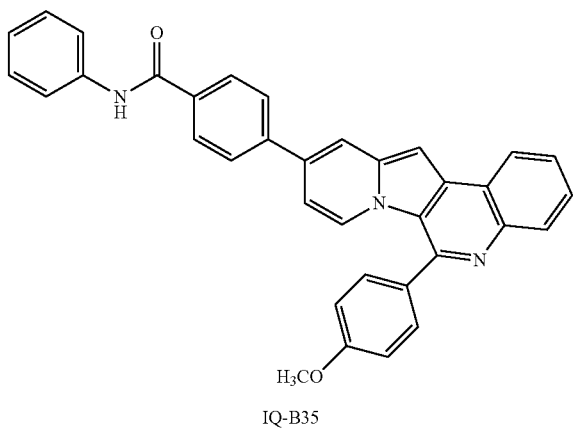 [SMILES: COc1ccc(-c2nc3ccccc3c3cc4cc(-c5ccc(C(=O)Nc6ccccc6)cc5)ccn4c23)cc1]

IQ-B35

[Formula 37:IQ-B36]

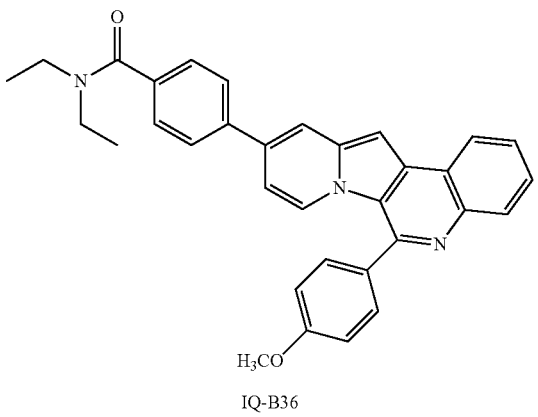 [SMILES: CCN(CC)C(=O)c1ccc(-c2ccn3c(c2)cc2c4ccccc4nc(-c4ccc(OC)cc4)c23)cc1]

IQ-B36

The term "pharmaceutically acceptable" used herein refers to a compound or composition that is suitable to be used in contact with a subject's (e.g., a human) tissue due to a reasonable benefit/risk ratio without excessive toxicity, irritation, allergic reactions, or other problems or complications, and included within the scope of sound medical judgment.

The term "salt" used herein is an acid addition salt formed by a pharmaceutically acceptable free acid. The acid addition salt is obtained from inorganic acids such as hydrochloric acid, nitric acid, phosphoric acid, sulfuric acid, hydrogen bromide, hydrogen iodide, nitride and phosphorous acid, and non-toxic organic acids such as aliphatic mono and dicarboxylates, phenyl-substituted alkanoates, hydroxyl alkanoates and alkandioates, aromatic acids, aliphatic and aromatic sulfonic acids. Such pharmaceutically non-toxic salts include sulfates, pyrosulfates, bisulfates, sulfites, bisulfites, nitrates, phosphates, monohydrogen phosphates, dihydrogen phosphates, metaphosphates, pyrophosphate chlorides, bromides, iodides, fluorides, acetates, propionates, decanoates, caprylates, acrylatse, formates, isobutyrates, caprates, heptanoates, propiolates, oxalates, malonates, succinates, suberates, sebacates, fumarates, maleates, butyne-1,4-dioates, hexane-1,6-dioates, benzoates, chlorobenzoates, methylbenzoates, dinitrobenzoates, hydroxylbenzoates, methoxybenzoate, phthalates, terephthalates, benzenesulfonates, toluenesulfonates, chlorobenzenesulfonates, xylenesulfonates, phenylacetates, phenylpropionates, phenylburyrates, citrates, lactates, β-hydroxylbutyrates, glycolates, malates, tartrates, methanesulfonates, propanesulfonates, naphthalene-1-sulfonates, naphthalene-2-sulfonates, or mandelates.

The acid addition salt according to the present invention may be prepared by a conventional method, for example, dissolving the compound represented by Formula 1 in an excessive acid aqueous solution, and precipitating the resulting salt using a water-miscible organic solvent, for example, methanol, ethanol, acetone or acetonitrile. In addition, the acid addition salt according to the present invention may be prepared by evaporating a solvent or an excessive acid from this mixture, and then dehydrating the resulting mixture or suction-filtrating a precipitated salt.

In addition, the pharmaceutically acceptable metal salt may be prepared using a base. An alkali metal or alkali earth metal salt may be obtained by, for example, dissolving a compound in an excessive amount of an alkali metal hydroxide or alkali earth metal hydroxide solution, filtering an insoluble compound salt, and dehydrating the remaining solution through evaporation. Here, a sodium, potassium or calcium salt is pharmaceutically appropriate for the metal salt. Also, a silver salt corresponding to the metal salt is obtained by a reaction between an alkali metal or alkali earth metal salt and a suitable silver salt (e.g., silver nitrate).

In the present invention, the compound represented by Formula 1 may be prepared by reacting a compound represented by Formula A below with an aldehyde in the presence of a catalyst.

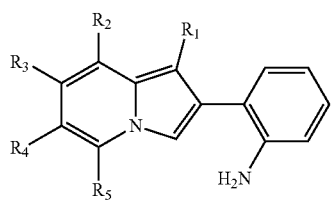

[Formula A]

In Formulas A, $R_1$, $R_2$, $R_3$, $R_4$ and $R_5$ are defined as above.

In the present invention, the catalyst may be any one selected from the group consisting of $FeCl_3$, $AlCl_3$, $BiCl_3$, $InCl_3$, p-toluenesulfonic acid (PTSA) and pyridinium p-toluenesulfonic acid (PPTS), and particularly, $FeCl_3$ is preferable because a high yield can be produced without producing a byproduct.

In addition, the catalyst may be contained at 0.1 to 0.3 equivalent, and when the content of the catalyst is less than 0.1 equivalent, the catalyst content is too small and thus reactivity is low, and when the content of the catalyst is more than 0.3 equivalent, the reactivity is reduced, which is not preferable.

Meanwhile, the reaction may be performed at 20 to 80° C. in the presence of a solvent selected from the group consisting of methylenechloride, N,N-dimethylformamide and tetrahydrofuran, and particularly, the reaction is preferably performed at 40 to 80° C. in the presence of a dichloromethane solvent to improve reaction yield.

In the present invention, the aldehyde may be selected from $C_{1-12}$ alkylaldehyde, arylaldehyde and heteroarylaldehyde, but the present invention is not limited thereto. Specific examples of the aldehyde may include 4-bromobenzaldehyde, 4-fluorobenzaldehyde, 3-fluorobenzaldehyde, 4-chlorobenzaldehyde, 3-chlorobenzaldehyde, 4-nitrobenzaldehyde, benzaldehyde, 4-methoxybenzaldehyde, 3-methoxybenzaldehyde, 4-methylbenzaldehyde, 3,5-dimethoxybenzaldehyde, 3,4-dimethoxybenzaldehyde, 1-naphthylaldehyde, 2-naphthylaldehyde, picolinaldehyde, 5-bromothiopene-2-carbaldehyde, 5-chlorothiophene-2-carbaldehyde, furan-2-carbaldehyde or 1H-pyrrol-2-carbaldehyde, but the present invention is not limited thereto.

Meanwhile, the present invention provides a nucleic acid-, protein- or cell-detecting reagent, which includes the composition.

There is no limitation to a material labeled with a fluorescent probe of the present invention, which includes, for example, a protein such as an antibody, an enzyme, a hormone, a receptor, an antigen, a nucleic acid, a natural drug, viral particles, bacterial particles, or cells, and is preferably, a nucleic acid, an antibody, an enzyme, a hormone or a receptor, or cells such as blood cells, tissue cells or bacterial cells.

In addition, the present invention provides a nucleic acid-, protein- or cell-imaging method using the composition.

In addition, the present invention provides an indolizino[3,2-c]quinoline compound represented by Formula 38 below, or a pharmaceutically acceptable salt thereof:

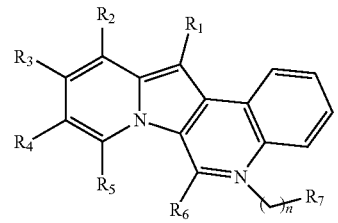

[Formula 38]

In Formula 38, $R_1$ is hydrogen, $C_{2-12}$ alkynyl or amine, $R_2$ and $R_3$ are bound with each other to form an aromatic ring, or each independently selected from the group consisting of hydrogen, substituted $C_{6-20}$ aryl, substituted $C_{2-12}$ alkenyl, amine, hydroxyl, aldehyde, nitrile, amide, phenoxy and boronic ester, $R_4$, $R_5$, and $R_7$ are each independently hydrogen, $R_6$ is selected from the group consisting of $C_{1-12}$ alkyl, substituted $C_{2-12}$ alkenyl,

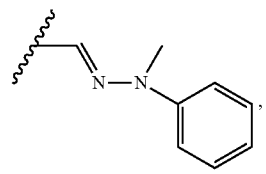

and substituted $C_{6-20}$ aryl, n is 0, 1, 2 or 3, the substituted $C_{2-12}$ alkenyl is linked to a substituent selected from the group consisting of aldehyde, substituted or unsubstituted $C_{6-20}$ aryl, substituted or unsubstituted $C_{2-20}$ heteroaryl and a nitrile, and the substituted or unsubstituted $C_{6-20}$ aryl and substituted $C_{2-20}$ heteroaryl are prepared by linking one to three arbitrary carbon atoms each independently to a substituent selected from the group consisting of hydrogen, amine, hydroxyl, aldehyde, halogen, nitro, $C_{2-6}$ alkylester,

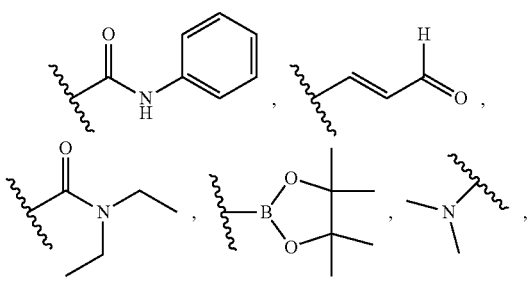

and $C_{1-6}$ alkoxy.

The fluorescent probe of the present invention may be applied in imaging by detecting fluorescence after a specimen is treated with the fluorescent probe. For example, fluorescence may be detected by adding the fluorescent probe dissolved in a polar organic solvent such as dismethylsulfoxide (DMSO) to a buffer solution and treating a specimen with the resulting solution. A concentration of the probe in a polar organic solvent is not particularly limited, but is generally, 2 µM.

In addition, the incubation time is not particularly limited, may be suitably selected depending on a specimen, but is generally approximately 5 minutes to 1 hour. An incubation temperature is not particularly limited, may be suitably selected for each specimen, generally, 0 to 40° C., and when the specimen is tissue or cells, the temperature is preferably suitable for the incubation (e.g., for human-derived cells or tissue, 37° C.).

In addition, fluorescence may be measured using a commercially available spectrofluorometer, and the position or characteristic of an enzyme in cells may be observed using a fluorescence microscope or a laser scanning confocal fluorescence microscope. In addition, a specimen is not particularly limited, and may be any one used to measure enzyme activity included therein, for example, various types of cells or tissue. When the specimen is a cell or tissue, fluorescence may be detected by replacing a cell or tissue culture with the above-described fluorescent probe solution and performing incubation as described above.

Hereinafter, to help in understanding the present invention, exemplary embodiments will be disclosed. However, the following examples are merely provided to more easily understand the present invention, and the scope of the present invention is not limited to the examples.

EXAMPLES

Example 1: Experimental Methods 1-1. Chromatography

Flash chromatography was performed with silica gel using hexene, ethylacetate and dichloromethane as an eluent, and all reaction solutions were monitored by thin film chromatography (0.25-mm silica plate; F-254) and visualized with UV. $^1H$ and $^{13}C$ NMR spectra were recorded using a 400 MHz NMR spectrometer, and HRMS was measured using electrospray ionization (ESI) and Q-TOF mass spectrometers.

1-2. Analysis of Optical Characteristics

Fluorescence emission spectra were obtained at 20° C. using a JASCO FP-6500 spectrofluorometer, a 10 mM stock solution prepared by dissolving an indolizino[3,2-c]quinoline compound in DMSO was diluted in a solvent. A fluorescence quantum yield was determined as a standard ($\Phi=0.86$ in water) using rhodamin 6G by a conventionally known method, and slit widths used in the fluorescence measurement were 3 nm for excitation and 5 nm for emission. Absorption spectra were recorded at room temperature using a Perkin Elmer Lamda 20 UV/VIS spectrometer.

Example 2: Synthesis of Compounds 2-1. Synthesis of 6-(4-bromophenyl)indolizino[3,2-c]quinoline (IQ 1)

0.14 mmol of a 2-(indolizine-2-yl)aniline compound, 0.17 mmol (1.2 equiv.) of 4-bromobenzaldehyde and 0.028 mmol (0.2 equiv.) of $FeCl_3$ were dissolved in 4 mL of dichloromethane to allow a reaction at 60° C. for 16 hours. After the reaction, the reaction mixture was washed with 3 mL of water, and the aqueous layer was extracted again with 3 mL of dichloromethane. An organic layer was collected, dried with magnesium sulfate, and concentrated under reduced pressure. The concentrated reaction mixture was purified by silica gel column chromatography using a solvent (hexane:ethylacetate:dichloromethane=30:1:2), thereby obtaining a desired compound.

Yellow solid, mp 205.5-205.8° C. (43.4 mg, 83%); IR (ATR) v=2921, 2852, 1630, 1480, 1354 cm$^{-1}$; $^1H$ NMR (400 MHz, $CDCl_3$) δ 8.39 (d, J=7.6 Hz, 1H), 8.23 (d, J=8.0 Hz, 1H), 7.89 (d, J=6.8 Hz, 1H), 7.76 (d, J=8.0 Hz, 2H), 7.73-7.68 (m, 1H), 7.69-7.62 (m, 2H), 7.58 (d, J=8.0 Hz, 2H), 7.31 (s, 1H), 7.07 (t, J=7.6 Hz, 1H), 6.48 (d, J=6.8 Hz, 1H); $^{13}C$ NMR (100 MHz, $CDCl_3$) δ 147.4, 143.1, 139.1, 138.9, 132.6, 131.9, 130.6, 129.7, 127.8, 126.8, 126.0, 123.7, 123.6, 122.5, 121.0, 119.5, 110.1, 92.4; HRMS (ESI) calcd for $C_{21}H_{14}BrN_2$ 373.0335 ([M+H]$^+$), found 373.0336.

2-2. Synthesis of 6-(4-nitrophenyl)indolizino[3,2-c]quinoline (IQ 2)

A desired compound was obtained by the method described in Example 2-1, except that 4-nitrobenzaldehyde was used instead of 4-bromobenzaldehyde.

Orange solid, mp 246.3-246.5° C. (26.1 mg, 55%); IR (ATR) v=2921, 2850, 1632, 1596, 1505, 1434, 1343 cm$^{-1}$; $^1H$ NMR (400 MHz, $CDCl_3$) δ 8.47 (d, J=8.5 Hz, 2H), 8.39 (d, J=7.6 Hz, 1H), 8.22 (d, J=8.0 Hz, 1H), 7.89 (d, J=8.5 Hz, 2H), 7.77 (d, J=6.8 Hz, 1H), 7.72 (t, J=7.6 Hz, 1H), 7.69-7.62 (m, 2H), 7.31 (s, 1H), 7.08 (dd, J=7.2, 8.4 Hz, 1H), 6.48 (t, J=6.8 Hz, 1H); $^{13}C$ NMR (100 MHz, $CDCl_3$) δ 148.4, 146.4, 145.9, 143.0, 139.2, 132.0, 130.2, 129.7, 128.0, 126.5, 126.4, 124.6, 123.8, 123.7, 122.6, 120.6, 119.7, 110.4, 92.7; HRMS (ESI) calcd for $C_{21}H_{14}N_3O_2$ 340.1081 ([M+H]$^+$), found 340.1080.

2-3. Synthesis of 6-(p-tolyl)indolizino[3,2-c]quinoline (IQ 3:Formula 13)

A desired compound was obtained by the method described in Example 2-1, except that 4-methylbenzaldehyde was used instead of 4-bromobenzaldehyde.

Yellow solid, mp 85.3-86.0° C. (22.9 mg, 53%); IR (ATR) v=2980, 1631, 1492, 1435, 1372 cm$^{-1}$; $^1H$ NMR (400 MHz, $CDCl_3$) δ 8.37 (d, J=8.4 Hz, 1H), 8.25 (d, J=8.4 Hz, 1H), 7.89 (d, J=7.2 Hz, 1H), 7.68 (t, J=7.6 Hz, 1H), 7.62 (d, J=8.4 Hz, 2H), 7.56 (d, J=7.2 Hz, 2H), 7.41 (d, J=7.6 Hz, 2H), 7.27

(s, 1H), 7.02 (t, J=8.8 Hz, 1H), 6.40 (t, J=6.8 Hz, 1H), 2.51 (s, 3H); $^{13}$C NMR (100 MHz, CDCl$_3$) δ 148.9, 143.2, 139.1, 138.9, 137.0, 131.6, 130.0, 129.7, 128.7, 127.5, 127.0, 125.7, 123.6, 123.4, 122.5, 121.3, 119.3, 109.7, 92.2, 21.7; HRMS (ESI) calcd for C$_{22}$H$_{17}$N$_2$ 309.1386 ([M+H]$^+$), found 309.1388.

2-4. Synthesis of 6-phenylindolizino[3,2-c]quinoline (IQ 4)

A desired compound was obtained by the method described in Example 2-1, except that benzaldehyde was used instead of 4-bromobenzaldehyde.

Yellow solid, mp 141.9-142.8° C. (25.5 mg, 62%); IR (ATR) v=3046, 2941, 1631, 1487, 1353 cm$^{-1}$; $^1$H NMR (400 MHz, CDCl$_3$) δ 8.36 (d, J=8.0 Hz, 1H), 8.26 (d, J=8.4 Hz, 1H), 7.78 (d, J=7.2 Hz, 1H), 7.70 (d, J=6.8 Hz, 1H), 7.66 (dd, J=1.2, 8.0 Hz, 2H), 7.45-7.53 (m, 5H), 7.26 (s, 1H), 7.01 (dd, J=7.2, 8.8 Hz, 1H), 6.38 (t, J=6.4 Hz, 1H); $^{13}$C NMR (100 MHz, CDCl$_3$) δ 148.8, 143.2, 140.0, 139.0, 131.7, 129.7, 129.4, 129.3, 128.8, 127.6, 126.9, 125.8, 123.6, 123.5, 122.5, 121.2, 119.3, 109.8, 92.2; HRMS (ESI) calcd for C$_{21}$H$_{15}$N$_2$ 295.1230 ([M+H]$^+$), found 295.1225.

2-5. Synthesis of 6-(pyridin-2-yl)indolizino[3,2-c]quinoline (IQ 5)

A desired compound was obtained by the method described in Example 2-1, except that picolinaldehyde was used instead of 4-bromobenzaldehyde.

Yellow solid, mp 177.9-178.3° C. (11.6 mg, 28%); IR (ATR) v=3006, 2922, 2852, 1629, 1560, 1434, 1355, 744 cm$^{-1}$; $^1$H NMR (400 MHz, CDCl$_3$) δ 8.84 (d, J=4.4 Hz, 1H), 8.40 (d, J=8.0 Hz, 1H), 8.25 (d, J=8.0 Hz, 1H), 8.12 (d, J=7.2 Hz, 1H), 8.07 (d, J=7.2 Hz, 1H), 8.02 (t, J=7.2 Hz, 1H), 7.70 (t, J=7.6 Hz, 1H), 7.67-7.60 (m, 2H), 7.52 (t, J=6.0 Hz, 1H), 7.31 (s, 1H), 7.07 (t, J=7.6 Hz, 1H), 6.49 (t, J=6.8 Hz, 1H); $^{13}$C NMR (100 MHz, CDCl$_3$) δ 158.5, 149.2, 147.0, 143.0, 139.2, 137.9, 132.4, 129.7, 128.1, 127.6, 126.2, 125.3, 124.2, 123.72, 123.66, 122.9, 121.1, 119.2, 109.7, 92.4; HRMS (ESI) calcd for C$_{20}$H$_{14}$N$_3$ 296.1182 ([M+H]$^+$), found 296.1182.

2-6. Synthesis of 6-(4-methoxyphenyl)indolizino[3,2-c]quinoline (IQ 6:Formula 2)

A desired compound was obtained by the method described in Example 2-1, except that 4-methoxybenzaldehyde was used instead of 4-bromobenzaldehyde.

Yellow solid, mp 164.3-164.7° C. (29.5 mg, 65%); IR (ATR) v=3055, 2998, 1606, 1494, 1440, 1374, 1355, 1024 cm$^{-1}$; $^1$H NMR (400 MHz, CDCl$_3$) δ 8.38 (d, J=7.6 Hz, 1H), 8.24 (d, J=8.0 Hz, 1H), 7.94 (d, J=7.2 Hz, 1H), 7.69 (t, J=7.2 Hz, 1H), 7.66-7.56 (m, 4H), 7.28 (s, 1H), 7.14 (d, J=8.4 Hz, 2H), 7.04 (t, J=7.2 Hz, 1H), 6.43 (t, J=6.4 Hz, 1H), 3.94 (s, 3H); $^{13}$C NMR (100 MHz, CDCl$_3$) δ 160.4, 148.5, 143.2, 138.9, 132.3, 131.6, 130.1, 129.6, 127.5, 126.9, 125.6, 123.6, 123.4, 122.4, 121.4, 119.3, 114.8, 109.7, 92.1, 55.6; HRMS (ESI) calcd for C$_{22}$H$_{17}$N$_2$O 325.1335 ([M+H]$^+$), found 325.1338.

2-7. Synthesis of 6-(3,5-dimethoxyphenyl)indolizino[3,2-c]quinoline (IQ 7: Formula 9)

A desired compound was obtained by the method described in Example 2-1, except that 3,5-dimethoxybenzaldehyde was used instead of 4-bromobenzaldehyde.

Yellow solid, mp 139.7-140.4° C. (35.2 mg, 71%); IR (ATR) v=3062, 2838, 1592, 1452, 1353, 1149 cm$^{-1}$; $^1$H NMR (400 MHz, CDCl$_3$) δ 8.39 (d, J=7.6 Hz, 1H), 8.26 (d, J=8.4 Hz, 1H), 7.88 (d, J=7.2 Hz, 1H), 7.70 (t, J=7.2 Hz, 1H), 7.67-7.60 (m, 2H), 7.30 (s, 1H), 7.06 (dd, J=6.4, 8.8 Hz, 1H), 6.79 (d, J=2.0 Hz, 2H), 6.69-6.64 (m, 1H), 6.47 (t, J=6.8 Hz, 1H), 3.85 (s, 6H); $^{13}$C NMR (100 MHz, CDCl$_3$) δ 161.7, 148.5, 143.0, 141.7, 139.0, 131.6, 129.7, 127.6, 127.1, 125.8, 123.6, 123.6, 122.6, 120.9, 119.2, 110.0, 106.3, 101.9, 92.1, 55.7; HRMS (ESI) calcd for C$_{23}$H$_{19}$N$_2$O$_2$ 355.1441 ([M+H]$^+$), found 355.1431.

2-8. Synthesis of 6-(3,4-dimethoxyphenyl)indolizino[3,2-c]quinoline (IQ 8)

A desired compound was obtained by the method described in Example 2-1, except that 3,4-dimethoxybenzaldehyde was used instead of 4-bromobenzaldehyde.

Yellow solid, mp 91.3-92.0° C. (33.7 mg, 68%); IR (ATR) v=3053, 2933, 1602, 1493, 1450, 1352, 1135, 1022 cm$^{-1}$; $^1$H NMR (400 MHz, CDCl$_3$) δ 8.38 (d, J=8.0 Hz, 1H), 8.25 (d, J=8.4 Hz, 1H), 7.90 (d, J=7.2 Hz, 1H), 7.69 (t, J=7.6 Hz, 1H), 7.66-7.57 (m, 2H), 7.28 (s, 1H), 7.22 (dd, J=1.6, 8.4 Hz, 1H), 7.19 (s, 1H), 7.09 (d, J=8.4 Hz, 1H), 7.05 (t, J=6.8 Hz, 1H), 6.44 (t, J=6.8 Hz, 1H), 4.01 (s, 3H), 3.91 (s, 3H); $^{13}$C NMR (100 MHz, CDCl$_3$) δ 149.8, 149.7, 148.5, 143.1, 139.0, 132.4, 131.7, 129.6, 127.6, 127.1, 125.7, 123.6, 123.5, 122.5, 121.30, 121.23, 119.3, 111.9, 111.7, 109.8, 92.2, 56.24, 56.17; HRMS (ESI) calcd for C$_{23}$H$_{19}$N$_2$O$_2$ 355.1441 ([M+H]$^+$), found 355.1448.

2-9. Synthesis of 6-(naphthalen-1-yl)indolizino[3,2-c]quinoline (IQ 9: Formula 3)

A desired compound was obtained by the method described in Example 2-1, except that 1-naphthaldehyde was used instead of 4-bromobenzaldehyde.

Yellow solid, mp 205.6-206.3° C. (40.0 mg, 83%); IR (ATR) v=3051, 2929, 1631, 1493, 760 cm$^{-1}$; $^1$H NMR (400 MHz, CDCl$_3$) δ 8.45 (d, J=7.6 Hz, 1H), 8.30 (d, J=8.0 Hz, 1H), 8.08 (d, J=7.2 Hz, 1H), 7.98 (d, J=8.4 Hz, 1H), 7.76-7.65 (m, 4H), 7.63 (d, J=9.0 Hz, 1H), 7.49 (t, J=7.6 Hz, 1H), 7.40 (d, J=8.4 Hz, 1H), 7.33 (s, 1H), 7.31-7.22 (m, 1H), 7.17 (d, J=7.2 Hz, 1H), 6.94 (t, J=7.6 Hz, 1H), 6.14 (t, J=6.8 Hz, 1H); $^{13}$C NMR (100 MHz, CDCl$_3$) δ 147.4, 143.4, 139.0, 137.0, 134.0, 131.6, 131.4, 129.8, 129.6, 128.6, 127.7, 127.3, 126.9, 126.6, 126.5, 126.1, 125.9, 125.3, 123.7, 123.5, 122.7, 122.3, 119.1, 110.0, 92.1; HRMS (ESI) calcd for C$_{25}$H$_{17}$N$_2$ 345.1386 ([M+H]$^+$), found 345.1383.

2-10. Synthesis of 6-(naphthalen-2-yl)indolizino[3,2-c]quinoline (IQ 10)

A desired compound was obtained by the method described in Example 2-1, except that 2-naphthaldehyde was used instead of 4-bromobenzaldehyde.

Yellow solid, mp 205.6-206.2° C. (22.7 mg, 47%); IR (ATR) v=3047, 2920, 1632, 1496, 1352, 745 cm$^{-1}$; $^1$H NMR (400 MHz, CDCl$_3$) δ 8.41 (d, J=7.6 Hz, 1H), 8.28 (d, J=8.0 Hz, 1H), 8.21 (s, 1H), 8.08 (d, J=8.4 Hz, 1H), 7.99 (d, J=7.6 Hz, 1H), 7.95 (d, J=7.2 Hz, 1H), 7.84 (d, J=7.6 Hz, 1H), 7.75 (d, J=8.4 Hz, 1H), 7.71 (t, J=7.2 Hz, 1H), 7.67-7.59 (m, 3H), 7.59-7.54 (m, 1H), 7.31 (s, 1H), 7.01 (t, J=7.2 Hz, 1H), 6.32 (t, J=7.2 Hz, 1H); $^{13}$C NMR (100 MHz, CDCl$_3$) δ 143.3, 139.0, 137.4, 133.8, 133.6, 131.8, 129.7, 129.2, 128.7, 128.3, 128.1, 127.7, 127.0, 126.9, 126.8, 126.3, 125.9, 123.7, 123.5, 122.6, 121.4, 119.3, 109.9, 92.3; HRMS (ESI) calcd for $C_{25}H_{17}N_2$ 345.1386 ([M+H]$^+$), found 345.1387.

2-11. Synthesis of 6-(5-chlorothiophen-2-yl)indolizino[3,2-c]quinoline (IQ 11)

A desired compound was obtained by the method described in Example 2-1, except that 5-chlorothiophene-2carbaldehyde was used instead of 4-bromobenzaldehyde.

Yellow solid, mp 161.4-161.7° C. (36.6 mg, 78%); IR (ATR) v=3041, 2937, 1632, 1561, 1493, 1352, 751 cm$^{-1}$; $^1$H NMR (400 MHz, CDCl$_3$) δ 8.34 (d, J=8.0 Hz, 2H), 8.21 (d, J=8.0 Hz, 1H), 7.69 (td, J=1.2, 6.8 Hz, 1H), 7.66-7.59 (m 2H), 7.26 (s, 1H), 7.19 (d, J=4.0 Hz, 1H), 7.11-7.04 (m, 2H), 6.57 (td, J=1.2, 6.4 Hz, 1H); $^{13}$C NMR (100 MHz, CDCl$_3$) δ 142.9, 140.5, 139.8, 139.2, 132.7, 132.1, 129.7, 127.8, 127.4, 126.82, 126.75, 126.3, 123.8, 123.6, 122.6, 121.2, 119.5, 110.2, 92.5; HRMS (ESI) calcd for $C_{19}H_{12}ClN_2S$ 335.0404 ([M+H]$^+$), found 335.0402.

2-12. Synthesis of 6-(4-bromophenyl)-11-methylindolizino[3,2-c]quinoline (IQ 12)

A desired compound was obtained by the method described in Example 2-1, except that a 2-(8-methylindolizine-2-yl)aniline compound was used instead of a 2-(indolizine-2-yl)aniline compound.

Yellow solid, mp 226.5-226.8° C. (45.0 mg, 83%); IR (ATR) v=3042, 2919, 1588, 1498, 1356 cm$^{-1}$; $^1$H NMR (400 MHz, CDCl$_3$) δ 8.42 (d, J=7.6 Hz, 1H), 8.23 (d, J=8.4 Hz, 1H), 7.80-7.72 (m, 3H), 7.70 (t, J=6.8 Hz, 1H), 7.64 (t, J=7.2 Hz, 1H), 7.57 (d, J=8.0 Hz, 2H), 7.29 (s, 1H), 6.89 (d, J=6.0 Hz, 1H), 6.43 (t, J=6.8 Hz, 1H), 2.61 (s, 3H); $^{13}$C NMR (100 MHz, CDCl$_3$) δ 147.4, 143.1, 140.1, 138.9, 132.5, 131.6, 130.7, 129.6, 128.3, 127.6, 125.9, 124.6, 123.58, 123.56, 122.6, 122.4, 110.2, 90.8, 18.8; HRMS (ESI) calcd for $C_{22}H_{16}BrN_2$ 387.0491 ([M+H]$^+$), found 387.0490.

2-13. Synthesis of 11-methyl-6-(4-nitrophenyl)indolizino[3,2-c]quinoline (IQ 13)

A desired compound was obtained by the method described in Example 2-1, except that a 2-(8-methylindolizine-2-yl)aniline compound was used instead of a 2-(indolizine-2-yl)aniline compound, and 4-nitrobenzaldehyde was used instead of 4-bromobenzaldehyde.

Yellow solid, mp 259.7-260.4° C. (35.1 mg, 71%); IR (ATR) v=3026, 2920, 1631, 1595, 1441, 1341, 1381, 1102 cm$^-$; $^1$H NMR (400 MHz, CDCl$_3$) δ 8.48 (d, J=6.8 Hz, 2H), 8.43 (d, J=7.6 Hz, 1H), 8.23 (d, J=8.0 Hz, 1H), 7.90 (d, J=6.8 Hz, 2H), 7.75-7.61 (m, 3H), 7.31 (s, 1H), 6.91 (d, J=6.4 Hz, 1H), 6.44 (t, J=6.8 Hz, 1H), 2.62 (s, 3H); $^{13}$C NMR (100 MHz, CDCl$_3$) δ 148.4, 146.4, 146.1, 143.0, 140.3, 131.8, 130.3, 129.7, 128.7, 127.9, 126.4, 124.5, 124.3, 123.7, 122.69, 122.67, 121.2, 110.6, 91.2, 18.8; HRMS (ESI) calcd for $C_{22}H_{16}N_3O_2$ 354.1237 ([M+H]$^+$), found 354.1235.

2-14. Synthesis of 6-(3-fluorophenyl)-11-methylindolizino[3,2-c]quinoline

A desired compound was obtained by the method described in Example 2-1, except that a 2-(8-methylindolizine-2-yl)aniline compound was used instead of a 2-(indolizine-2-yl)aniline compound, and 3-fluorobenzaldehyde was used instead of 4-bromobenzaldehyde.

Yellow solid, mp 162.5-163.1° C. (35.7 mg, 79%); IR (ATR) v=3013, 2918, 1626, 1491, 1435, 1349 cm$^{-1}$; $^1$H NMR (400 MHz, CDCl$_3$) δ 8.40 (d, J=8.0 Hz, 1H), 8.25 (d, J=8.4 Hz, 1H), 7.79 (d, J=7.2 Hz, 1H), 7.68 (t, J=8.4 Hz, 1H), 7.62 (t, J=7.2 Hz, 1H), 7.55 (d, J=8.0 Hz, 2H), 7.40 (d, J=8.0 Hz, 2H), 6.87-6.81 (m, 1H), 6.36 (t, J=7.2 Hz, 1H), 2.59 (s, 3H), 2.51 (s, 3H); $^{13}$C NMR (100 MHz, CDCl$_3$) δ 149.1, 143.2, 140.0, 139.0, 137.1, 131.4, 130.0, 129.7, 128.7, 128.1, 127.4, 125.6, 124.9, 123.5, 122.6, 122.2, 121.8, 109.8, 90.6, 21.7, 18.8; HRMS (ESI) calcd for $C_{23}H_{19}N_2$ 323.1543 ([M+H]$^+$), found 323.1542.

2-15. Synthesis of 11-methyl-6-(p-tolypindolizino[3,2-c]quinoline (IQ 15: Formula 7)

A desired compound was obtained by the method described in Example 2-1, except that a 2-(8-methylindolizine-2-yl)aniline compound was used instead of a 2-(indolizine-2-yl)aniline compound, and 4-methylbenzaldehyde was used instead of 4-bromobenzaldehyde.

Yellow solid, mp 176.1-176.5° C. (36.6 mg, 80%); IR (ATR) v=3042, 2903, 1561, 1496, 1364, 1110 cm$^{-1}$; $^1$H NMR (400 MHz, CDCl$_3$) δ 8.39 (d, J=8.0 Hz, 1H), 8.24 (d, J=8.0 Hz, 1H), 7.73-7.66 (m, 2H), 7.62 (t, J=7.2 Hz, 1H), 7.60-7.53 (m, 1H), 7.43 (d, J=8.8 Hz, 1H), 7.40 (d, J=8.8 Hz, 1H), 7.28 (dd, J=1.6, 8.4 Hz, 1H), 7.25 (s, 1H), 6.85 (d, J=6.8 Hz, 1H), 6.38 (t, J=7.2 Hz, 1H), 2.58 (s, 3H); $^{13}$C NMR (100 MHz, CDCl$_3$) δ 163.3 (d, JC,F=247.0 Hz), 147.2, 142.5 (d, JC,F=287.0 Hz), 142.0 (d, JC,F=8.0 Hz), 131.6, 131.02 (d, JC,F=8.0 Hz), 129.6, 128.3, 127.6, 126.0, 124.7, 124.6, 124.5, 123.6, 122.6, 122.5, 121.4, 116.3 (d, JC,F=6.0 Hz), 116.1 (d, JC,F=7.0 Hz), 110.2, 90.8, 18.8; HRMS (ESI) calcd for $C_{22}H_{16}FN_2$ 327.1292 ([M+H]$^+$), found 327.1292.

2-16. Synthesis of 6-(3,5-dimethoxyphenyl)-11-methylindolizino[3,2-c]quinoline (IQ 16: Formula 11)

A desired compound was obtained by the method described in Example 2-1, except that a 2-(8-methylindolizine-2-yl)aniline compound was used instead of a 2-(indolizine-2-yl)aniline compound, and 3,5-dimethoxybenzaldehyde was used instead of 4-bromobenzaldehyde.

Yellow solid, mp 185.8-186.4° C. (39.7 mg, 77%); IR (ATR) v=2933, 2836, 1596, 1495, 1453, 1365, 1193, 1149 cm$^{-1}$; $^1$H NMR (400 MHz, CDCl$_3$) δ 8.40 (d, J=7.6 Hz, 1H), 8.26 (d, J=8.4 Hz, 1H), 7.77 (d, J=6.8 Hz, 1H), 7.69 (t, J=6.8 Hz, 1H), 7.62 (t, J=8.0 Hz, 1H),7.62 (s, 1H), 6.86 (d, J=5.2 Hz, 1H), 6.78 (s, 2H), 6.66 (s, 1H), 6.41 (t, J=7.2 Hz, 1H), 3.83 (s, 6H), 2.58 (s, 3H); $^{13}$C NMR (100 MHz, CDCl$_3$) δ 161.6, 148.6, 143.0, 141.7, 140.0, 131.4, 129.7, 128.0, 127.5, 125.8, 125.0, 123.6, 122.6, 122.4, 121.4, 110.1, 106.4, 101.9, 90.6, 55.7, 18.8; HRMS (ESI) calcd for $C_{24}H_{21}N_2O_2$ 369.1598 ([M+H]$^+$), found 369.1595.

2-17. Synthesis of 6-(3,4-dimethoxyphenyl)-11-methylindolizino[3,2-c]quinoline (IQ 17: Formula 10)

A desired compound was obtained by the method described in Example 2-1, except that a 2-(8-methylindolizine-2-yl)aniline compound was used instead of a 2-(indolizine-2-yl)aniline compound, and 3,4-dimethoxybenzaldehyde was used instead of 4-bromobenzaldehyde.

Yellow solid, mp 162.8-163.3° C. (35.1 mg, 68%); IR (ATR) v=2919, 2845, 1602, 1492, 1411, 1365, 1138 cm$^{-1}$; $^1$H NMR (400 MHz, CDCl$_3$) δ 8.40 (d, J=7.6 Hz, 1H), 8.25 (d, J=8.0 Hz, 1H), 7.79 (d, J=7.2 Hz, 1H), 7.69 (t, J=7.2 Hz, 1H), 7.62 (t, J=7.6 Hz, 1H), 7.27 (s, 1H), 7.22 (d, J=8.0 Hz, 1H), 7.19 (s, 1H), 7.09 (d, J=8.0 Hz, 1H), 6.86 (d, J=6.4 Hz, 1H), 6.39 (d, J=7.2 Hz, 1H), 4.01 (s, 3H), 3.90 (s, 3H), 2.59 (s, 3H); $^{13}$C NMR (100 MHz, CDCl$_3$) δ 149.8, 149.6, 148.6, 143.1, 140.0, 132.4, 131.4, 129.6, 128.1, 127.5, 125.7, 124.9, 123.5, 122.6, 122.3, 121.8, 121.3, 111.9, 111.8, 109.9, 90.7, 56.2, 56.1, 18.8; HRMS (ESI) calcd for C$_{24}$H$_{21}$N$_2$O$_2$ 369.1598 ([M+H]$^+$), found 369.1595.

2-18. Synthesis of 6-(furan-2-yl)-11-methylindolizino[3,2-c]quinoline (IQ 18: Formula 8)

A desired compound was obtained by the method described in Example 2-1, except that 2-(8-methylindolizine-2-yl)aniline compound was used instead of a 2-(indolizine-2-yl)aniline compound, and furan-2-carbaldehyde was used instead of 4-bromobenzaldehyde.

Yellow solid, mp 112.4-113.2° C. (33.0 mg, 79%); IR (ATR) v=3096, 2922, 1611, 1481, 1438, 1365, 1013 cm$^{-1}$; $^1$H NMR (400 MHz, CDCl$_3$) δ 8.35 (d, J=6.4 Hz, 1H), 8.25 (d, J=8.4 Hz, 1H), 7.84 (d, J=6.8 Hz, 1H), 7.72 (s, 1H), 7.68 (t, J=6.8 Hz, 1H), 7.61 (t, J=7.2 Hz, 1H), 7.24-7.17 (m, 1H), 7.03 (d, J=3.2 Hz, 1H), 6.87 (s, 1H), 6.72 (s, 1H), 6.54-6.46 (m, 1H), 2.56 (s, 3H); $^{13}$C NMR (100 MHz, CDCl$_3$) δ 151.7, 143.2, 143.1, 140.1, 138.5, 131.7, 129.8, 128.0, 127.6, 126.2, 125.0, 123.6, 122.9, 122.5, 122.0, 112.3, 111.5, 110.2, 90.8, 18.8; HRMS (ESI) calcd for C$_{20}$H$_{15}$N$_2$O 299.1179 ([M+H]$^+$), found 299.1178.

2-19. Synthesis of methyl 6-(3,5-dimethoxyphenyl)indolizino[3,2-c]quinoline-12-carboxylate (IQ 19)

A desired compound was obtained by the method described in Example 2-1, except that a 2-(8-methylindolizine-2-yl)aniline compound was used instead of a 2-(indolizine-2-yl)aniline compound, and 3,5-dimethoxybenzaldehyde was used instead of 4-bromobenzaldehyde.

Yellow solid, mp 205.9-206.3° C. (53.7 mg, 93%); IR (ATR) v=2936, 2839, 1690, 1598, 1492, 1352, 1134 cm$^{-1}$; $^1$H NMR (400 MHz, CDCl$_3$) δ 9.68 (d, J=8.0 Hz, 1H), 8.46 (d, J=9.2 Hz, 1H), 8.26 (d, J=8.0 Hz, 1H), 7.96 (d, J=7.2 Hz, 1H), 7.74 (t, J=7.2 Hz, 1H), 7.66 (t, J=8.0 Hz, 1H), 7.34 (t, J=7.6 Hz, 1H), 6.74 (s, 2H), 6.70-6.60 (m, 2H), 4.10 (s, 3H), 3.84 (s, 6H); $^{13}$C NMR (100 MHz, CDCl$_3$) δ 165.9, 161.9, 147.9, 144.5, 141.6, 141.4, 131.0, 129.8, 128.5, 127.7, 127.64, 127.57, 126.0, 122.4, 121.9, 120.5, 112.3, 106.2, 102.0, 99.4, 55.8, 51.6; HRMS (ESI) calcd for C$_{25}$H$_{21}$N$_2$O$_4$ 413.1496 ([M+H]$^+$), found 413.1506.

2-20. Synthesis of methyl 6-(naphthalen-1-yl)indolizino[3,2-c]quinoline-12-carboxylate (IQ 20)

A desired compound was obtained by the method described in Example 2-1, except that 2-(8-methylindolizine-2-yl)aniline compound was used instead of a 2-(indolizine-2-yl)aniline compound, and 1-naphthaldehyde was used instead of 4-bromobenzaldehyde.

Yellow solid, mp 245.8-246.2° C. (55.8 mg, 99%); IR (ATR) v=3048, 2985, 1697, 1490, 1437, 1350, 1133 cm$^{-1}$; $^1$H NMR (400 MHz, CDCl$_3$) δ 9.76 (d, J=8.0 Hz, 1H), 8.43 (d, J=9.2 Hz, 1H), 8.30 (d, J=8.0 Hz, 1H), 7.59 (dd, J=2.8, 6.8 Hz, 1H), 7.98 (d, J=8.4 Hz, 1H), 7.77 (t, J=7.2 Hz, 1H), 7.74-7.66 (m, 3H), 7.49 (t, J=6.8 Hz, 1H), 7.34 (d, J=7.2 Hz, 1H), 7.31 (d, J=8.4 Hz, 1H), 7.26 (dd, J=6.8, 7.2 Hz, 1H), 7.22 (dd, J=6.8, 9.2 Hz, 1H), 6.32 (t, J=6.8 Hz, 1H), 4.11 (s, 3H); $^{13}$C NMR (100 MHz, CDCl$_3$) δ 166.0, 146.8, 145.0, 141.5, 136.7, 134.0, 131.4, 130.8, 129.9, 129.8, 128.6, 128.5, 127.7, 127.5, 127.4, 126.94, 126.87, 126.8, 126.2, 126.1, 124.9, 123.2, 122.5, 120.4, 112.4, 99.3, 51.6; HRMS (ESI) calcd for C$_{27}$H$_{19}$N$_2$O$_2$ 403.1441 ([M+H]$^+$), found 403.1437.

2-21. Synthesis of methyl 6-(1H-pyrrol-2-y)indolizino[3,2-c]quinoline-12-carboxylate (IQ 21: Formula 4)

A desired compound was obtained by the method described in Example 2-1, except that a methyl 2-(2-aminophenyl)indolizine-1-carboxylate compound was used instead of a 2-(indolizine-2-yl)aniline compound, and 1H-pyrrol-2-carbaldehyde was used instead of 4-bromobenzaldehyde.

Yellow solid, mp 230.8-231.4° C. (42.1 mg, 88%); IR (ATR) v=3323, 3108, 2944, 1690, 1588, 1494, 1439, 1350, 1224 cm$^{-1}$; $^1$H NMR (400 MHz, CDCl$_3$) δ 10.06 (s, 1H), 9.46 (d, J=8.0 Hz, 1H), 8.65-8.53 (m, 1H), 8.35 (d, J=9.2 Hz, 1H), 7.98 (d, J=8.0 Hz, 1H), 7.54-7.40 (m, 2H), 7.32 (t, J=6.8 Hz, 1H), 7.08 (s, 1H), 6.70 (t, J=6.8 Hz, 1H), 6.60 (s, 1H), 6.41 (s, 1H), 4.09 (s, 3H); $^{13}$C NMR (100 MHz, CDCl$_3$) δ 165.9, 144.3, 141.5, 140.4, 131.3, 128.7, 128.5, 128.3, 127.8, 127.6, 127.5, 125.4, 121.9, 121.8, 120.5, 120.3, 111.8, 110.9, 110.0, 99.2, 51.6; HRMS (ESI) calcd for C$_{21}$H$_{16}$N$_3$O$_2$ 342.1237 ([M+H]$^+$), found 342.1229.

2-22. Synthesis of 9-bromo-6-(4-methoxyphenyl)indolizino[3,2-c]quinoline (IQ 22)

A desired compound was obtained by the method described in Example 2-1, except that a 2-(6-bromoindolizine-2-yl)aniline compound was used instead of a 2-(indolizine-2-yl)aniline compound, and furan-2-carbaldehyde was used instead of 4-bromobenzaldehyde.

Yellow solid, mp 229.5-230.0° C. (50.2 mg, 89%); IR (ATR) v=3057, 3003, 1606, 1489, 1435, 1381, 1242, 1173, 669 cm$^{-1}$; $^1$H NMR (400 MHz, CDCl$_3$) δ 8.33 (d, J=7.6 Hz, 1H), 8.24 (d, J=8.4 Hz, 1H), 8.05 (s, 1H), 7.69 (t, J=7.6 Hz, 1H), 7.64-7.57 (m, 3H), 7.51 (d, J=9.2 Hz, 1H), 7.28 (s, 1H), 7.16 (d, J=8.4 Hz, 2H), 7.06 (d, J=9.6 Hz, 1H), 3.94 (s, 3H); $^{13}$C NMR (100 MHz, CDCl$_3$) δ 160.8, 148.5, 143.2, 136.7, 131.7, 131.5, 130.1, 129.7, 127.8, 127.0, 126.5, 126.0, 123.6, 122.3, 121.4, 119.9, 114.9, 104.2, 93.4, 55.7; HRMS (ESI) calcd for C$_{22}$H$_{16}$BrN$_2$O 403.0441 ([M+H]$^+$), found 403.0437.

2-23. Synthesis of 9-bromo-6-(p-tolyl)indolizino[3,2-c]quinoline (IQ 23)

A desired compound was obtained by the method described in Example 2-1, except that a 2-(6-bromoindolizine-2-yl)aniline compound was used instead of a 2-(indolizine-2-yl)aniline compound, and 4-methylbenzaldehyde was used instead of 4-bromobenzaldehyde.

Yellow solid, mp 230.8-231.2° C. (23.9 mg, 44%); IR (ATR) v=2921, 2852, 1610, 1487, 1435, 667 cm$^{-1}$; $^1$H NMR (400 MHz, CDCl$_3$) δ 8.33 (d, J=7.6 Hz, 1H), 8.25 (d, J=8.4 Hz, 1H), 7.96 (s, 1H), 7.69 (t, J=7.2 Hz, 1H), 7.61 (t, J=7.2 Hz, 1H), 7.55 (d, J=7.6 Hz, 2H), 7.50 (d, J=9.6 Hz, 1H), 7.44 (d, J=8.0 Hz, 2H), 7.27 (s, 1H), 7.05 (d, J=9.6 Hz, 1H), 2.52 (s, 3H); $^{13}$C NMR (100 MHz, CDCl$_3$) δ 148.9, 143.2, 139.6, 136.7, 136.2, 131.6, 130.1, 129.8, 128.5, 127.8, 127.0, 126.5, 126.0, 123.6, 122.3, 121.3, 119.8, 104.2, 93.4, 21.7; HRMS (ESI) calcd for C$_{22}$H$_{16}$BrN$_2$ 387.0491 ([M+H]$^+$), found 387.0490.

2-24. Synthesis of 9-bromo-6-(3,4-dimethoxyphenyl)indolizino[3,2-c]quinoline (IQ 24)

A desired compound was obtained by the method described in Example 2-1, except that a 2-(6-bromoindolizine-2-yl)aniline compound was used instead of a 2-(indolizine-2-yl)aniline compound, and 4-bromobenzaldehyde was used instead of 4-bromobenzaldehyde.

Green solid, mp 188.5-189.0° C. (45.5 mg, 75%); IR (ATR) v=3103, 3000, 1600, 1490, [0292] 1460, 1372, 1132, 667 cm$^{-1}$; $^1$H NMR (400 MHz, CDCl$_3$) δ 8.34 (d, J=8.0 Hz, 1H), 8.27 (d, J=8.0 Hz, 1H), 8.10 (s, 1H), 7.70 (t, J=7.2 Hz, 1H), 7.63 (t, J=7.2 Hz, 1H), 7.54 (d, J=9.6 Hz, 1H), 7.31 (s, 1H), 7.26-7.19 (m, 2H), 7.12 (d, J=8.0 Hz, 1H), 7.09 (d, J=9.6 Hz, 1H), 4.02 (s, 3H), 3.92 (s, 3H); $^{13}$C NMR (100 MHz, CDCl$_3$) δ 150.3, 149.9, 148.3, 143.0, 136.9, 131.8, 131.4, 129.5, 128.0, 127.1, 126.7, 126.1, 123.6, 122.3, 121.4, 121.2, 119.9, 111.9, 111.8, 104.3, 93.5, 56.4, 56.3; HRMS (ESI) calcd for C$_{23}$H$_{18}$BrN$_2$O$_2$ 433.0546 ([M+H]$^+$), found 433.0543.

2-25. Synthesis of 9-bromo-6-(furan-2-yl)indolizino[3,2-c]quinoline (IQ 25)

A desired compound was obtained by the method described in Example 2-1, except that a 2-(6-bromoindolizine-2-yl)aniline compound was used instead of a 2-(indolizine-2-yl)aniline compound, and furan-2-carbaldehyde was used instead of 4-bromobenzaldehyde.

Yellow solid, mp 193.3-193.6° C. (47.3 mg, 93%); IR (ATR) v=3065, 3013, 1599, 1480, 1313, 668 cm$^{-1}$; $^1$H NMR (400 MHz, CDCl$_3$) δ 8.30 (d, J=7.6 Hz, 1H), 8.25 (d, J=8.4 Hz, 1H), 8.09 (s, 1H), 7.78 (s, 1H), 7.70 (t, J=7.6 Hz, 1H), 7.63 (t, J=7.2 Hz, 1H), 7.52 (d, J=9.2 Hz, 1H), 7.26 (s, 1H), 7.15-7.06 (m, 2H), 6.78 (s, 1H); $^{13}$C NMR (100 MHz, CDCl$_3$) δ 143.4, 142.9, 138.2, 137.0, 132.1, 129.8, 128.0, 127.6, 126.9, 126.6, 123.6, 122.6, 121.4, 119.8, 112.7, 112.2, 104.8, 93.6; HRMS (ESI) calcd for C$_{19}$H$_{12}$BrN$_2$O 363.0128 ([M+H]$^+$), found 363.0126.

2-26. Synthesis of ethyl 6-(4-nitrophenyl)indolizino[3,2-c]quinoline-12-carboxylate (IQ 26)

A desired compound was obtained by the method described in Example 2-1, except that an ethyl 2-(2-aminophenyl)indolizine-1-carboxylate compound was used instead of a 2-(indolizine-2-yl)aniline compound, and 4-nitrobenzaldehyde was used instead of 4-bromobenzaldehyde.

Yellow solid, mp 245.8-246.1° C. (43.2 mg, 75%); IR (ATR) v=3112, 2985, 1689, 1597, 1560, 1436, 1349, 1215, 1137 cm$^{-1}$; $^1$H NMR (400 MHz, CDCl$_3$) δ 9.68 (d, J=8.4 Hz, 1H), 8.51 (d, J=9.6 Hz, 1H), 8.48 (d, J=8.8 Hz, 2H), 8.21 (d, J=8.0 Hz, 1H), 7.90-7.82 (m, 3H), 7.75 (t, J=7.2 Hz, 1H), 7.68 (t, J=7.2 Hz, 1H), 7.37 (dd, J=6.8, 8.8 Hz, 1H), 6.67 (t, J=6.4 Hz, 1H), 4.60 (q, J=7.2 Hz, 2H), 1.57 (t, J=7.2 Hz, 3H); $^{13}$C NMR (100 MHz, CDCl$_3$) δ 165.3, 148.5, 146.1, 145.4, 144.5, 141.6, 131.3, 130.2, 129.8, 128.8, 127.8, 127.7, 126.8, 126.5, 124.7, 122.4, 121.4, 121.0, 112.5, 100.1, 60.8, 14.8; HRMS (ESI) calcd for C$_{24}$H$_{18}$N$_3$O$_4$ 412.1292 ([M+H]$^+$), found 412.1286.

2-27. Synthesis of ethyl 6-(3-chlorophenyl)indolizino[3,2-c]quinoline-12-carboxylate (IQ 27)

A desired compound was obtained by the method described in Example 2-1, except that an ethyl 2-(2-aminophenyl)indolizine-1-carboxylate compound was used instead of a 2-(indolizine-2-yl)aniline compound, and 3-chlorobenzaldehyde was used instead of 4-bromobenzaldehyde.

Yellow solid, mp 214.3-214.5° C. (53.3 mg, 95%); IR (ATR) v=3111, 2961, 1679, 1631, 1489, 1435, 1386, 1218, 1174, 1026, 741 cm$^{-1}$; $^1$H NMR (400 MHz, CDCl$_3$) δ 9.68 (d, J=8.4 Hz, 1H), 8.49 (d, J=8.8 Hz, 1H), 8.23 (d, J=8.0 Hz, 1H), 7.92 (d, J=6.4 Hz, 1H), 7.75 (t, J=7.2 Hz, 1H), 7.72-7.62 (m, 2H), 7.61-7.51 (m, 2H), 7.51-7.45 (m, 1H), 7.34 (t, J=7.2 Hz, 1H), 6.65 (t, J=6.8 Hz, 1H), 4.59 (q, J=7.2 Hz, 2H), 1.56 (t, J=7.2 Hz, 3H); $^{13}$C NMR (100 MHz, CDCl$_3$) δ 165.4, 146.4, 144.5, 141.6, 141.5, 135.7, 131.2, 130.9, 129.8, 129.7, 129.0, 128.6, 127.8, 127.5, 127.2, 126.9, 126.1, 122.4, 121.7, 120.8, 112.3, 99.9, 60.7, 14.8; HRMS (ESI) calcd for C$_{24}$H$_{18}$ClN$_2$O$_2$ 401.1051 ([M+H]$^+$), found 401.1048.

2-28. Synthesis of ethyl 6-(3-fluorophenyl)indolizino[3,2-c]quinoline-12-carboxylate (IQ 28: Formula 5)

A desired compound was obtained by the method described in Example 2-1, except that an ethyl 2-(2-aminophenyl)indolizine-1-carboxylate compound was used instead of a 2-(indolizine-2-yl)aniline compound, and 3-fluorobenzaldehyde was used instead of 4-bromobenzaldehyde.

Yellow solid, mp 202.1-202.4° C. (53.8 mg, 100%); IR (ATR) v=3055, 3033, 2980, 1676, 1613, 1490, 1434, 1372, 1135 cm$^1$; $^1$H NMR (400 MHz, CDCl$_3$) δ 9.68 (d, J=8.4 Hz, 1H), 8.49 (d, J=8.8 Hz, 1H), 8.24 (d, J=8.0 Hz, 1H), 7.89 (d, J=6.4 Hz, 1H), 7.75 (t, J=6.8 Hz, 1H), 7.67 (t, J=7.6 Hz, 1H), 7.63-7.54 (m, 1H), 7.44-7.25 (m, 4H), 6.68-6.54 (m, 1H), 4.59 (q, J=7.2 Hz, 2H), 1.56 (t, J=7.2 Hz, 3H); $^{13}$C NMR (100 MHz, CDCl$_3$) δ 165.5, 163.4 (d, JC,F=247.9 Hz), 146.6, 143.0 (d, JC,F=295.8 Hz), 141.8 (d, JC,F=7.5 Hz), 131.4 (d, JC,F=33.2 Hz), 131.2, 129.8, 128.6, 127.6 (d, JC,F=24.0 Hz), 127.2, 126.1, 124.6, 124.5, 122.4, 121.7, 120.7, 116.6 (d, JC,F=20.9 Hz), 116.2, 116.0, 112.3, 99.8, 60.7, 14.8; HRMS (ESI) calcd for C$_{24}$H$_{18}$FN$_2$O$_2$ 385.1347 ([M+H]$^+$), found 385.1345.

2-29. Synthesis of ethyl 6-(3-methoxyphenyl)indolizino[3,2-c]quinoline-12-carboxylate (IQ 29)

A desired compound was obtained by the method described in Example 2-1, except that an ethyl 2-(2-aminophenyl)indolizine-1-carboxylate compound was used instead of a 2-(indolizine-2-yl)aniline compound, and 3-methoxybenzaldehyde was used instead of 4-bromobenzaldehyde.

Yellow solid, mp 173.4-173.8° C. (51.6 mg, 93%); IR (ATR) v=3031, 2957, 1675, 1588, 1488, 1434, 1350, 1109 cm$^{-1}$; $^1$H NMR (400 MHz, CDCl$_3$) δ 9.69 (d, J=8.4 Hz, 1H), 8.49 (d, J=9.2 Hz, 1H), 8.27 (d, J=8.0 Hz, 1H), 7.92 (d, J=7.2 Hz, 1H), 7.75 (t, J=7.2 Hz, 1H), 7.66 (t, J=6.8 Hz, 1H), 7.52 (t, J=8.0 Hz, 1H), 7.33 (t, J=6.8 Hz, 1H), 7.20-7.08 (m, 3H), 6.62 (t, J=6.8 Hz, 1H), 4.60 (q, J=7.2 Hz, 2H), 3.87 (s, 3H), 1.56 (t, J=7.2 Hz, 3H); $^{13}$C NMR (100 MHz, CDCl$_3$) δ 165.6, 160.6, 148.0, 144.6, 141.6, 140.9, 131.0, 130.9, 129.8, 128.5, 127.7, 127.54, 127.46, 125.9, 122.4, 122.0, 120.8, 120.6, 115.8, 113.5, 112.1, 99.7, 60.6, 55.6, 14.8; HRMS (ESI) calcd for C$_{25}$H$_{21}$N$_2$O$_3$ 397.1547 ([M+H]$^+$), found 397.1542.

2-30. Synthesis of ethyl 6-(3,4-dimethoxyphenyl)indolizino[3,2-c]quinoline-12-carboxylate (IQ 30: Formula 6)

A desired compound was obtained by the method described in Example 2-1, except that an ethyl 2-(2-aminophenyl)indolizine-1-carboxylate compound was used instead of a 2-(indolizine-2-yl)aniline compound, and 3,4-dimethoxybenzaldehyde was used instead of 4-bromobenzaldehyde.

Yellow solid, mp 195.5-195.8° C. (58.5 mg, 98%); IR (ATR) ν=3074, 2969, 1681, 1600, 1497, 1435, 1350, 1132, 1024 cm[-1]; $^1$H NMR (400 MHz, CDCl$_3$) δ 9.68 (d, J=8.4 Hz, 1H), 8.49 (d, J=9.2 Hz, 1H), 8.25 (d, J=8.0 Hz, 1H), 7.98 (d, J=7.2 Hz, 1H), 7.73 (t, J=6.8 Hz, 1H), 7.65 (t, J=6.8 Hz, 1H), 7.33 (t, J=7.6 Hz, 1H), 7.20-7.12 (m, 2H), 7.09 (d, J=8.0 Hz, 1H), 6.64 (t, J=7.2 Hz, 1H), 4.59 (q, J=7.2 Hz, 2H), 4.01 (s, 3H), 3.91 (s, 3H), 1.56 (t, J=7.2 Hz, 3H); $^{13}$C NMR (100 MHz, CDCl$_3$) δ 165.5, 150.0, 149.9, 147.9, 144.6, 141.5, 132.1, 131.0, 129.6, 128.4, 127.7, 127.5, 127.4, 125.7, 122.3, 122.13, 122.14, 120.5, 112.1, 112.0, 111.5, 99.6, 60.6, 56.2, 56.2, 14.7; HRMS (ESI) calcd for $C_{26}H_{22}N_2O_4$ 427.1652 ([M+H]$^+$), found 427.1660.

2-31. Synthesis of ethyl 6-(naphthalen-2-yl)indolizino[3,2-c]quinoline-12-carboxylate (IQ 31)

A desired compound was obtained by the method described in Example 2-1, except that an ethyl 2-(2-aminophenyl)indolizine-1-carboxylate compound was used instead of a 2-(indolizine-2-yl)aniline compound, and 2-naphthaldehyde was used instead of 4-bromobenzaldehyde.

Yellow solid, mp 210.3-210.7° C. (58.3 mg, 100%); IR (ATR) ν=3125, 2973, 1679, 1599, 1492, 1434, 1377, 1215, 1105, 1030 cm$^{-1}$; $^1$H NMR (400 MHz, CDCl$_3$) δ 9.71 (d, J=8.4 Hz, 1H), 8.49 (d, J=9.2 Hz, 1H), 8.28 (d, J=8.0 Hz, 1H), 8.18 (s, 1H), 8.07 (d, J=8.4 Hz, 1H), 7.98 (d, J=7.6 Hz, 1H), 7.96-7.90 (m, 2H), 7.75 (t, J=7.2 Hz, 1H), 7.70-7.64 (m, 2H), 7.64-7.54 (m, 2H), 7.29 (dd, J=6.8, 9.2 Hz, 1H), 6.49 (t, J=6.8 Hz, 1H), 4.61 (q, J=7.2 Hz, 2H), 1.57 (t, J=7.2 Hz, 3H); $^{13}$C NMR (100 MHz, CDCl$_3$) δ 165.6, 148.0, 144.7, 141.6, 137.0, 133.8, 133.6, 131.1, 129.8, 129.5, 128.7, 128.5, 128.2, 128.1, 127.8, 127.46, 127.44, 127.1, 127.0, 126.0, 125.9, 122.4, 122.2, 120.6, 112.1, 99.7, 60.6, 14.8; HRMS (ESI) calcd for $C_{28}H_{21}N_2O_2$ 417.1598 ([M+H]$^+$), found 417.1598.

2-32. Synthesis of ethyl 6-(naphthalen-1-yl)indolizino[3,2-c]quinoline-12-carboxylate (IQ 32)

A desired compound was obtained by the method described in Example 2-1, except that an ethyl 2-(2-aminophenyl)indolizine-1-carboxylate compound was used instead of a 2-(indolizine-2-yl)aniline compound, and 1-naphthaldehyde was used instead of 4-bromobenzaldehyde.

2-33. Synthesis of 11-methyl-6-(naphthalen-1-ypindolizino[3,2-c]quinoline (IQ 33)

2-(8-methylindolizine-2-yl)aniline (16 mg, 0.072 mmol) and 1-naphthaldehyde (0.09 mmol, 1.2 equiv.) were dissolved in 1 mL of dry CH$_2$Cl$_2$, and mixed with FeCl$_3$ (0.007 mmol, 0.1 equiv.) to allow a reaction at 60° C. for 19 hours. After the reaction, work-up was performed with H$_2$O and dichloromethane, and the reaction mixture was purified by silica gel column chromatography using a solvent mixture (hexane:ethylacetate:dichloromethane=20:1:2), thereby obtaining a desired compound (74%, 19 mg).

Yellow solid; $^1$H NMR (400 MHz, CDCl$_3$) δ 8.50 (d, J=8.0 Hz, 1H), 8.30 (d, J=7.6 Hz, 1H), 8.09 (d, J=8.8 Hz, 1H), 7.99 (d, J=8.0 Hz, 1H), 7.78-7.66 (m, 4H), 7.50 (t, J=7.2 Hz, 1H), 7.39 (d, J=8.4 Hz, 1H), 7.33 (s, 1H), 7.29 (d, J=7.6 Hz, 1H), 7.09 (d, J=7.2 Hz, 1H), 6.78 (d, J=6.8 Hz, 1H), 6.12 (t, J=6.8 Hz, 1H), 2.59 (s, 3H).

2-34. Synthesis of 6-(naphthalen-1-yl)pyrido[2',1':2,3]imidazo[4,5-c]quinoline (IQ 34)

2-(imidazo[1,2-a]pyridine-2-yl)aniline (11 mg, 0.05 mmol) and 1-naphthaldehyde (0.06 mmol, 1.2 equiv.) were dissolved in 1 mL of dry CH$_2$Cl$_2$, and mixed with FeCl$_3$ (0.005 mmol, 0.1 equiv.) to allow a reaction at 60° C. for 19 hours. After the reaction, work-up was performed with H$_2$O and dichloromethane, and the reaction mixture was purified by silica gel column chromatography using a solvent mixture (hexane:ethylacetate:dichloromethane=5:1:2), thereby obtaining a desired compound (92%, 15.9 mg).

Yellow solid; $^1$H NMR (400 MHz, CDCl$_3$) δ 8.88 (d, J=7.6 Hz, 1H), 8.36 (d, J=8.0 Hz, 1H), 8.13 (d, J=8.0 Hz, 1H), 8.02 (d, J=8.4 Hz, 1H), 7.91 (d, J=9.2 Hz, 1H), 7.89-7.69 (m, 4H), 7.54 (t, J=7.6 Hz, 1H), 7.44 (d, J=7.2 Hz, 1H), 7.50-7.40 (m, 2H), 7.33 (t, J=7.2 Hz, 1H), 7.29-7.22 (m, 1H), 6.53 (t, J=6.8 Hz, 1H).

2-35. Synthesis of 9-methyl-6-(naphthalen-1-ypindolizino[3,2-c]quinoline (IQ 35)

2-(6-methylindolizine-2-yl)aniline (16 mg, 0.072 mmol) and 1-naphthaldehyde (0.20 mmol, 1.2 equiv.) were dissolved in 1 mL of dry CH$_2$Cl$_2$, and mixed with FeCl$_3$ (0.017 mmol, 0.1 equiv.) to allow a reaction at 60° C. for 19 hours. After the reaction, work-up was performed with H$_2$O and dichloromethane, and the reaction mixture was purified by silica gel column chromatography using a solvent mixture (hexane:ethylacetate:dichloromethane=30:1:2), thereby obtaining a desired compound (34%, 20.4 mg).

Yellow solid; $^1$H NMR (400 MHz, CDCl$_3$) δ 8.44 (d, J=8.0 Hz, 1H), 8.28 (d, J=8.0 Hz, 1H), 8.14-8.06 (m, 1H), 8.00 (d, J=8.4 Hz, 1H), 7.77-7.63 (m, 4H), 7.59-7.46 (m, 2H), 7.42 (d, J=8.4 Hz, 1H), 7.34-7.36 (m, 2H), 6.90 (s, 1H), 6.83 (d, J=9.2 Hz, 1H), 1.78 (s, 3H).

2-36. Synthesis of 4-(indolizino[3,2-c]quinolin-6-yl)-N,N-dimethylaniline (IQ 36:Formula 12)

2-(indolizine-2-yl)aniline (20 mg, 0.096 mmol) and 4-(dimethylamino)benzaldehyde (0.106 mmol, 1.1 equiv.) were dissolved in 0.5 mL of dry CH$_2$Cl$_2$, and 0.5 mL of 2% TFA in CH$_2$Cl$_2$ was added dropwise to allow a reaction at room temperature for 19 hours. After the reaction, work-up was performed with saturated NaHCO$_3$, and the reaction mixture was purified by silica gel column chromatography using a solvent mixture (hexane:ethylacetate:dichloromethane=10:1:2), thereby obtaining a desired compound (31%, 10 mg).

Yellow solid, mp: 173.8-175.0° C.; $^1$H NMR (400 MHz, CDCl$_3$) δ 8.35 (d, J=7.2 Hz, 1H), 8.25 (d, J=8.0 Hz, 1H), 8.13 (d, J=7.2 Hz, 1H), 7.66 (dd, J=1.2, 8.4 Hz, 1H), 7.63-7.57 (m, 2H), 7.55 (d, J=8.8 Hz, 2H), 7.25 (s, 1H), 7.02 (dd, J=6.4, 8.4 Hz, 1H), 6.91 (d, J=8.4 Hz, 2H), 6.46-6.39 (m, J=6.8 Hz, 1H), 3.07 (s, 6H); $^{13}$C NMR (100 MHz, CDCl$_3$) δ 151.2, 149.3, 143.2, 138.9, 131.7, 129.8, 129.4, 127.5, 127.3, 125.4, 123.6, 123.3, 122.3, 121.6, 119.2, 112.8, 109.6, 92.1, 40.7; HRMS (ESI-QTOF) m/z [M+H]$^+$ calcd for $C_{23}H_{20}N_3$ 338.1652, found 338.1652.

2-37. Synthesis of N,N-diethyl-4-(indolizino[3,2-c]quinolin-6-yl)aniline (IQ 37)

A desired compound (31%, 11 mg) was obtained by the method of Example 2-36, except that 4-(diethylamino)benzaldehyde was used instead of 4-(dimethylamino)benzaldehyde.

Yellow solid, mp: 77.2-78.6° C.; $^1$H NMR (400 MHz, CDCl$_3$) δ 8.35 (d, J=7.6 Hz, 1H), 8.26 (t, J=6.0 Hz, 2H), 7.72-7.56 (m, 3H), 7.53 (t, J=8.4 Hz, 2H), 7.26 (s, 1H), 7.04 (t, J=7.2 Hz, 1H), 6.86 (d, J=8.4 Hz, 2H), 6.45 (t, J=6.8 Hz, 1H), 3.47 (q, J=7.2 Hz, 4H), 1.24 (t, J=7.2 Hz, 6H); $^{13}$C NMR (100 MHz, CDCl$_3$) δ 149.5, 148.5, 143.5, 138.7, 131.6, 130.0, 129.6, 127.4, 127.3, 126.4, 125.2, 123.5, 122.3, 121.6, 119.1, 112.2, 109.4, 92.0, 44.6, 12.7; HRMS (ESI-QTOF) m/z [M+H]$^+$ calcd for $C_{25}H_{24}N_3$ 366.1965, found 366.1966.

2-38. Synthesis of 6-(4-methoxyphenyl)-12-nitroindolizino[3,2-c]quinoline (IQ 38)

6-(4-methoxyphenyl)indolizino[3,2-c]quinoline (9 mg, 0.028 mmol) was dissolved in 1 mL of CH$_3$CN and mixed with NBS (0.028 mmol, 1 equiv.) and AgNO$_3$ (0.028 mmol, 1 equiv.) to allow a reaction at 120° C. for 1 hour. After the reaction, a solvent was distilled under reduced pressure, and the reaction mixture was purified by silica gel column chromatography using a solvent mixture (hexane:ethylacetate:dichloromethane=10:1:2), thereby obtaining a desired compound (42%, 4.3 mg).

Orange solid, mp: 265.4-266.9° C.; $^1$H NMR (400 MHz, CDCl$_3$) δ 9.51 (d, J=8.4 Hz, 1H), 8.80 (d, J=8.8 Hz, 1H), 8.26 (d, J=8.4 Hz, 1H), 8.18 (d, J=6.8 Hz, 1H), 7.81 (t, J=7.2 Hz, 1H), 7.70 (t, J=7.6 Hz, 1H), 7.65 (dd, J=7.2, 8.4 Hz, 1H), 7.57 (d, J=8.4 Hz, 2H), 7.16 (d, J=8.4 Hz, 2H), 6.87 (t, J=6.8 Hz, 1H), 3.95 (s, 3H); $^{13}$C NMR (100 MHz, CDCl$_3$) δ 160.9, 147.7, 145.6, 138.0, 131.7, 131.2, 130.10, 130.06, 129.7, 128.0, 127.6, 126.6, 125.5, 120.9, 120.3, 120.0, 115.3, 114.6, 55.7; HRMS (ESI-QTOF) m/z [M+H]$^+$ calcd for $C_{22}H_{16}N_3O_3$ 370.1186, found 370.1188.

2-39. Synthesis of 6-(4-methoxyphenyl)indolizino[3,2-c]quinoline-12-carbonitrile (IQ 39)

12-bromo-6-(4-methoxyphenyl)indolizino[3,2-c]quinoline (20 mg, 0.05 mmol) was distilled in 0.5 mL of DMF and mixed with CuCN (0.40 mmol, 8 equiv.) and NaI (0.1 mmol, 2 equiv.) to allow a reaction at 150° C. for 1 hour. After the reaction, work-up was performed with ethyl acetate and H$_2$O as solvents and the reaction mixture was purified by silica gel column chromatography using a solvent mixture (hexane:ethylacetate:dichloromethane=20:1:2), thereby obtaining a desired compound (24%, 4.1 mg).

Yellow solid, mp: 268.0-268.8° C.; $^1$H NMR (400 MHz, CDCl$_3$) δ 8.98 (d, J=8.4 Hz, 1H), 8.27 (d, J=8.0 Hz, 1H), 8.08 (d, J=7.2 Hz, 1H), 7.92 (d, J=8.8 Hz, 1H), 7.79 (t, J=7.2 Hz, 1H), 7.72 (t, J=7.6 Hz, 1H), 7.59 (d, J=8.4 Hz, 2H), 7.42 (t, J=7.6 Hz, 1H), 7.15 (d, J=8.4 Hz, 2H), 6.74 (t, J=6.8 Hz, 1H), 3.95 (s, 3H); $^{13}$C NMR (100 MHz, CDCl$_3$) δ 160.8, 148.2, 144.0, 143.1, 131.3, 131.1, 130.1, 129.9, 129.2, 128.0, 126.9, 123.6, 121.4, 121.3, 118.0, 117.1, 115.1, 112.9, 55.7; HRMS (ESI-QTOF) m/z [M+H]$^+$ calcd for $C_{23}H_{16}N_3O$ 350.1288, found 350.1286.

2-40. Synthesis of 12-chloro-6-(4-methoxyphenyl)indolizino[3,2-c]quinoline (IQ 40)

6-(4-methoxyphenyl)indolizino[3,2-c]quinoline (20 mg, 0.062 mmol) was dissolved in 1 mL of dry CH$_2$Cl$_2$ and mixed with NCS (0.062 mmol, 1 equiv.) to allow a reaction at room temperature for 2 hours. After the reaction, the solvent was distilled under reduced pressure, and the reaction mixture was purified by silica gel column chromatography using a solvent mixture (hexane:ethylacetate:dichloromethane=10:1:2), thereby obtaining a desired compound (71%, 15.7 mg).

Yellow solid, mp: 215.1-216.4° C.; $^1$H NMR (400 MHz, CDCl$_3$) δ 9.17 (d, J=8.0 Hz, 1H), 8.26 (d, J=8.0 Hz, 1H), 7.89 (d, J=7.2 Hz, 1H), 7.77-7.62 (m, 3H), 7.58 (d, J=8.4 Hz, 2H), 7.18-7.08 (m, 1H), 7.13 (d, J=8.4 Hz, 2H), 6.49 (t, J=6.4 Hz, 1H), 3.94 (s, 3H); $^{13}$C NMR (100 MHz, CDCl$_3$) δ 160.6, 148.3, 143.6, 134.7, 132.0, 130.1, 129.5, 127.9, 126.7, 125.9, 125.8, 124.0, 123.9, 121.9, 119.8, 116.7, 115.0, 110.6, 96.8, 55.6; HRMS (ESI-QTOF) m/z [M+H]$^+$ calcd for $C_{22}H_{16}ClN_2O$ 359.0946, found 359.0945.

2-42. Synthesis of 12-chloro-6-(4-methoxyphenyl)indolizino[3,2-c]quinoline (IQ 42)

A 2-(indolizine-2-yl)aniline compound (30 mg, 0.144 mmol) and 2-thiophenecarboxaldehyde (0.173 mmol, 1.2 equiv.) were dissolved in 1 mL of dry CH$_2$Cl$_2$ and mixed with FeCl$_3$ (0.043 mmol, 0.3 equiv.) to allow a reaction at 60° C. for 19 hours. After the reaction, work-up was performed with H$_2$O and dichloromethane, and the reaction mixture was purified by silica gel column chromatography using a solvent mixture (hexane:ethylacetate:dichloromethane=10:1:2), thereby obtaining a desired compound (50%, 21.6 mg).

Yellow solid, mp: 171.1-178.9° C.; $^1$H NMR (400 MHz, CDCl$_3$) δ 8.35 (d, J=7.6 Hz, 1H), 8.25 (d, J=8.4 Hz, 1H), 8.03 (d, J=7.2 Hz, 1H), 7.69 (t, J=8.0 Hz, 1H), 7.65-7.56 (m, 3H), 7.40 (d, J=3.2 Hz, 1H), 7.27 (dd, J=4.0, 4.8 Hz, 1H), 7.25 (s, 1H), 7.04 (dd, J=6.4, 8.8 Hz, 1H), 6.48 (t, J=7.2 Hz, 1H); $^{13}$C NMR (100 MHz, CDCl$_3$) δ 143.1 141.8 140.8, 139.1, 131.8, 129.7, 128.0, 127.83, 127.77, 127.7, 126.9, 126.1, 123.7, 123.6, 122.6, 121.7, 119.3, 110.0, 92.3; HRMS (ESI-QTOF) m/z [M+H]$^+$ calcd for $C_{19}H_{13}N_2S$ 301.0794, found 301.0793.

2-43. Synthesis of methyl 6-(pyridin-2-yl)indolizino[3,2-c]quinoline-12-carboxylate (IQ 43)

Methyl 2-(2-aminophenyl)indolizine-1-carboxylate (30 mg, 0.113 mmol) and 2-pyridinecarboxaldehyde (0.135 mmol, 1.2 equiv.) were dissolved in 1 mL of dry CH$_2$Cl$_2$ and mixed with FeCl$_3$ (0.043 mmol, 0.3 equiv.) to allow a reaction at 60° C. for 19 hours. After the reaction, work-up was performed with H$_2$O and dichloromethane, and the reaction mixture was purified by silica gel column chromatography using a solvent mixture (hexane:ethylacetate:dichloromethane=1:1:1), thereby obtaining a desired compound (54%, 21.4 mg).

Yellow solid, mp: 206.7-207.2° C.; $^1$H NMR (400 MHz, CDCl$_3$) δ 9.71 (d, J=8.4 Hz, 1H), 8.81 (d, J=4.8 Hz, 1H), 8.49 (d, J=9.2 Hz, 1H), 8.26 (d, J=8.0 Hz, 1H), 8.05 (d, J=4.0 Hz, 2H), 8.01 (d, J=7.2 Hz, 1H), 7.76 (t, J=7.2 Hz, 1H), 7.70 (t, J=6.8 Hz, 1H), 7.54 (q, J=4.4 Hz, 1H), 7.37 (m, 1H), 6.67 (t, J=6.8 Hz, 1H), 4.12 (s, 3H); $^{13}$C NMR (100 MHz, CDCl$_3$) δ 166.0, 158.1, 149.5, 146.5, 144.6, 141.7, 138.1, 131.7, 129.9, 128.5, 128.2, 127.7, 127.6, 126.4, 125.2, 124.4, 122.8, 122.1, 120.6, 111.9, 51.9; HRMS (ESI-QTOF) m/z [M+H]$^+$ calcd for $C_{22}H_{16}N_3O_2$ 354.1237, found 354.1236.

2-44. Synthesis of methyl 6-(thiophen-2-yl)indolizino[3,2-c]quinoline-12-carboxylate (IQ 44)

Methyl 2-(2-aminophenyl)indolizine-1-carboxylate (30 mg, 0.113 mmol) and 2-thiophenecarboxaldehyde (0.135 mmol, 1.2 equiv.) were dissolved in 1 mL of dry $CH_2Cl_2$ mixed with $FeCl_3$ (0.043 mmol, 0.3 equiv.) to allow a reaction at 60° C. for 19 hours. After the reaction, work-up was performed with $H_2O$ and dichloromethane, and the reaction mixture was purified by silica gel column chromatography using a solvent mixture (hexane:ethylacetate:dichloromethane=10:1:2), thereby obtaining a desired compound (80%, 32.3 mg).

Yellow solid, mp: 196.6-197.0° C.; $^1$H NMR (400 MHz, CDCl$_3$) δ 9.66 (d, J=8.4 Hz, 1H), 8.46 (d, J=9.6 Hz, 1H), 8.25 (d, J=8.4 Hz, 1H), 8.07 (d, J=7.2 Hz, 1H), 7.75 (t, J=8.0 Hz, 1H), 7.67 (t, J=8.0 Hz, 1H), 7.62 (d, J=4.4 Hz, 1H), 7.40-7.31 (m, 2H), 7.30-7.26 (m, 1H), 6.69 (t, J=6.8 Hz, 1H), 4.11 (s, 3H); $^{13}$C NMR (100 MHz, CDCl$_3$) δ 165.9, 144.6, 141.7, 141.3, 140.3, 131.2, 129.9, 128.6, 128.23, 128.17, 128.1, 127.7, 127.6, 127.4, 126.4, 122.7, 122.5, 120.6, 112.3, 51.6; HRMS (ESI-QTOF) m/z [M+H]$^+$ calcd for $C_{21}H_{15}N_2O_2S$ 359.0849, found 359.0851.

2-45. Synthesis of 12-(4-fluorophenyl)-6-(4-methoxyphenyl)indolizino[3,2-c]quinoline (IQ 45)

12-bromo-6-(4-methoxyphenyl)indolizino[3,2-c]quinoline (20 mg, 0.05 mmol), aryl borate (0.1 mmol, 2 equiv.), Pd(PPh$_3$)$_4$ (0.0025 mmol, 0.05 equiv.) and K$_2$CO$_3$ (0.15 mmol, 3 equiv.) were dissolved in 2.5 mL of a solvent mixture (toluene:methanol:H$_2$O=2:2:1) to allow a reaction at 100° C. for 6 hours. After the reaction, a solvent was removed, work-up was performed with ethanol and H$_2$O, and then the reaction mixture was purified by silica gel column chromatography using a solvent mixture (hexane:ethylacetate:dichloromethane=20:1:2), thereby obtaining a desired compound.

Yellow solid, mp: 202.3-203.2° C.; $^1$H NMR (400 MHz, CDCl$_3$) δ 8.24 (d, J=8.4 Hz, 1H), 8.02 (d, J=8.4 Hz, 2H), 7.95 (d, J=7.2 Hz, 1H), 7.68-7.61 (m, 1H), 7.64 (d, J=8.8 Hz, 2H), 7.61-7.53 (m, 2H), 7.41 (d, J=9.2 Hz, 1H), 7.35 (t, J=7.2 Hz, 1H), 7.28 (d, J=8.8 Hz, 2H), 7.16 (d, J=8.8 Hz, 2H), 7.01 (t, J=6.8 Hz, 1H), 6.46 (t, J=6.8 Hz, 1H), 3.95 (s, 3H); $^{13}$C NMR (100 MHz, CDCl$_3$) δ 163.8, 161.3, 160.5, 148.6, 133.1, 133.0, 131.0, 130.2, 129.9, 128.3, 127.4, 126.8, 125.3, 124.0, 123.7, 122.7, 120.8, 117.7, 116.2, 116.0, 114.9, 110.3, 108.5, 55.7; HRMS (ESI-QTOF) m/z [M+H]$^+$ calcd for $C_{28}H_{20}FN_2O$ 419.1554, found 419.1555.

2-46. Synthesis of 12-(4-chlorophenyl)-6-(4-methoxyphenyl)indolizino [3,2-c]quinolone (IQ 46)

Yellow solid, mp: 211.6-212.3° C.; $^1$H NMR (400 MHz, CDCl$_3$) δ 8.24 (d, J=8.0 Hz, 1H), 8.05 (d, J=8.0 Hz, 1H), 7.95 (d, J=6.8 Hz, 1H), 7.69-7.59 (m, 3H), 7.56 (s, 4H), 7.43 (d, J=8.8 Hz, 1H), 7.37 (t, J=7.6 Hz, 1H), 7.15 (d, J=7.6 Hz, 2H), 7.02 (t, J=6.8 Hz, 1H), 6.47 (t, J=6.4 Hz, 1H), 3.95 (s, 3H); $^{13}$C NMR (100 MHz, CDCl$_3$) δ 160.5, 148.6, 143.8, 137.0, 133.7, 133.4, 132.8, 130.2, 129.9, 129.3, 128.1, 127.5, 126.8, 125.4, 124.0, 123.8, 122.6, 120.9, 117.6, 114.9, 110.4, 108.2, 55.7; HRMS (ESI-QTOF) m/z [M+H]$^+$ calcd for $C_{28}H_{20}ClN_2O$ 435.1259, found 435.1259.

2-47. Synthesis of 6-(4-methoxyphenyl)-12-(4-(trifluoromethyl)phenyl)indolizino[3,2-c]quinolone (IQ 47)

Yellow solid, mp: 233.3-233.5° C.; $^1$H NMR (400 MHz, CDCl$_3$) δ 8.25 (d, J=8.4 Hz, 1H), 8.02 (d, J=8.0 Hz, 1H), 7.97 (d, J=7.6 Hz, 1H), 7.85 (d, J=8.0 Hz, 2H), 7.77 (d, J=8.0 Hz, 2H), 7.68-7.59 (m, 3H), 7.45 (d, J=8.8 Hz, 1H), 7.37 (t, J=7.2 Hz, 1H), 7.16 (d, J=8.4 Hz, 2H), 7.04 (t, J=6.8 Hz, 1H), 6.49 (t, J=6.8 Hz, 1H), 3.95 (s, 3H); $^{13}$C NMR (100 MHz, CDCl$_3$) δ 160.6, 148.7, 143.9, 139.4, 137.0, 132.2, 131.8, 130.1, 130.0, 128.0, 127.6, 126.9, 126.0 (q, JC,F=3.9 Hz), 125.5, 124.2, 123.9, 122.5, 121.1, 117.4, 115.0, 110.6, 108.0, 55.7; HRMS (ESI-QTOF) m/z [M+H]$^+$ calcd for $C_{29}H_{20}F_3N_2O$ 469.1522, found 469.1520.

2-48. Synthesis of 1-(4-(6-(4-methoxyphenyl)indolizino[3,2-c]quinolin-12-yl)phenyl)ethanone (IQ 48)

Yellow solid, mp: 256.7-258.3° C.; $^1$H NMR (400 MHz, CDCl$_3$) δ 8.25 (d, J=8.0 Hz, 1H), 8.18 (d, J=8.0 Hz, 2H), 8.07 (d, J=8.4 Hz, 1H), 7.97 (d, J=7.2 Hz, 1H), 7.76 (d, J=8.4 Hz, 2H), 7.64 (d, J=8.0 Hz, 2H), 7.63-7.60 (m, 1H), 7.48 (d, J=8.0 Hz, 1H), 7.35 (t, J=7.2 Hz, 1H), 7.16 (d, J=8.4 Hz, 2H), 7.05 (dd, J=6.8, 8.4 Hz, 1H), 6.49 (t, J=6.8 Hz, 1H), 3.96 (s, 3H), 2.74 (s, 3H); $^{13}$C NMR (100 MHz, CDCl$_3$) δ 198.0, 160.5, 148.6, 143.9, 140.7, 136.9, 136.16, 131.6, 130.1, 130.0, 129.1, 128.0, 127.6, 126.9, 125.4, 124.2, 124.0, 122.5, 121.1, 117.5, 115.0, 110.6, 108.4, 55.7, 26.9; HRMS (ESI-QTOF) m/z [M+H]$^+$ calcd for $C_{30}H_{23}N_2O_2$ 443.1754, found 443.1753.

2-49. 12-Bromo-6-(4-methoxyphenyl)indolizino[3,2-c]quinoline (IQ 49)

6-(4-methoxyphenyl)indolizino[3,2-c]quinolone (50 mg, 0.154 mmol) was dissolved in 5 mL of CH$_3$CN and mixed with NBS (0.154 mmol, 1 equiv.) to allow a reaction at 0° C. for 1 hour. After the reaction, a solvent was distilled under reduced pressure, and the reaction mixture was purified by silica gel column chromatography using a solvent mixture (hexane:ethylacetate:dichloromethane=5:1:2), thereby obtaining a desired compound (96%, 59.8 mg).

Yellow solid, mp: 215.4-216.9° C.; $^1$H NMR (400 MHz, CDCl$_3$) δ 9.35 (d, J=8.0 Hz, 1H), 8.25 (d, J=8.4 Hz, 1H), 7.89 (d, J=7.2 Hz, 1H), 7.79-7.62 (m, 3H), 7.57 (d, J=8.0 Hz, 2H), 7.20-7.07 (m, 3H), 6.49 (t, J=6.8 Hz, 1H), 3.93 (s, 3H); $^{13}$C NMR (100 MHz, CDCl$_3$) δ 160.6, 148.2, 143.8, 136.0, 132.1, 130.1, 129.7, 127.9, 127.1, 126.9, 125.5, 124.4, 123.4, 122.1, 120.8, 117.7, 115.0, 110.7, 81.7, 55.6; HRMS (ESI-QTOF) m/z [M+H]$^+$ calcd for $C_{22}H_{16}BrN_2O$ 403.0411, found 403.0414.

2-50. Synthesis of 12-Iodo-6-(4-methoxyphenyl)indolizino[3,2-c]quinoline (IQ 50)

6-(4-methoxyphenyl)indolizino[3,2-c]quinolone (12 mg, 0.036 mmol) was dissolved in 1 mL of CH$_3$CN and mixed with NIS (0.036 mmol, 1 equiv.) to allow a reaction at 0° C. for 1 hour. After the reaction, a solvent was distilled under reduced pressure, and the reaction mixture was purified by silica gel column chromatography using a solvent mixture (hexane:ethylacetate:dichloromethane=5:1:2), thereby obtaining a desired compound (81%, 13.1 mg).

Yellow solid, mp: 213.7-214.9° C.; $^1$H NMR (400 MHz, CDCl$_3$) δ 9.62 (d, J=7.6 Hz, 1H), 8.26 (d, J=8.0 Hz, 1H), 7.89 (d, J=7.2 Hz, 1H), 7.79-7.65 (m, 3H), 7.57 (d, J=8.0 Hz, 2H), 7.17 (d, J=7.6 Hz, 1H), 7.13 (d, J=8.4 Hz, 2H), 6.50 (t, J=6.8 Hz, 1H), 3.94 (s, 3H); NMR (100 MHz, CDCl₃) δ 160.4, 147.8, 143.6, 138.8, 131.8, 129.9, 129.6, 129.1, 127.8, 127.0, 125.0, 122.1, 119.6, 117.5, 114.8, 110.7, 105.2, 103.3, 55.5; HRMS (ESI-QTOF) m/z [M+H]⁺ calcd for C₂₂H₁₆IN₂O 451.0302, found 451.0302.

2-51. Synthesis of ethyl 6-(4-methoxyphenyl)indolizino[3,2-c]quinoline-12-carboxylate (IQ 51)

A desired compound was obtained by the method of Example 2-1, except that an ethyl 2-(2-aminophenyl)indolizine-1-carboxylate compound was used instead of a 2-(indolizine-2-yl)aniline compound, and benzaldehyde was used instead of 4-bromobenzaldehyde.

Yellow solid, ¹H NMR (300 MHz, CDCl₃) δ 9.65 (d, J=7.0 Hz, 1H), 8.49 (d, J=9.3 Hz, 1H), 8.23 (d, J=7.7 Hz, 1H), 8.03 (d, J=7.1 Hz, 2H), 7.72 (td, J=6.9, 1.5 Hz, 1H), 7.64 (td, J=8.3, 1.5 Hz, 1H), 7.55 (d, J=8.8 Hz, 2H), 7.33 (t, J=7.7 Hz, 1H), 7.12 (d, J=8.8 Hz, 2H), 6.62 (t, J=7.1 Hz, 1H), 4.56 (q, J=7.1 Hz, 2H), 3.93 (s, 1H), 1.55 (t, J=7.1 Hz, 3H).

2-52. Synthesis of 11-methyl-6-(thiophen-2-yl)indolizino[3,2-c]quinoline (IQ 52: Formula 14)

A desired compound was obtained by the method of Example 2-1, except that a 2-(8-methylindolizine-2-yl)aniline compound was used instead of a 2-(indolizine-2-yl)aniline compound, and thiophene-2-carbaldehyde was used instead of 4-bromobenzaldehyde.

Yellow solid, ¹H NMR (300 MHz, CDCl₃) δ 8.35 (dd, J=7.9, 1.4 Hz, 1H), 8.21 (d, J=8.0 Hz, 1H), 7.9 (d, J=7.1 Hz, 1H), 7.68-7.55 (m, 3H), 7.36 (dd, J=3.5, 1.1 Hz, 1H), 7.23-7.21 (m, 2H), 6.83 (d, J=6.6 1H), 6.40 (t, J=6.9 Hz, 1H), 2.54 (s, 1H).

2-53. Synthesis of 6-(5-chlorofuran-2-yl)-11-methylindolizino[3,2-c]quinoline (IQ 53: Formula 15)

A desired compound was obtained by the method of Example 2-1, except that a 2-(8-methylindolizine-2-yl)aniline compound was used instead of a 2-(indolizine-2-yl)aniline compound, and 5-chlorofuran-2-carbaldehyde was used instead of 4-bromobenzaldehyde.

Orange solid, ¹H NMR (300 MHz, CDCl₃) δ 8.35 (dd, J=7.7, 1.1 Hz, 1H), 8.22 (d, J=7.9 Hz, 1H), 8.03 (d, J=7.1 Hz, 1H), 7.70-7.58 (m, 2H), 7.22 (s, 1H), 7.02 (d, J=3.3 Hz, 1H), 6.90 (d, J=6.6 Hz, 1H), 6.57 (t, J=6.9 Hz, 1H), 6.49 (d, J=3.3 Hz, 1H), 2.57 (s, 1H).

2-54. Synthesis of 6-(4-methoxyphenyl)-12-((trimethylsilyl)ethynyl)indolizino[3,2-c]quinoline (IQ 54)

0.11 mmol of the IQ 50 compound, 0.13 mmol (1.2 equiv.) of tirmethyl((tributylstannyl)ethynyl)silane and Pd(PPh₃)₄, 0.01 mmol (0.1 equiv.) of CuI were dissolved in 3 mL of tetrahydrofuran to allow a reaction at 80° C. for 2 hours. After the reaction, the reaction mixture was washed with 3 mL of water, and an aqueous layer was extracted again with 3 mL of dichloromethane. An organic layer was collected and dehydrated with magnesium sulfate, and concentrated under reduced pressure. The concentrated reaction mixture was purified by silica gel column chromatography using a solvent mixture (hexane:ethylacetate:dichloromethane=3:1:2), thereby obtaining a desired compound.

Yellow solid, ¹H NMR (300 MHz, CDCl₃) δ 9.32 (dd, J=8.1, 1.1 Hz, 1H), 8.23 (dd, J=8.4, 1.3 Hz, 1H), 7.91 (dd, J=8.8, 0.9 Hz, 1H), 7.86 (dt, J=7.3, 1.1 Hz, 1H), 7.74-7.60 (m, 3H), 7.56 (d, J=8.8 Hz, 2H), 7.19 (dd, J=9.0, 6.6 Hz, 1H), 7.11 (d, J=8.6 1H), 6.52 (td, J=7.1, 1.5 Hz, 1H), 3.92 (s, 3H), 0.39 (s, 9H).

2-55. Synthesis of 12-ethynyl-6-(4-methoxyphenyl)indolizino[3,2-c]quinoline (IQ 55: Formula 16)

0.12 mmol of the IQ 54 compound and 0.24 mmol (2 equiv.) of K₂CO₃ were dissolved in 1 mL of methanol to allow a reaction at room temperature for 3 hours. After the reaction, the reaction mixture was washed with 3 mL of water, and an aqueous layer was extracted again with 3 mL of dichloromethane. An organic layer was collected and dehydrated with magnesium sulfate, and concentrated under reduced pressure. The concentrated reaction mixture was purified by silica gel column chromatography using a solvent mixture (hexane:ethylacetate:dichloromethane=3:1:2), thereby obtaining a desired compound.

Yellow solid, ¹H NMR (300 MHz, CDCl₃) δ 9.29 (d, J=8.0 Hz, 1H), 8.23 (d, J=7.9 Hz, 1H), 7.93 (d, J=7.3 Hz, 1H), 7.86 (d, J=9.0 Hz, 1H), 7.74-7.61 (m, 2H), 7.57 (d, J=8.6 Hz, 2H), 7.22-7.17 (m, 1H), 7.12 (d, J=8.6 Hz, 2H), 6.54 (t, J=6.9 Hz, 1H), 3.92 (s, 3H), 3.73 (s, 1H).

2-56. Synthesis of 4-(5-(indolizino[3,2-c]quinolin-6-yl)-2-methoxybenzyl)morpholine (IQ 56: Formula 17)

A desired compound was obtained by the method of Example 2-1, except that 4-methoxy-3-(morpholinomethyl)benzaldehyde was used instead of 4-bromobenzaldehyde.

Yellow solid, ¹H NMR (300 MHz, CDCl₃) δ 8.36 (d, J=7.7 Hz, 1H), 8.22 (d, J=8.3 Hz, 1H), 7.92 (d, J=7.3 Hz, 1H), 7.70-7.55 (m, 5H), 7.27 (s, 1H), 7.09 (d, J=8.4 Hz, 1H), 7.01 (dd, J=9.1, 6.5 Hz, 1H), 6.37 (t, J=6.9 Hz, 1H), 3.94 (s, 3H), 3.65-3.62 (m, 6H), 2.53-2.50 (m, 4H).

2-57. Synthesis of ethyl 6-(4-methoxy-3-(morpholinomethyl)phenyl)indolizino[3,2-c]quinoline-12-carboxylate (IQ 57: Formula 18)

A desired compound was obtained by the method of Example 2-1, except that an ethyl 2-(2-aminophenyl)indolizine-1-carboxylate compound was used instead of a 2-(indolizine-2-yl)aniline compound, and 4-methoxy-3-(morpholinomethyl)benzaldehyde was used instead of 4-bromobenzaldehyde.

Yellow solid, ¹H NMR (500 MHz, CDCl₃) δ 9.65 (d, J=8.4 Hz, 1H), 8.47 (d, J=9.3 Hz, 1H), 8.22 (d, J=8.2 Hz, 1H), 8.06 (d, J=7.2 Hz, 1H), 7.71 (t, J=7.5 Hz, 1H), 7.63 (t, J=7.6 Hz, 1H), 7.58 (d, J=1.8 Hz, 1H), 7.53 (dd, J=8.3, 2.0 Hz, 1H), 7.31 (t, J=9.0 Hz, 1H), 7.08 (d, J=8.4 Hz, 1H), 6.56 (d, J=6.8 Hz, 1H), 4.58 (q, J=7.1 Hz, 2H), 3.93 (s, 3H), 3.70-3.55 (m, 6H), 2.50 (s, 4H), 1.54 (t, J=7.1 Hz, 3H).

2-58. Synthesis of 6-(1H-indol-7-yl)indolizino[3,2-c]quinoline (IQ 58)

A desired compound was obtained by the method of Example 2-1, except that 1H-indole-7-carbaldehyde was used instead of 4-bromobenzaldehyde.

Yellow solid, ¹H NMR (300 MHz, CD₃OD) δ 8.52 (dd, J=7.0, 2.6 Hz, 1H), 8.13 (dd, J=7.8, 2.8 Hz, 1H), 7.87 (dd, J=7.1, 2.0 Hz, 1H), 7.75-7.66 (m, 3H), 7.46 (s, 1H), 7.41 (d, J=6.2 Hz, 1H), 7.37-7.30 (m, 2H), 7.19 (d, J=3.1 Hz, 1H), 7.08 (dd, J=9.5, 7.0 Hz, 1H), 6.63 (d, J=3.1 Hz, 1H), 6.31 (t, J=7.0 Hz, 1H).

2-59. Synthesis of 12-(1-butyl-1H-1,2,3-triazol-4-yl)-6-(4-methoxyphenyl)indolizino[3,2-c]quinoline (IQ 6-T)

0.13 mmol of the IQ 55 compound, 0.13 mmol (1 equiv.) of butylazide and 0.06 mmol (0.44 equiv.) of sodium ascorbate, and 0.03 mmol (0.22 equiv.) of $CuSa_4.5H_2O$ were dissolved in 3 mL of tetrahydrofuran/t-butanol/water to allow a reaction at room temperature for 12 hours. After the reaction, the reaction mixture was washed with 3 mL of water, and an aqueous layer was extracted again with 3 mL of dichloromethane. An organic layer was collected and dehydrated with magnesium sulfate, and concentrated under reduced pressure. The concentrated reaction mixture was purified by silica gel column chromatography using a solvent mixture (hexane:ethylacetate:dichloromethane=1:1:1), thereby obtaining a desired compound.

Yellow solid, $^1$H NMR (300 MHz, $CDCl_3$) δ 8.29 (d, J=8.2 Hz, 1H), 7.97 (d, J=7.1 Hz, 1H), 7.84 (s, 1H), 7.68-7.62 (m, 4H), 7.43 (t, J=7.8 Hz, 1H), 7.15 (d, J=8.6 Hz, 2H), 6.54 (t, J=7.0 Hz, 1H), 4.57 (t, J=7.2 Hz, 2H), 3.93 (s, 3H), 2.06 (quint, J=7.3 Hz, 2H), 1.56-1.44 (m, 2H), 1.04 (t, J=7.4 Hz, 3H).

2-60. Synthesis of N-(2-(2-(2-(2-(4-(6-(4-methoxyphenyl)indolizino[3,2-c]quinolin-12-yl)-1H-1,2,3-triazol-1-yl)ethoxy)ethoxy)ethyl)-6-((3aS,6aR)-5-oxido-2-oxohexahydro-1H-thieno[3,4-d]imidazol-4-yl)hexanamide (IQ 6-T-B)

0.13 mmol of the IQ 55 compound, 0.13 mmol (1 equiv.) of biotin azide and 0.06 mmol (0.44 equiv.) of sodium ascorbate, and 0.03 mmol (0.22 equiv.) of $CuSO_4.5H_2O$ were dissolved in 3 mL of tetrahydrofuran/t-butanol/water to allow a reaction at room temperature for 24 hours. After the reaction, the reaction mixture was washed with 3 mL of water, and an aqueous layer was extracted again with 3 mL of dichloromethane. An organic layer was collected and dehydrated with magnesium sulfate, and concentrated under reduced pressure. The concentrated reaction mixture was purified by silica gel column chromatography using a solvent mixture (chloroform:methanol=10:1), thereby obtaining a desired compound.

Yellow solid, $^1$H NMR (300 MHz, $CDCl_3$) δ 8.40 (d, J=8.4 Hz, 1H), 8.35 (d, J=8.0 Hz, 1H), 8.27 (s, 1H), 8.16 (d, J=7.2 Hz, 1H), 7.84-7.75 (m, 5H), 7.56 (t, J=7.4 Hz, 1H), 7.48 (t, J=8.6 Hz, 1H), 6.84 (t, J=6.4 Hz, 1H), 4.78 (t, J=4.7 Hz, 2H), 4.55-4.48 (m, 2H), 4.03 (t, J=4.8 Hz, 2H), 3.95 (s, 3H), 3.71-3.69 (m, 2H), 3.60-3.58 (m, 2H), 3.45 (t, J=4.3 Hz, 2H), 3.40 (t, J=2.9 Hz, 3H), 3.32 (t, J=4.2 Hz, 2H), 3.23-3.18 (m, 4H), 3.08-3.05 (m, 1H), 2.98-2.91 (m, 2H).

2-61. Synthesis of 2,6-bis(indolizino[3,2-c]quinolin-6-yl)pyridine (IQ 5-D: Formula 19)

A desired compound was obtained by the method of Example 2-1, except that pyridine-2,6-dicarbaldehyde was used instead of 4-bromobenzaldehyde.

Yellow solid, $^1$H NMR (300 MHz, $CDCl_3$) δ 8.49 (d, J=7.3 Hz, 2H), 8.38 (d, J=7.3 Hz, 2H), 8.33-8.26 (m, 6H), 7.76-7.62 (m, 5H), 7.51 (d, J=9.0 Hz, 2H), 6.92 (t, J=9.7 Hz, 2H), 6.31 (t, J=6.9 Hz, 2H).

2-62. Synthesis of 6-(4-methoxyphenyl)-5-methylindolizino[3,2-c]quinolin-5-ium methyl sulfate (IQ 6-S1-Me: Formula 20)

0.06 mmol of the IQ 6 compound was dissolved in 2 mL of chloroform and mixed with 0.06 mmol (1 equiv.) of dimethylsulfate to allow a reaction at 60° C. for 36 hours. After the reaction, the reaction mixture was concentrated under reduced pressure, thereby obtaining a desired compound.

$^1$H NMR (300 MHz, $D_2O$) δ 8.14 (dd, J=8.1, 1.2 Hz, 1H), 7.86 (d, J=8.4 Hz, 1H), 7.68 (td, J=6.9, 1.5 Hz, 1H), 7.59 (t, J=6.9 Hz, 1H), 7.49 (d, J=9.3 Hz, 1H), 7.41-7.34 (m, 4H), 7.33-7.29 (m, 1H), 7.06 (s, 1H), 6.97 (d, J=7.2 Hz, 1H), 6.57 (dd, J=7.2, 1.2 Hz, 1H), 3.96 (s, 3H), 3.84 (s, 3H).

2-63. Synthesis of 5-(2-chloroethyl)-6-(4-methoxyphenyl)indolizino[3,2-c]quinolin-5-ium trifluoromethanesulfonate (IQ6-S2-Cl: Formula 21)

0.06 mmol of the IQ 6 compound was dissolved in 2 mL of acetonitrile and mixed with 0.3 mmol (5 equiv.) of 2-chloroethyl trifluoromethanesulfonate to allow a reaction at 80° C. for 36 hours. After the reaction, the reaction mixture was concentrated under reduced pressure. The concentrated reaction mixture was purified by silica gel column chromatography using a solvent mixture (methanol:dichloromethane=1:20), thereby obtaining a desired compound.

$^1$H NMR (300 MHz, $CDCl_3$) δ 8.54 (dd, J=8.3, 1.5 Hz, 1H), 8.27 (d, J=8.4 Hz, 1H), 7.96 (td, J=7.2, 1.5 Hz, 1H), 7.90 (d, J=9.0 Hz, 1H), 7.81 (t, J=7.2 Hz, 1H), 7.62 (d, J=8.7 Hz, 2H), 7.58-7.55 (m, 2H), 7.35 (d, J=8.7 Hz, 2H), 7.16 (d, J=7.5 Hz, 1H), 6.81 (td, J=7.2, 1.2 Hz, 1H), 5.09 (t, J=6.3 Hz, 2H), 4.02 (s, 3H), 3.97 (t, J=6.3 Hz, 2H).

2-64. Synthesis of 12-ethynyl-6-(p-tolyl)indolizino[3,2-c]quinoline (IQ 64)

0.1 mmol of a 6-(p-tolyl)-12-((trimethylsilyl)ethynyl)indolizino[3,2-c]quinoline compound and 0.2 mmol (2 equiv.) of potassium carbonate ($K_2CO_3$) were dissolved in 4 mL of methanol to allow a reaction at room temperature for 16 hours. After the reaction, the reaction mixture was washed with water, and an aqueous layer was extracted with dichloromethane three times. An organic layer was collected and dehydrated with sodium sulfate, and concentrated under reduced pressure. The concentrated reaction mixture was purified by silica gel column chromatography using a solvent mixture (ethylacetate:hexane:dichloromethane=1:10:2), thereby obtaining a desired compound (14 mg, 47%).

Yellow solid; $^1$H NMR (300 MHz, $CDCl_3$) δ 9.29 (dd, J=7.7, 1.6 Hz, 1H), 8.23 (dd, J=8.1, 1.1 Hz, 1H), 7.87 (tt, J=8.3, 1.1 Hz, 2H), 7.71 (td, J=7.5, 1.5 Hz, 1H), 7.64 (td, J=7.5, 1.5 Hz, 1H), 7.51 (d, J=8.1 Hz, 2H), 7.40 (d, J=7.7 Hz, 2H), 7.17 (dd, J=9.0, 6.6 Hz, 1H), 6.51 (td, J=6.9, 1.5 Hz, 1H), 3.72 (s, 1H), 2.49 (s, 3H); ESI-MS m/z 333 (M+H)$^+$.

2-65. Synthesis of 6-(4-methoxyphenyl)indolizino[3,2-c]quinoline-10-carbonitrile (IQ 67: Formula 22)

10-bromo-6-(4-methoxyphenyl)indolizino[3,2-c]quinoline (63 mg, 0.156 mmol) was dissolved in 4 mL of dimethylformamide and mixed with CuCN (1.252 mmol, 8 equiv.) and NaI (0.313 mmol, 2 equiv.) to allow a reaction at 150° C. for 16 hours. After the reaction, work-up was performed with H₂O and dichloromethane, and the reaction mixture was purified by silica gel column chromatography using a solvent mixture (hexane:ethylacetate:dichloromethane=5:1:2), thereby obtaining a desired compound (47%, 25.5 mg).

Yellow solid; $^1$H NMR (300 MHz, CDCl$_3$) δ 8.36 (dd, J=7.8, 1.5 Hz, 1H), 8.25 (d, J=7.7 Hz, 1H), 8.05 (s, 1H), 7.97 (d, J=7.3 Hz, 1H), 7.73 (td, J=7.5, 1.5 Hz, 1H), 7.66 (td, J=7.5, 1.2 Hz, 1H), 7.58 (d, J=8.6, 2H), 7.52 (s, 1H), 7.13 (d, J=8.6 Hz, 1H), 6.48 (dd, J=7.5, 1.7 Hz, 1H), 3.93 (s, 3H); ESI-MS m/z 350 (M+H)⁺.

2-66. Synthesis of 6-(5-bromothiophen-2-yl)indolizino[3,2-c]quinoline-12-amine (IQ 72)

6-(5-bromothiophen-2-yl)-12-nitroindolizino[3,2-c]quinoline (30 mg, 0.071 mmol) was dissolved in 0.6 mL of dimethylformamide and mixed with SnCl₂.2H₂O (0.707 mmol, 10 equiv.) to allow a reaction at room temperature for 18 hours. After the reaction, work-up was performed with H₂O and dichloromethane, and the reaction mixture was purified by silica gel column chromatography using a solvent mixture (hexane:ethylacetate:dichloromethane=3:1:2), thereby obtaining a desired compound (93%, 27.2 mg).

Yellow solid; $^1$H NMR (300 MHz, CDCl$_3$) δ 8.85 (dd, J=7.5, 2.4 Hz, 1H), 8.23-8.18 (m, 2H), 7.71-7.61 (m, 2H), 7.57 (d, J=9.0 Hz, 1H), 7.21 (d, J=3.9 Hz, 1H), 7.16 (d, J=3.6 Hz, 1H), 7.00 (dd, J=9.3, 6.3 Hz, 1H), 6.48 (td, J=7.5, 1.2 Hz, 1H), 3.54 (bs, 2H).

2-67. Synthesis of 4-(indolizino[3,2-c]quinolin-6-yl)benzene-1,2-diamine (IQ 76)

6-(3,4-dinitrophenyl)indolizino[3,2-c]quinoline (40 mg, 0.103 mmol) was dissolved in 8 mL of dimethylformamide and mixed with SnCl₂.2H₂O (1.030 mmol, 10 equiv.) to allow a reaction at 80° C. for 4 hours. After the reaction, work-up was performed with H₂O and dichloromethane:methanol=9:1, and the reaction mixture was purified by silica gel column chromatography using a solvent mixture (dichloromethane:methanol=15:1), thereby obtaining a desired compound (37%, 12.3 mg).

Yellow solid; $^1$H NMR (300 MHz, CDCl$_3$) δ 8.34 (dd, J=7.9, 1.7 Hz, 1H), 8.22 (d, J=8.1 Hz, 1H), 8.04 (d, J=7.3 Hz, 1H), 7.68-7.55 (m, 3H), 7.27 (s, 1H), 7.03-6.84 (m, 4H), 6.41 (td, J=7.3, 1.2 Hz, 1H), 3.25 (bs, 4H); ESI-MS m/z 325 (M+H)⁺.

2-68. Synthesis of 6-(4-methoxyphenyl)benzo[7,8]indolizino[3,2-c]quinoline (IQ 77: Formula 23)

A desired compound (59%, 36.6 mg) was obtained by the method of Example 2-1, except that a 2-(pyrrolo[2,1-a]isoquinoline-2-yl)aniline compound was used instead of a 2-(indolizine-2-yl)aniline compound, and 4-methoxybenzaldehyde was used instead of 4-bromobenzaldehyde.

Yellow solid; $^1$H NMR (300 MHz, CDCl$_3$) δ 8.41 (dd, J=7.7, 1.5 Hz, 1H), 8.33 (d, J=7.7 Hz, 1H), 8.25 (dd, J=7.9, 1.5 Hz, 1H), 7.82 (s, 1H), 7.72-7.48 (m, 8H), 7.13 (d, J=8.4 Hz, 1H), 6.62 (d, J=7.7 Hz, 1H), 3.93 (s, 3H); ESI-MS m/z 375 (M+H)⁺.

2-69. Synthesis of 6-ethylbenzo[7,8]indolizino[3,2-c]quinoline (IQ 79: Formula 24)

A desired compound (40%, 14.8 mg) was obtained by the method of Example 2-1, except that a 2-(pyrrolo[2,1-a]isoquinoline-2-yl)aniline compound was used instead of a 2-(indolizine-2-yl)aniline compound, and propionaldehyde was used instead of 4-bromobenzaldehyde.

Yellow solid; $^1$H NMR (300 MHz, CDCl$_3$) δ 8.51 (d, J=7.5 Hz, 1H), 8.35-8.31 (m, 2H), 8.12 (d, J=8.0 Hz, 1H), 7.77 (s, 1H), 7.69-7.52 (m, 5H), 6.96 (d, J=7.7 Hz, 1H), 3.52 (q, J=7.5 Hz, 2H), 1.57 (t, J=7.5 Hz, 3H); ESI-MS m/z 297 (M+H)⁺.

2-70. Synthesis of 4-(indolizino[3,2-c]quinolin-6-yl)aniline (IQ-B1: Formula 25)

0.12 mmol of the 6-(4-nitrophenyl)indolizino[3,2-c]quinoline (IQ2) compound and 0.60 mmol (5 equiv.) of tin chloride dihydrate (SnCl₂.2H₂O) were dissolved in 5 mL of ethanol to allow a reaction at 80° C. for 2 hours. After the reaction, the reaction mixture was washed with a saturated sodium hydrogen carbonate solution (Sat'd NaHCO₃), and an aqueous layer was extracted with dichloromethane three times. An organic layer was collected, dehydrated with sodium sulfate, and concentrated under reduced pressure. The concentrated reaction mixture was purified by silica gel column chromatography using a solvent mixture (dichloromethane:methanol=40:1), thereby obtaining a desired compound (30 mg, 80%).

Yellow solid; $^1$H NMR (300 MHz, CDCl$_3$) δ 8.34 (dd, J=7.8, 1.5 Hz, 1H), 8.22 (d, J=8.1 Hz, 1H), 8.05 (d, J=7.3 Hz, 1H), 7.66 (td, J=7.5, 1.5 Hz, 1H), 7.61-7.55 (m, 2H), 7.45 (d, J=8.3 Hz, 2H), 7.23 (s, 1H), 7.01 (dd, J=9.0. 6.3 Hz, 1H), 6.87 (d, J=8.3 Hz, 2H), 6.41 (dd, J=7.5, 0.9 Hz, 1H), 3.89 (bs, 2H); ESI-MS m/z 310 (M+H)⁺.

2-71. Synthesis of 4-(indolizino[3,2-c]quinolin-6-yl)phenol (IQ-B2: Formula 26)

A desired compound (10%, 6 mg) was obtained by the method of Example 2-1, except that 4-hydroxylbenzaldehyde was used instead of 4-bromobenzaldehyde.

Yellow solid; $^1$H NMR (300 MHz, DMSO-d$_6$) δ 9.91 (s, 1H), 8.49 (dd, J=7.8, 1.5 Hz, 1H), 8.04 (d, J=7.5 Hz, 1H), 7.96 (d, J=7.5 Hz, 1H), 7.81 (d, J=8.7 Hz, 1H), 7.71-7.60 (m, 2H), 7.51 (s, 1H), 7.47 (d, J=8.7 Hz, 2H), 7.18 (dd, J=9.0, 6.6 Hz, 1H), 7.01 (d, J=8.7, 2H), 6.68 (t, J=6.6 Hz, 1H); ESI-MS m/z 311 (M+H)⁺.

2-72. Synthesis of (E)-6-styrylindolizino[3,2-c]quinoline (IQ-B4)

A desired compound (12 mg, 28%) was obtained by the method of Example 2-1, except that trans-cynamaldehyde was used instead of 4-bromobenzaldehyde.

Yellow solid; $^1$H NMR (300 MHz, CDCl$_3$) δ 8.91 (d, J=7.8 Hz, 1H), 8.33 (dd, J=7.5, 0.9 Hz, 1H), 8.24 (d, J=8.4 Hz), 7.90, 7.81 (ABq, J$_{AB}$=15.8, 2H), 7.74-7.65 (m, 4H), 7.59 (td, J=7.2, 1.5 Hz, 1H), 7.49-7.36 (m, 3H), 7.25 (s, 1H), 7.10 (dd, J=8.7, 6.6 Hz, 1H), 6.73 (td, J=6.9, 1.5 Hz, 1H); ESI-MS m/z 321 (M+H)⁺.

2-73. Synthesis of 6-(p-tolypindolizino[3,2-c]quinolin-12-amine (IQ-135)

0.32 mmol of the 6-(p-tolypindolizino[3,2-c]quinoline (IQ 3) compound was dissolved in 2 mL of acetic acid (CH₃COOH), and at 0° C., 0.03 mmol (0.1 equiv.) of sulfuric acid (conc. H₂SO₄) and 0.03 mmol (0.1 equiv.) of nitric acid (60% HNO₃) were slowly added. 0.3 mL of sulfuric acid was further added, and then a reaction was performed at room temperature for 3 hours. After the reaction, the reaction mixture was washed with a saturated sodium hydrogen carbonate solution (Sat'd NaHCO$_3$), and an aqueous layer was extracted with dichloromethane three times. An organic layer was collected, dehydrated with sodium sulfate, and concentrated under reduced pressure. The concentrated reaction mixture was purified by silica gel column chromatography using a solvent mixture (ethylacetate:hexane:dichloromethane=1:5:1), thereby obtaining a compound 12-nitro-6-(p-tolypindolizino[3,2-c]quinoline (88 mg, 78%).

0.12 mmol of the 12-nitro-6-(p-tolypindolizino[3,2-c]quinoline compound and 0.60 mmol (5 equiv.) of tin chloride dihydrate (SnCl$_2$.2H$_2$O) were dissolved in 5 mL of ethanol to allow a reaction at 80° C. for 2 hours. After the reaction, the reaction mixture was washed with a saturated sodium hydrogen carbonate solution (Sat'd NaHCO$_3$), and an aqueous layer was extracted with dichloromethane three times. An organic layer was collected, dehydrated with sodium sulfate, and concentrated under reduced pressure. The concentrated reaction mixture was purified by silica gel column chromatography using a solvent mixture (dichloromethane:methanol=20:1), thereby obtaining a desired compound (28 mg, 75%).

Reddish solid; $^1$H NMR (300 MHz, CDCl$_3$) δ 8.84 (dd, J=7.8, 1.8 Hz, 1H), 8.25 (dd, J=8.1, 1.5 Hz), 7.74 (d, J=7.2 Hz, 1H), 7.69-7.58 (m 2H), 7.54-7.50 (m, 3H), 7.39 (d, J=7.8, 2H), 6.90 (dd, J=9.0, 6.3, 1H). 6.30 (dd, J=7.5, 1.2, 1H), 3.52 (bs, 2H), 2.50 (s, 3H); ESI-MS m/z 324 (M+H)$^+$.

2-74. Synthesis of 6-(4-methoxyphenyl)indolizino[3,2-c]quinoline-10-carbaldehyde (IQ-B11: Formula 31)

0.04 mmol of a 10-bromo-6-(4-methoxyphenyl)indolizino[3,2-c]quinoline compound was substituted with nitrogen and then dissolved in anhydrous tetrahydrofuran, and at −78° C., normal-butyl lithium (n-BuLi) was added dropwise. After 15 minutes, anhydrous dimethylformamide (DMF) was added dropwise, and reacted at 78° C. for 1 hour. A saturated ammonium chloride solution (Sat'd NH$_4$Cl) was added to terminate the reaction, the reaction mixture was extracted with dichloromethane three times, and an organic layer was collected, dehydrated with sodium sulfate and then concentrated under reduced pressure. The concentrated reaction mixture was purified by silica gel column chromatography using a solvent mixture (ethylacetate:hexane:dichloromethane=1:5:5), thereby obtaining a desired compound (3 mg, 23%).

Orange solid; $^1$H NMR (300 MHz, CDCl$_3$) δ 9.96 (s, 1H), 8.41 (dd, J=7.8, 1.5 Hz, 1H), 8.27 (dd, J=7.8, 1.2 Hz, 1H), 8.18 (s, 1H), 8.10 (d, J=7.5 Hz, 1H), 7.74 (td, J=7.5, 1.8 Hz, 1H), 7.71-7.61 (m, 4H), 7.16 (dt, J=9.0, 2.1 Hz, 2H), 6.91 (dd, J=7.2, 1.2 Hz, 1H); ESI-MS m/z 353 (M+H)$^+$.

2-75. Synthesis of (E)-6-(4-methoxystyryl)indolizino[3,2-c]quinoline (IQ-B12:Formula 32)

A desired compound was obtained by the method of Example 2-1, except that 4-methoxy-trans-cynamaldehyde was used instead of 4-bromobenzaldehyde.

Brown solid; $^1$H NMR (300 MHz, CDCl$_3$) δ 8.90 (d, J=7.2 Hz, 1H), 8.31 (d, J=8.1 Hz, 1H), 8.22 (d, J=8.1 Hz, 1H), 7.78, 7.72 (ABq, J$_{AB}$=14.1 Hz, 2H), 7.69-7.63 (m, 4H), 7.57 (t, J=6.9 Hz, 1H), 7.22 (s, 1H), 7.07 (dd, J=8.7, 7.2 Hz, 1H), 6.98 (d, J=9.0 Hz, 2H), 6.70 (td, J=7.5, 1.2 Hz, 1H), 3.87 (s, 3H); ESI-MS m/z 351 (M+H)$^+$.

2-76. Synthesis of (E)-6-((2-methyl-2-phenylhydrazineylidene)methyl)indolizino[3,2-c]quinoline (IQ-B16)

A desired compound (12 mg, 18%) was obtained by the method of Example 2-1, except that (E)-2-(2-methyl-2-phenylhydrazineylidene)acetaldehyde was used instead of 4-bromobenzaldehyde.

Reddish solid; $^1$H NMR (300 MHz, CDCl$_3$) δ 10.0 (dd, J=7.5, 0.9 Hz, 1H), 8.35 (dd, J=8.1, 1.2 Hz, 1H), 8.15 (s, 1H), 8.13 (s, 1H), 7.71-7.57 (m, 3H), 7.43-7.33 (m, 4H), 7.31 (s, 1H), 7.10 (dd, J=8.7, 6.5 Hz, 1H), 7.00 (t, J=7.2 Hz, 1H), 6.53 (td, J=7.8, 1.2 Hz, 1H), 3.67 (s, 3H); ESI-MS m/z 351 (M+H)$^+$.

2-77. Synthesis of (E)-6-(4-methoxyphenyl)-10-styrylindolizino[3,2-c]quinoline (IQ-B19: Formula 27)

0.05 mmol of the 10-bromo-6-(4-methoxyphenyl)indolizino[3, 2-c]quinoline compound, 0.0025 mmol (0.05 equiv.) of tetrakis(triphenylphosphine)palladium (Pd(PPh$_3$)$_4$), 0.15 mmol (3 equiv.) of potassium carbonate (K$_2$CO$_3$) and 0.075 mmol (1.5 equiv.) of styrene were dissolved in 2 mL of anhydrous dimethylformamide to allow a reaction at 120° C. for 12 hours. After the reaction, the reaction mixture was washed with water, and an aqueous layer was extracted with dichloromethane three times. An organic layer was collected, dehydrated with sodium sulfate and concentrated under reduced pressure. The concentrated reaction mixture was purified by silica gel column chromatography using a solvent mixture (ethylacetate:hexane=1:3), thereby obtaining a desired compound (6 mg, 28%).

Yellow solid; $^1$H NMR (300 MHz, CDCl$_3$) δ 8.37 (dd, J=8.1, 1.2 Hz, 1H), 8.25 (d, J=8.4 Hz, 1H), 7.88 (d, J=7.8 Hz, 1H), 7.72-7.58 (m, 5H), 7.52 (d J=7.2 Hz, 2H), 7.38 (t, J=6.3 Hz, 2H), 7.32-7.30 (m, 2H), 7.17-7.09 (m, 4H), 6.75 (dd, J=7.8, 1.2 Hz, 1H), 3.94 (s, 3H); ESI-MS m/z 427 (M+H)$^+$.

2-78. Synthesis of (E)-10-(2-(1H-imidazol-1-yl)vinyl)-6-(4-methoxyphenyl)indolizino[3,2-c]quinoline (IQ-B20: Formula 28)

A desired compound (2 mg, 10%) was obtained by the method of Example 2-1 (IQ19), except that 1-vinylimidazole was used instead of styrene.

Yellow solid; $^1$H NMR (300 MHz, CDCl$_3$) δ 8.37 (dd, J=8.1, 1.2 Hz, 1H), 8.25 (d, J=8.1 Hz, 1H), 7.90 (d, J=7.8 Hz, 1H), 7.77 (s, 1H), 7.70 (td, J=6.7, 1.5 Hz, 1H), 7.65-7.61 (m, 3H), 7.55 (s, 1H), 7.36 (d, J=14.1 Hz, 1H), 7.31-7.29 (m, 2H), 7.23-7.14 (m, 3H), 6.71 (d, J=14.7 Hz, 1H), 6.55 (dd, J=7.5, 2.3 Hz, 1H), 3.95 (s, 3H); ESI-MS m/z 417 (M+H)$^+$.

2-79. Synthesis of 4-(6-(4-methoxyphenyl)indolizino[3,2-c]quinolin-10-yl)benzaldehyde (IQ-B23: Formula 29)

0.05 mmol of the 10-bromo-6-(4-methoxyphenyl)indolizino[3,2-c]quinoline, 0.0025 mmol (0.05 equiv.) of bis (triphenylphosphine)palladium chloride (PdCl$_2$(PPh$_3$)$_2$), 0.053 mmol (1.05 equiv.) of potassium carbonate (K$_2$CO$_3$) and 4-formylphenylboronic acid) were dissolved in 2 mL of a solvent mixture (tetrahydrofuran:water=10:1) to allow a reaction at 80° C. for 16 hours. After the reaction, the reaction mixture was washed with water, and an aqueous layer was extracted with dichloromethane three times. An organic layer was collected, dehydrated with sodium sulfate, and concentrated under reduced pressure. The concentrated reaction mixture was purified by silica gel column chromatography using a solvent mixture (ethylacetate:hexane=1:3), thereby obtaining a desired compound (30 mg, 70%).

Orange solid; $^1$H NMR (300 MHz, CDCl$_3$) δ 10.07 (s, 1H), 8.39 (d, J=7.8 Hz, 1H), 8.28 (d, J=8.1 Hz, 1H), 8.02 (d, J=7.5 Hz, 1H), 7.98 (d, J=8.1 Hz, 2H), 7.94 (s, 1H), 7.82 (d, J=8.4 Hz, 2H), 7.72 (td, J=6.9, 1.2 Hz, 1H), 7.67-7.62 (m, 3H), 7.41 (s, 1H), 7.16 (d, J=8.7 Hz, 2H), 6.78 (dd, J=7.5, 1.2 Hz, 1H), 3.96 (s, 3H); ESI-MS m/z 429 (M+H)$^+$.

2-80. Synthesis of (E)-3-(6-(4-methoxyphenyl)indolizino[3,2-c]quinolin-10-yl)acrylaldehyde (IQ-B25: Formula 30)

0.016 mmol of the 10-bromo-6-(4-methoxyphenyl)indolizino[3,2-c]quinoline compound, 0.31 mmol (2 equiv.) of tetrabutylammonium acetate (Bu$_4$NOAc), 0.16 mmol (1 equiv.) of potassium chloride, 0.23 mmol (1.5 equiv.) of potassium carbonate, 0.005 mmol (0.03 equiv.) of palladium acetate (Pd(OAc)$_2$) and 0.47 mmol (3 equiv.) of acrolein dimethyl acetal were dissolved in 4 mL of anhydrous dimethylformamide to allow a reaction at 90° C. for 2 hours. The reaction product was cooled to room temperature, 5 mL of 2N hydrochloric acid was slowly added dropwise, and the reaction was further performed at room temperature for 1 hour. The reaction was terminated, a saturated sodium hydrogen carbonate solution (Sat'd NaHCO$_3$) was added to the reaction product to be changed to a basic condition, and then extracted with dichloromethane three times. An organic layer was collected, dehydrated with sodium sulfate and concentrated under reduced pressure. The concentrated reaction mixture was purified by silica gel column chromatography using a solvent mixture (ethylacetate:hexane:dichloromethane=1:5:1), thereby obtaining a desired compound (8 mg, 13%).

Reddish solid, $^1$H NMR (300 MHz, CDCl$_3$) δ 9.74 (d, J=7.8 Hz, 1H), 8.38 (dd, J=8.1, 1.8 Hz, 1H), 8.27 (d, J=7.8 Hz, 1H), 7.95 (d, J=7.8 Hz, 1H), 7.80 (s, 1H), 7.73 (td, J=6.9, 1.5 Hz, 1H), 7.68-7.58 (m, 3H), 7.48 (s, 1H), 7.44 (d, J=15.6 Hz, 1H), 7.15 (d, J=8.4 Hz, 2H), 6.68-6.61 (m, 2H), 3.95 (s, 3H); ESI-MS m/z 379 (M+H)$^+$.

2-81. Synthesis of (E)-3-(4-(6-(4-methoxyphenyl)indolizino[3,2-c]quinolin-10-yl)phenyl)acrylaldehyde (IQ-B31: Formula 34)

A desired compound (13 mg, 57%) was obtained by the method of Example 2-1 (IQ23), except that (E)-(4-(3-oxoprop-1-en-1-yl)phenyl)sp acid) was used instead of 4-formylphenylboronic acid.

Reddish solid, $^1$H NMR (300 MHz, CDCl$_3$) δ 9.73 (d, J=7.8 Hz, 1H), 8.38 (d, J=7.5 Hz, 1H), 8.26 (d, J=8.1 Hz, 1H), 8.00 (d, J=7.8 Hz, 1H), 7.89 (s, 1H), 7.73-7.60 (m, 8H), 7.49 (d, J=15.9 Hz, 1H), 7.36 (s, 1H), 7.15 (d, J=8.7 Hz, 2H), 6.80-6.72 (m, 2H), 3.95 (s, 3H); ESI-MS m/z 455 (M+H)$^+$.

2-82. Synthesis of 4-(6-(4-methoxyphenyl)indolizino[3,2-c]quinolin-10-yl)-N-phenylbenzamide (IQ-B35: Formula 36)

A desired compound (11 mg, 50%) was obtained by the method of Example 2-1 (IQ23), except that 4-(phenylcarbamoylphenyl)boronic acid was used instead of 4-formylphenylboronic acid.

Yellow solid, $^1$H NMR (300 MHz, CDCl$_3$) δ 8.38 (d, J=7.8 Hz, 1H), 8.28 (d, J=7.8 Hz, 1H), 8.01-7.94 (m, 4H), 7.89 (s, 1H), 7.75-7.61 (m, 8H), 7.42-7.37 (m, 3H), 7.20-7.314 (m, 3H), 6.76 (dd, J=7.8, 1.5 Hz, 1H), 3.95 (s, 3H); ESI-MS m/z 520 (M+H)$^+$.

2-83. N,N-diethyl-4-(6-(4-methoxyphenyl)indolizino[3,2-c]quinolin-10-yl)benzamide (IQ-B36: Formula 37)

A desired compound (4 mg, 19%) was obtained by the method of Example 2-1 (IQ23), except that 4-(diethylcarbamoylphenyl)boronic acid was used instead of 4-formylphenylboronic acid.

Yellow solid; $^1$H NMR (300 MHz, CDCl$_3$) δ 8.40 (dd, J=7.8, 1.2 Hz, 1H), 8.34 (bs, 1H), 8.02 (d, J=7.2 Hz, 1H), 7.88 (s, 1H), 7.74-7.61 (m, 6H), 7.49 (d, J=8.1 Hz, 2H), 7.37 (s, 1H), 7.17 (d, J=9.0 Hz, 1H), 6.55 (d, J=6.0 Hz, 1H), 3.96 (s, 3H), 3.57 (bs, 2H), 3.33 (bs, 2H), 1.25 (bs, 3H), 1.18 (bs, 3H); ESI-MS m/z 500 (M+H)$^+$.

2-84. Synthesis of 4-(6-(4-methoxyphenyl)indolizino[3,2-c]quinolin-10-yl)-N,N-dimethylaniline (IQ-B37: Formula 35)

A desired compound (10 mg, 46%) was obtained by the method of Example 2-1 (IQ23), except that 4-(dimethylamino)phenylboronic acid was used instead of 4-formylphenylboronic acid.

Orange solid; $^1$H NMR (300 MHz, CDCl$_3$) δ 8.36 (dd, J=8.1, 1.5 Hz, 1H), 8.25 (d, J=8.1 Hz, 1H), 7.92 (d, J=7.5 Hz, 1H), 7.75 (s, 1H), 7.71-7.56 (m, 6H), 7.24 (s, 1H), 7.15 (d, J=8.4 Hz, 1H), 6.79 (d, J=8.7 Hz, 1H), 6.75 (dd, J=7.8, 1.8 Hz, 1H), 3.95 (s, 3H), 3.02 (s, 6H); ESI-MS m/z 444 (M+H)$^+$.

2-85. Synthesis of 6-(4-methoxyphenyl)-10-(naphthalen-2-yl)indolizino[3,2-c]quinoline (IQ-B39)

A desired compound (12 mg, 54%) was obtained by the method of Example 2-1 (IQ23), except that 2-naphthylboronic acid was used instead of 4-formylphenylboronic acid.

Yellow solid; $^1$H NMR (300 MHz, CDCl$_3$) δ 8.39 (dd, J=7.8, 1.5 Hz, 1H), 8.28 (d, J=7.8 Hz, 1H), 8.11 (s, 1H), 8.01 (d, J=7.8 Hz, 1H), 7.97 (s, 1H), 7.94 (d, J=8.7 Hz, 1H), 7.92-7.86 (m, 2H), 7.81 (dd, J=8.4, 1.5 Hz, 1H), 7.73-7.64 (m, 4H), 7.56-7.49 (m, 2H), 7.36 (s, 1H), 7.16 (d, J=8.7 Hz, 1H), 6.91 (dd, J=7.5, 1.8 Hz, 1H), 3.96 (s, 3H); ESI-MS m/z 451 (M+H)$^+$.

2-86. Synthesis of 4-(6-(4-methoxyphenyl)indolizino[3,2-c]quinolin-10-yl)benzonitrile (IQ-B43)

A desired compound (18 mg, 84%) was obtained by the method of Example 2-1 (IQ23), except that 4-cyanophenylboronic acid was used instead of 4-formylphenylboronic acid.

Orange solid; $^1$H NMR (300 MHz, CDCl$_3$) δ 8.37 (dd, J=8.1, 1.2 Hz, 1H), 8.26 (d, J=7.8 Hz, 1H), 8.01 (d, J=7.8 Hz, 1H), 7.34 (s, 1H), 7.87 (s, 1H), 7.74 (s, 4H), 7.71-7.62 (m, 4H), 7.39 (s, 1H), 7.15 (d, J=8.4 Hz, 1H), 7.00 (dd, J=7.8, 1.8 Hz, 1H), 3.95 (s, 3H); ESI-MS m/z 426 (M+H)$^+$.

2-87. Synthesis of (E)-3-(6-(4-methoxyphenyl)indolizino[3,2-c]quinolin-10-yl)acrylonitrile (IQ-B44)

A desired compound (2 mg, 11%) was obtained by the method of Example 2-1 (IQ19), except that acrylonitrile was used instead of styrene.

Yellow solid; ¹H NMR (300 MHz, CDCl₃) δ 8.37 (dd, J=8.1, 1.2 Hz, 1H), 8.30 (bs, 1H), 7.93 (d, J=7.5 Hz, 1H), 7.76-7.66 (m, 3H), 7.62 (d, J=6.6 Hz, 1H), 7.46 (s, 1H), 7.35 (d, J=16.5 Hz, 1H), 7.15 (d, J=6.6 Hz, 1H), 6.52 (dd, J=7.8, 1.6 Hz, 1H), 5.81 (d, J=16.5 Hz, 1H), 3.95 (s, 3H); ESI-MS m/z 376 (M+H)⁺.

2-88. Synthesis of 6-(4-(4,4,5,5-tetramethyl-1,3,2-dioxaborolan-2-yl)phenyl)indolizino[3,2-c]quinoline (IQ-B46)

A desired compound (25 mg, 17%) was obtained by the method of Example 2-1, except that 4-(4,4,5,5-tetramethyl-1,3,2-dioxaborolan-2-yl)-benzaldehyde was used instead of 4-bromobenzaldehyde.

Yellow solid; ¹H NMR (300 MHz, CDCl₃) δ 8.38 (dd, J=7.8, 1.5 Hz, 1H), 8.26 (d, J=7.8 Hz, 1H), 8.05 (d, J=7.8 Hz, 2H), 7.82 (d, J=7.5 Hz, 2H), 7.72-7.61 (m, 5H), 7.29 (s, 1H), 7.04 (dd, J=8.6, 6.8 Hz, 1H), 6.40 (td, J=6.8, 1.2 Hz, 1H), 1.42 (s, 12H); ESI-MS m/z 421 (M+H)⁺.

2-89. Synthesis of 6,10-bis(4-methoxyphenyl)indolizino[3,2-c]quinoline (IQ-B26:Formula 33)

A desired compound (11 mg, 50%) was obtained by the method of Example 2-1 (IQ23), except that 4-methoxyphenylboronic acid was used instead of 4-formylphenylboronic acid.

Yellow solid, ¹H NMR (300 MHz, CDCl₃) δ 8.37 (d, J=8.1 Hz, 1H), 8.25 (d, J=7.8 Hz, 1H), 7.95 (d, J=7.8 Hz, 1H), 7.76 (d, J=0.9 Hz, 1H), 7.69 (td, J=7.2, 1.5 Hz, 1H), 7.65-7.62 (m, 3H), 7.59 (d, J=9.0 Hz, 2H), 7.28 (s, 1H), 7.15 (d, J=8.7 Hz, 2H), 6.99 (d, J=9.0 Hz, 2H), 6.72 (dd, J=7.5, 1.2 Hz, 1H), 3.95 (s, 3H), 3.86 (s, 3H); ESI-MS m/z 431 (M+H)⁺.

2-90. Synthesis of methyl 4-(6-(4-methoxyphenyl)indolizino[3,2-c]quinolin-10-yl)benzoate (IQ-B21)

A desired compound (17 mg, 80%) was obtained by the method of Example 2-1 (IQ23), except that 4-(methoxycarbonyl)phenylboronic acid was used instead of 4-formylphenylboronic acid.

Yellow solid, ¹H NMR (300 MHz, CDCl₃) δ 8.39 (dd, J=7.8, 1.8 Hz, 1H), 8.26 (d, J=8.1 Hz, 1H), 8.13 (d, J=8.4 Hz, 2H), 8.00 (d, J=7.8 Hz, 1H), 7.90 (s 1H), 7.40 (d, J=8.4 Hz, 2H), 7.68-7.60 (m, 5H), 7.37 (s, 1H), 7.15 (d, J=8.4 Hz, 2H), 6.76 (dd, J=7.8, 2.1 Hz, 1H), 3.95 (s, 3H); ESI-MS m/z 459 (M+H)⁺.

Example 3: Selection of Candidate Compound for Fluorescent Probe

To be used as a biological fluorophore, a compound should have a high emission intensity in water, low self-quenching, and a large Stokes shift to minimize homotransfer of energy. In addition, for the development of medicinal chemistry and fluorophores, the compound should have excellent solubility to minimize aggregation with a protein, which is a more essential condition to be used as a protein labeling dye.

To screen a compound having such conditions as a fluorophore, the maximum absorption wavelength ($\lambda_{max\ ex}$), the peak emission wavelength ($\lambda_{max\ em}$), and the relative fluorescence intensity (Emission Intensity$_{norm}$) were measured for the compounds of Formula 1, and the results are shown in Tables 2 and 3.

TABLE 2

| Entry # | Maximum absorption wavelength $\lambda_{max\ abs}$(nm) | Peak emission wavelength $\lambda_{max\ em}$(nm)$^a$ | Fluorescence Emission Intensity$^b$ | Relative fluorescence Emission Intensity$_{norm}$$^c$ |
|---|---|---|---|---|
| 1 | 400 | 522 | 32.7 | 0.14 |
| 2 | 371, 402 | — | — | 0.00 |
| 3 | 380, 400 | 519 | 59.7 | 0.26 |
| 4 | 380, 400 | 519 | 55.0 | 0.24 |
| 5 | 400 | 532 | 4.7 | 0.02 |
| 6 | 430 | 514.5 | 231.3 | 0.99 |
| 7 | 399, 421 | 527.5 | 60.8 | 0.26 |
| 8 | 399, 421 | 513 | 171.3 | 0.74 |
| 9 | 399, 421 | 514 | 232.9 | 1.00 |
| 10 | 399, 421 | 532 | 39.6 | 0.17 |
| 11 | 407 | 536 | 7.5 | 0.03 |
| 12 | 395 | 531.5 | 11.8 | 0.05 |
| 13 | 375, 395 | — | — | 0.00 |
| 14 | 375, 395 | 527.5 | 25.5 | 0.11 |
| 15 | 375, 395 | 535.5 | 9.4 | 0.04 |
| 16 | 373, 391 | 535 | 11.7 | 0.05 |
| 17 | 391 | 524.5 | 31.7 | 0.14 |
| 18 | 400 | 523.5 | 15.0 | 0.06 |
| 19 | 362, 383 | 478 | 80.5 | 0.35 |
| 20 | 362, 380 | 493 | 143.5 | 0.62 |
| 21 | 362, 383 | 432.5 | 226.5 | 0.97 |
| 22 | 386, 406, 430 | 512 | 89.5 | 0.38 |
| 23 | 386, 406, 430 | 518 | 82.4 | 0.35 |
| 24 | 386, 406, 430 | 513 | 75.1 | 0.32 |
| 25 | 391, 411 | 505.5 | 13.4 | 0.06 |
| 26 | 384 | — | — | 0.00 |
| 27 | 362, 383 | 474 | 98.9 | 0.42 |
| 28 | 362, 383 | 476 | 211.7 | 0.91 |

TABLE 2-continued

| Entry # | Maximum absorption wavelength $\lambda_{max\ abs}$(nm) | Peak emission wavelength $\lambda_{max\ em}$(nm)[a] | Fluorescence Emission Intensity[b] | Relative fluorescence Emission Intensity$_{norm}$[c] |
|---|---|---|---|---|
| 29 | 362, 383 | 482 | 186.2 | 0.80 |
| 30 | 362, 383 | 480.5 | 210.7 | 0.90 |
| 31 | 362, 383 | 515 | 106.5 | 0.46 |

[a]Excited at the longest absorption maxima;
[b]Fluorescence spectra recorded in H$_2$O at 2 μM;
[c]Normalized fluorescence intensity.

As confirmed in Table 2, the compounds of the present invention generally show the maximum absorption in a range of approximately 380 to 430 nm, which means that excitation of visible light is possible. In addition, in a state of an aqueous solution, the peak emission wavelength is shown in a range of approximately 480 to 540 nm.

Further the most striking characteristic is that a large Stokes shift (90-110 nm) is observed in most of the compounds, which means that there is apparent separation between the excitation wavelength and the emission wavelength. That is, the emission spectrum was observed in a range similar to Alexa Fluor 488 or Fluorescein, but the excitation wavelength was quite large different from the emission wavelength.

Such a result shows that the compounds of Formula 1 according to the present invention are suitable to be used as a fluorophore, and applicable particularly in cell imaging using a multi-fluorescence technique.

Example 4: Analysis of Optical Characteristics 4-1. Substituent-Dependent Characteristic Among the compounds listed in Table 2, prepared in Example 3, Compounds IQ 6, 9, 21, 28 and 30 which have the highest emission intensities were selected. These compounds are represented by Formulas 2, 3, 4, 5 and 6, shown in FIG. 1, respectively, and absorption and emission spectra measured in an aqueous solution for these compounds are shown in FIG. 2.

As a result, as confirmed in FIGS. 1 and 2, the compound (IQ 6) of Formula 2 has the structure in which a p-methoxyphenyl group is bound at an R$_6$ position, and shows high fluorescence with the peak emission at 514 nm. This is because an electron-donor methoxy group is present at the position opposite to the nitrogen of the quinoline deficient in electrons, and the methoxy group at the para position is considered to play a pivotal role in increasing fluorescence intensity. That is, a significant change in dipole moment is expected to occur at the time of excitation of a molecule.

Generally, such an electronic effect corresponded to the result of a different compound, and for example, the compounds (IQ 2, 13 and 26) in which a bromine or nitrogen group, not a methoxy group, is bound at the para position of the aromatic ring did not induce fluorescence. That is, depending on a substituent at the R position of a phenyl group, a fluorescence quantum yield (QY) was changed due to the electronic effect, and such an interaction is shown in FIG. 3.

In addition, in the compound (IQ 9) of Formula 3, strong fluorescence is caused by the naphthalene substituent at the R$_6$ position.

Stokes shifts and fluorescence quantum yields (Φ) were measured for the compounds with the high fluorescence intensity, that is, the compounds of Formulas 2 to 6 (IQ 6, 9, 21, 28 and 30), and the results are shown in Table 3.

TABLE 3

| Entry # | Absorption coefficient (cm$^{-1}$M$^{-1}$) | Absorption wavelength $\lambda_{ex}$(nm) | Emission wavelength $\lambda_{em}$(nm) | Stokes shift (cm$^{-1}$) | Fluorescence quantum yield (Φ)[a] |
|---|---|---|---|---|---|
| 6 | 6547 | 430 | 515 | 38383 | 0.121 |
| 9 | 11656 | 405 | 515 | 52739 | 0.053 |
| 21 | 9012 | 383 | 433 | 30150 | 0.033 |
| 28 | 10780 | 369 | 476 | 60919 | 0.061 |
| 30 | 10580 | 369 | 481 | 63103 | 0.084 |

[a]Quantum yields were measured using Rhodamine 6G as a standard (Φ = 0.86 in water); and the excitation/emission wavelengths of Rhodamine 6G were in the ranges of 425-575/505-750 nm, respectively.

4-2. Solvent-Dependent Characteristic

As applicable candidate fluorescent probes, the five types of indolizino[3,2-c]quinoline compounds (IQ 6, 9, 21, 28 and 30) with a high fluorescence intensity were subjected to spectrum analyses in various solvents, and the results are shown in Table 4 and FIG. 4.

TABLE 4

| Entry # | H$_2$O $\lambda_{em}$ (nm) | DMSO $\lambda_{em}$ (nm) | DMF $\lambda_{em}$ (nm) | EtOH $\lambda_{em}$ (nm) | EtOH:CHCl$_3$ = 1:5 $\lambda_{em}$ (nm) | MC $\lambda_{em}$ (nm) |
|---|---|---|---|---|---|---|
| 6 | 511 | 512 | 469 | 465 | 466 | 467 |
| 9 | 516 | 514 | 478 | 465.5 | 467.5 | 469 |
| 21 | 431 | 453 | 453 | 447.5 | 453.5 | 453.5 |
| 28 | 476 | 472.5 | 470 | 449.5 | 450 | 451.5 |
| 30 | 478.5 | 452.5 | 450 | 444 | 447.5 | 448 |

As shown in Table 4 and FIG. 4, it was seen that the emission spectra of these materials can vary according to the polarity of a solvent. The compounds (IQ 6, 9, 28 and 30) of Formulas 2, 3, 5 and 6 below exhibited a solvatochromic effect by inducing bathochromic shifts towards a longer wavelength of the peak emission in an aqueous solution.

Particularly, the compounds (IQ 6 and 9) of Formulas 2 and 3 had the peak emissions in an ethanol solvent (EtOH) at $\lambda_{max}$=511 nm and 516 nm, respectively, and in an aqueous solvent (H₂O) at $\lambda_{max}$=465 nm and 465.5 nm, respectively, and showed considerable red-shifts in an aqueous solvent, compared to ethanol. The quantum yields of the compounds of Formulas 2 and 3 were measured in ethanol using coumarin 153 as a standard, and considerably increased to 0.816 and 0.402, respectively. That is, these compounds are expected to have a great change in dipolar moment during excitation.

On the other hand, the compound (IQ 21) of Formula 4 had the peak emission of a blue-shift in an aqueous solvent (H₂O) at $\lambda_{max}$=433 nm, and therefore showed an opposite tendency of the compounds of Formulas 2 and 3.

[FORMULA 2]

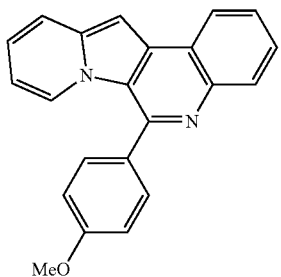

[FORMULA 3]

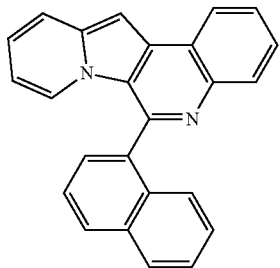

[FORMULA 4]

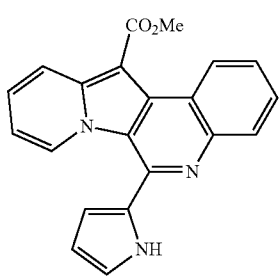

[FORMULA 5]

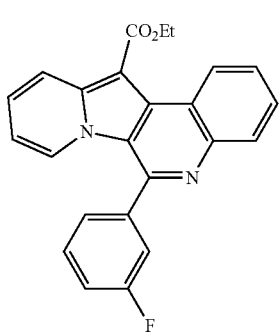

[FORMULA 6]

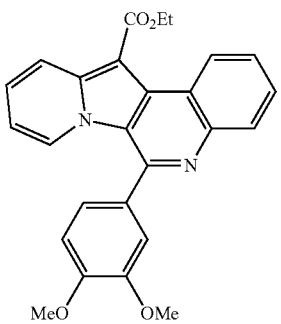

Therefore, to compare the quantum yields between an aqueous solvent and ethanol, the compounds of Formula 1 synthesized in Example 2 according to the present invention were subjected to spectrum analysis in an aqueous solvent or ethanol solvent, and the results are shown in Table 5, and FIGS. 5A, 5B and 5C.

TABLE 5

| Entry # | DW $(\Phi)^a$ | EtOH $(\Phi)^b$ |
|---|---|---|
| 1 | 0.015 | 0.636 |
| 2 | 0.000 | 0.000 |
| 3 | 0.068 | 0.839 |
| 4 | 0.039 | 0.779 |
| 5 | 0.005 | 0.196 |
| 7 | 0.026 | 0.756 |
| 8 | 0.102 | 0.652 |
| 10 | 0.015 | 0.350 |
| 11 | 0.006 | 0.111 |
| 12 | 0.131 | 0.623 |
| 13 | 0.000 | 0.000 |
| 14 | 0.025 | 0.706 |
| 15 | 0.024 | 0.654 |
| 16 | 0.014 | 0.672 |
| 17 | 0.065 | 0.604 |
| 18 | 0.008 | 0.421 |
| 19 | 0.060 | 0.222 |
| 20 | 0.367 | 0.468 |
| 22 | 0.070 | 0.440 |
| 23 | 0.065 | 0.106 |
| 24 | 0.030 | 0.063 |
| 25 | 0.009 | 0.031 |
| 26 | 0.000 | 0.000 |
| 27 | 0.073 | 0.318 |
| 29 | 0.120 | 0.365 |
| 31 | 0.070 | 0.194 |
| 33 | 0.082 | 0.277 |
| 35 | 0.073 | 0.365 |
| 36 | 0.006 | 0.386 |
| 37 | 0.001 | 0.324 |
| 39 | 0.026 | 0.492 |
| 40 | 0.142 | 0.624 |
| 42 | 0.010 | 0.201 |
| 43 | 0.014 | 0.275 |
| 44 | 0.010 | 0.050 |
| 45 | 0.033 | 0.557 |
| 46 | 0.039 | 0.604 |
| 47 | 0.050 | 0.597 |
| 48 | 0.105 | 0.050 |
| 49 | 0.085 | 0.195 |
| 50 | 0.014 | 0.037 |

[a]Rhodamine 6G ($\Phi$ = 0.816 in water);
[b]Coumarin 153 ($\Phi$ = 0.053 in EtOH).

As shown in Table 5, and FIGS. 5A, 5B and 5C, it can be seen that the fluorescence yield in ethanol, compared to an aqueous solution, was highly increased (Table 5), and there were 15 types of compounds with a fluorescence yield of 0.8 or more among the total of 41 types of compounds (FIG.

5A). In addition, when the indolizino[3,2-c]compound of the present invention is represented by Formula X below, and an E ring was fixed as the same structure, and an A or B ring was substituted with a hydrogen (proton) or methyl (methyl) group depending on the quantum yield tendency in ethanol according to the substituted group, the quantum yields were similar, but when a bromo group or an ester group was substituted, it can be seen that the quantum yield was decreased (FIG. 5B).

[Formula X]

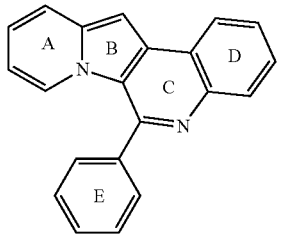

Further, the compounds (excluding Entry #51-57, etc.) of Formula 1 were subjected to spectrum analyses in various solvents, and the results are shown in Tables 6 and 7, and FIGS. 5C and 5D.

TABLE 6

| Entry # | $\lambda_{ex}$(nm) | $\lambda_{em}$(nm) | | | |
|---|---|---|---|---|---|
| | | DW | EtOH | MC | DMF |
| 51 | 403 | 484.5 | 443.5 | 437 | 448.5 |
| 52 | 399 | 534.5 | 489 | 437 | 507.5 |
| 53 | 422 | 527 | 504.5 | 487.5 | 505.5 |
| 55 | 413 | 511 | 484 | 486 | 488.5 |
| 56 | 422 | 511 | 464.5 | 470.5 | 469.5 |
| | 450 | 512.5 | 483.5 | 498 | 518.5 |
| 57 | 401 | 479 | 433.5 | 437 | 448 |
| 5-D | 402 | 543 | 534 | 436 | 537 |
| | 422 | 493 | 532.5 | 519 | 534 |
| 6-T | 403 | 525 | 487 | 437 | 498.5 |
| 6-T-B | 437 | 530.5 | 500 | 525 | 501.5 |
| 6-S1-Me | 458 | 500 | 500 | 493 | 507.5 |
| 6-S2-Cl | 464 | 503.5 | 503.5 | 498.5 | 507.5 |

TABLE 7

| Entry # | $\lambda_{ex}$(nm) | $\lambda_{em}$ (nm) | | | | Fluorescence (DW) Emission Intensity | Relative fluorescence (DW) Emission Intensity$_{norm}$ |
|---|---|---|---|---|---|---|---|
| | | DW | Tris (20 mM, pH 7.5) | EtOH | DMSO | | |
| 67 | 403 | 501 | 498.5 | 495 | 502 | 221.3 | 0.36 |
| | 423 | 502.5 | 499.5 | 495 | 502 | 370.7 | 0.61 |
| | 447 | 501.5 | 499.5 | 495 | 501.5 | 560 | 0.92 |
| 72 | 429 | — | — | — | — | — | 0.00 |
| | 470 | — | — | — | — | — | 0.00 |
| 76 | 377 | 511.5 | 488 | 468.5 | 473 | 2.8 | 0.00 |
| | 398 | 513.5 | 494 | 464.5 | 475 | 6.7 | 0.01 |
| | 418 | 511 | 503 | 467.5 | 474 | 12 | 0.02 |
| 77 | 374 | 505 | 483 | 434 | 441.5 | 126.6 | 0.21 |
| | 393 | 505.5 | 485 | 433 | 442 | 161.5 | 0.27 |
| 79 | 366 | 473 | 471 | 423.5 | 423 | 232.2 | 0.38 |
| | 386 | 473.5 | 471.5 | 423.5 | 423 | 579.3 | 0.95 |
| B1 | 399 | 508.5 | 480 | 459.5 | 469 | 18.2 | 0.03 |
| | 421 | 508 | 482.5 | 459.5 | 469.5 | 27.4 | 0.05 |
| B2 | 379 | 510 | 486 | 460.5 | 469.5 | 62.8 | 0.10 |
| | 399 | 511.5 | 498 | 460 | 471 | 141.6 | 0.23 |
| | 421 | 509.5 | 503 | 461 | 470 | 273.1 | 0.45 |
| B4 | 415 | 488 | 481 | 529.5 | 539 | 2.1 | 0.00 |
| B11 | 427 | 519 | 531 | 515 | 513.5 | 175.9 | 0.29 |
| B12 | 344 | — | — | 524.5 | 534.5 | — | 0.00 |
| | 407 | — | — | 522 | 532.5 | — | 0.00 |
| B16 | 422 | — | — | 521 | 530 | — | 0.00 |
| B19 | 409 | 517.5 | 512.5 | 501.5 | 509.5 | 126.8 | 0.21 |
| | 431 | 517 | 517 | 501.5 | 510 | 303.2 | 0.50 |
| | 457 | 518 | 518.5 | 501.5 | 510 | 608 | 1.00 |
| B20 | 400 | 514 | 498.5 | 489 | 494.5 | 113.2 | 0.19 |
| | 422 | 514.5 | 501.5 | 489 | 495 | 284.4 | 0.47 |
| | 446 | 514.5 | 506.5 | 489.5 | 495 | 578.9 | 0.95 |
| B23 | 434 | 518.5 | 547.5 | 527.5 | 541 | 50.8 | 0.08 |
| B25 | 444 | 533 | 524.5 | 547 | 540.5 | 135.3 | 0.22 |
| B31 | 440 | 546.5 | 564.5 | 522 | 534.5 | 7.1 | 0.01 |
| B35 | 427 | 515 | 539 | 511 | 520 | 82.6 | 0.14 |
| B36 | 422 | 512.5 | 510 | 503 | 509 | 377.2 | 0.62 |
| B37 | 432 | 512.5 | 545.5 | 503 | 513 | 26.7 | 0.04 |
| B39 | 423 | 516.5 | 529.5 | 495.5 | 503 | 47.8 | 0.08 |
| B43 | 431 | 513 | 532.5 | 518.5 | 526.5 | 400.7 | 0.66 |
| B44 | 436 | 516.5 | 524 | 517.5 | 527 | 440.9 | 0.73 |
| B46 | 382 | 527.5 | 503.5 | 482 | 510 | 4.2 | 0.01 |
| | 400 | 530.5 | 505.5 | 482 | 510.5 | 8.9 | 0.01 |

As shown in Table 6, and FIGS. 5C and 5D, depending on a substituent of the compound, a degree of a solvent-dependent (i.e., environment-sensitive) tendency was different, and particularly, the compound (IQ-B1) of Formula 25 below and the compound (IQ-B2) of Formula 26 below, which have an —OH or —NH₂ substituent at an aryl group, showed a high solvent-dependent (i.e., environment-sensitive) tendency. In addition, the compound (IQ 67) of Formula 22 below showed further high fluorescence intensity in an aqueous solution, and the compound (IQ 77) of Formula 23 and the compound (IQ 79) of Formula 24 showed very high fluorescence intensity at a blue wavelength in EtOH and DMSO. The compound (IQ-B19) of Formula 27 and the compound (IQ-B20) of Formula 28 showed high fluorescence in other solvents as well as an aqueous solution. It was confirmed that the compound (IQ-B23) of Formula 29 and the compound (IQ-B25) of Formula 30 showed high fluorescence in DMSO, the compound (IQ 55) of Formula 16 below having acetylene and the compounds (IQ 6-S1-Me and 6-S2-Cl) of Formulas 20 and 21 having a quaternary ammonium salt hardly showed an environment-sensitive optical characteristic of changing the maximum fluorescence wavelength value according to the polarity of a solvent. In addition, it was confirmed that, in the case of compound (IQ 5-D) of Formula 19 below, the maximum fluorescence wavelength shifted towards a longer wavelength up to 543 nm in an aqueous solution. It was confirmed that, in the case of compound (IQ-B11) of Formula 31 below, the maximum wavelength shifted towards a longer wavelength up to 531 nm in a Tris buffer (pH 7.5).

In addition, as shown in FIG. 6, it was confirmed that, the compound (IQ-B12) of Formula 32 below exhibited the Abs maximum λ for UV at 344 nm, em λ for fluorescence at 520 to 530 nm, and a Stokes shift of 180 nm or more.

[FORMULA 16]

[FORMULA 19]

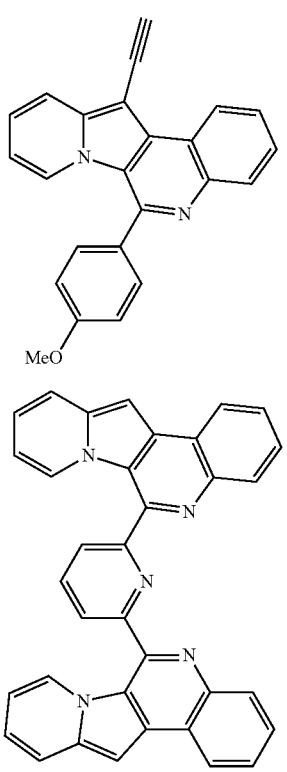

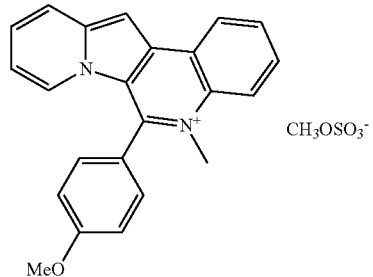

[FORMULA 20]

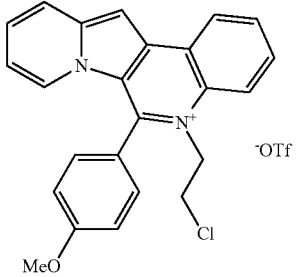

[FORMULA 21]

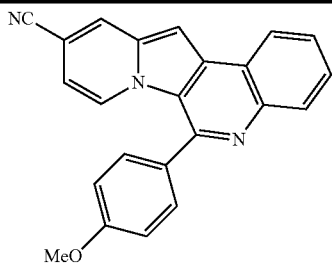

[Formula 22]

IQ67

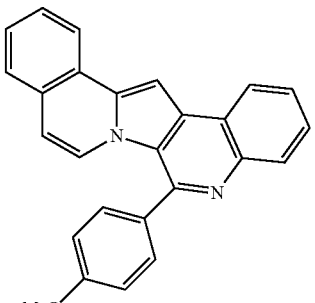

[Formula 23]

IQ77

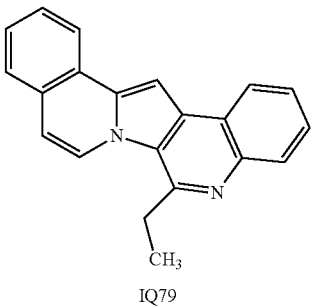

[Formula 24]

IQ79

[Formula 25]

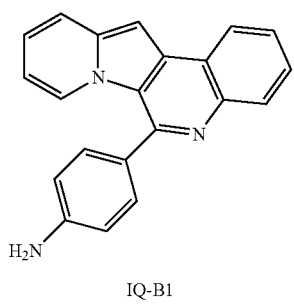 [SMILES: Nc1ccc(-c2nc3ccccc3c3cc4ccccn4c23)cc1]

IQ-B1

[Formula 26]

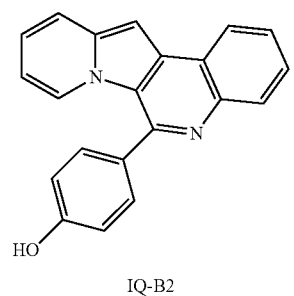 [SMILES: Oc1ccc(-c2nc3ccccc3c3cc4ccccn4c23)cc1]

IQ-B2

[Formula 27]

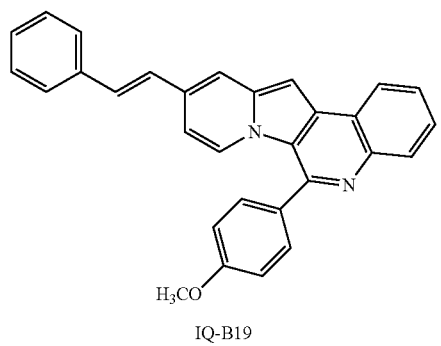 [SMILES: COc1ccc(-c2nc3ccccc3c3cc4cc(/C=C/c5ccccc5)ccn4c23)cc1]

IQ-B19

[Formula 28]

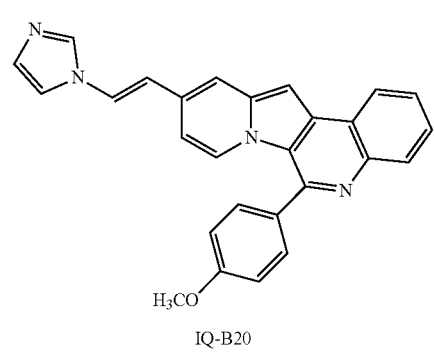 [SMILES: COc1ccc(-c2nc3ccccc3c3cc4cc(/C=C/n5ccnc5)ccn4c23)cc1]

IQ-B20

[Formula 29]

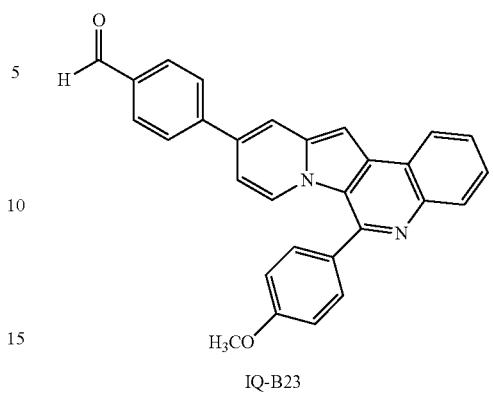

IQ-B23

[Formula 30]

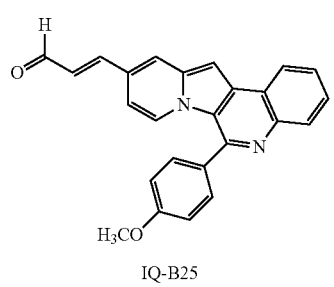 [SMILES: COc1ccc(-c2nc3ccccc3c3cc4cc(/C=C/C=O)ccn4c23)cc1]

IQ-B25

[Formula 31]

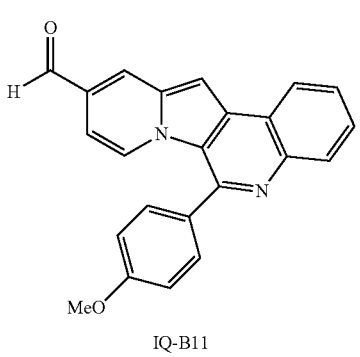 [SMILES: COc1ccc(-c2nc3ccccc3c3cc4cc(C=O)ccn4c23)cc1]

IQ-B11

[Formula 32]

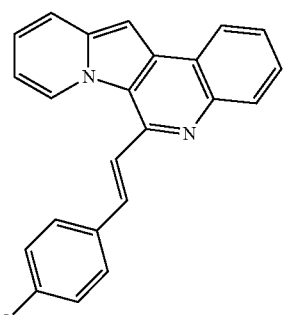

IQ-B12

Therefore, such a solvent-dependent optical characteristic of the indolizino[3,2-c]quinoline compound may be controlled by changing a substituent. In addition, it is demonstrated that the environment-sensitive characteristic of the indolizino[3,2-c]quinoline compound is able to be used as a fluorescent probe suitable for monitoring a biological process such as drug-target binding or protein dynamics.

4-3. Optical Stability in Aqueous Solution

As a candidate material that can be applied to a fluorescent probe, to confirm how long fluorescence persists in materials with high fluorescence intensity in an aqueous solution among the indolizino[3,2-c]quinoline compounds, photostability according to time in an aqueous solution or ethanol solvent was evaluated as follows.

First, fluorescence of a corresponding material was measured using a cuvette, and the fluorescence per time for the cuvette sample was remeasured until 6 to 7 hours in a natural light state so as to confirm fluorescence stability.

As a result, in the case of an aqueous solution, as shown in FIG. 7A, the fluorescence of the IQ 3, 4, 6 and 8 compounds were stably maintained in an aqueous solution up to 6 hours with almost no change, in an ethanol solvent, as shown in FIG. 7B, most of the indolizino[3,2-c]quinoline compounds exhibited high fluorescence intensity, and thus more materials can be screened, and in an aqueous solution, even materials having an electron withdrawing group (EWG) in which fluorescence is not maintained showed stably maintained fluorescence, and their fluorescence intensity was also maintained for 6 hours with almost no change.

Further, from the above example, when the indolizino[3,2-c]quinoline compounds including the IQ 3, 4, 6 and 8 compounds in which the fluorescence is stably maintained in an aqueous solution for approximately 6 hours are represented by Formula X, some materials in which neither A, B, C nor D ring has a substituent were selected and irradiated with blue light in an aqueous solution, and then a stability experiment was carried out to confirm the maintenance of the fluorescence.

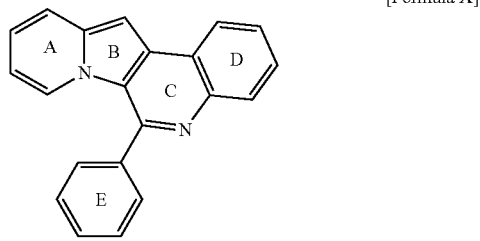

[Formula X]

As a result, as shown in FIG. 7C, it can be seen that IQ 3, 4, 5 and 6 materials still stably exhibited fluorescence intensity even under the condition of irradiation with blue light for 2 hours, and thus showed excellent stability of fluorescence.

Example 5: Analysis of Binding Characteristic to DNA

Using a fluorescence spectrophotometer, it was confirmed whether the indolizino[3,2-c]quinoline compound of the present invention binds to DNA. First, DNA oligomers (48 bp) used in the experiment are tetO sequences, and the base sequences thereof are as follows.

tetO1:
5'-CCTAATTTTTGTTGACACTCTATCATTGATAGAGTTATTTTACCACT
C-3' tetO2:
5'-GAGTGGTAAAATAACTCTATCAATGATAGAGTGTCAACAAAAATTAG
G-3'

The same molarities of oligomers were mixed while being heated at 95° C. for 5 minutes and cooled to room temperature for 2 hours to hybridize, the fluorescence of each of the indolizino[3,2-c]quinoline compounds of the present invention was measured, a corresponding equivalent of DNA oligomer was added to a cuvette, and then incubated while blocking light for 1 minute to measure fluorescence again.

As a result, as shown in Table 8 and FIG. 8, when such DNA oligomers were added, it was confirmed that there were the group (8A) of compounds in the peak emission wavelength shifts to a shorter wavelength as the fluorescence intensity changes, the group (8B) of compounds in which the peak emission wavelength shifts to a longer wavelength as the fluorescence intensity changes, the group of compounds in which only fluorescence intensity is changed and the group (8C) of compounds which are not changed at all.

TABLE 8

|  | Compound (IQ) |
| --- | --- |
| Change in fluorescence intensity & shift of maximum emission wavelength to longer wavelength | 6, 8, 14, 17, 36, 37 |
| Change in fluorescence intensity & shift of maximum emission wavelength to shorter wavelength | 18. 19. 42. 44 |
| Decrease in fluorescence intensity | 3, 4 |
| Increase in fluorescence intensity | 10, 40 |
| No change in fluorescence intensity | 45, 46 |

Particularly, it was confirmed that, as the compound (IQ 15) of Formula 7 below binds to DNA, the fluorescence was gradually decreased and the shift of the wavelength to a longer wavelength was exhibited, and as the compound (IQ 18) of Formula 8 including furan binds to DNA, the fluorescence was gradually decreased and the shift of the wavelength to a shorter wavelength (8D) was exhibited.

[FORMULA 7]

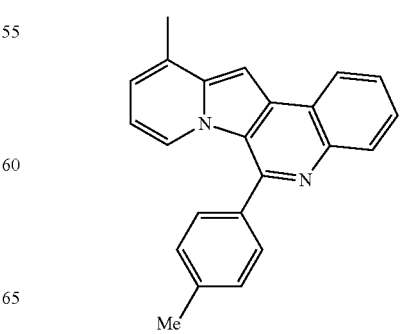

[FORMULA 8]

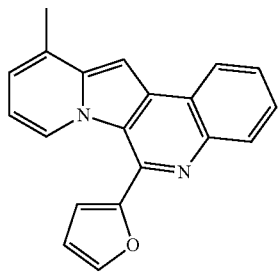

Example 6: Analysis of Protein Binding Characteristic

Using a fluorescence spectrophotometer, it was confirmed whether the indolizino[3,2-c]quinoline compound of the present invention binds to a protein. Specifically, among the indolizino[3,2-c]quinoline compounds, 13 types of compounds with high fluorescence in a Tris buffer (pH 7.5) were added to Bovine Serum Albumin (BSA) and Human Serum Albumin (HSA) to observe a fluorescence change.

As a result, as shown in FIG. 9, it can be seen that the compound (IQ 7) of Formula 9 below showed emission at approximately 500 nm when the compound was excited at 280 nm, while HSA showed emission at 340 nm when excited at 280 nm, HSA showed a decrease in emission intensity at 340 nm, and also emission at approximately 450 nm by adding 1 equiv. of the compound to HSA, and therefore as HSA bound to the material, a fluorescence resonance energy transfer (FRET) phenomenon occurred (the upper panel of FIG. 9), and also seen that when excitation was performed at wavelengths of 399 nm and 421 nm and 1 equiv. of HSA was added, due to binding to HSA, fluorescence intensity became higher than the fluorescence of the material, the wavelength shifted towards a shorter wavelength, and a peak shape was also changed (the lower panel of FIG. 9).

[FORMULA 9]

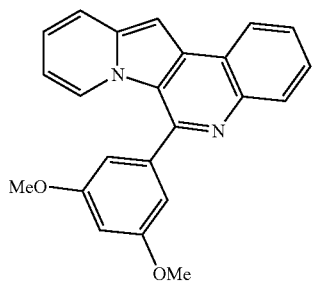

In addition, as shown in FIG. 10, it can be visually confirmed that the compound (IQ 7) of Formula 9 was further increased in fluorescence intensity in the compound+HSA group (3$^{rd}$ vial), that is, upon binding to HSA, rather than the compound only, compared to the compound only group (1$^{st}$ vial) or the HSA only group (2$^{nd}$ vial). Further, by measuring a quantum yield (QY), when the compound was bound to HSA, rather than the compound only, the QY was increased to 0.43 (the upper panel of FIG. 10), and it was confirmed according to a Job's Plot that the compound of Formula 9 bound to HSA at 1:1, and as a result of titration, it can be confirmed that the $K_D$ value was 1.89 μM (the lower panel of FIG. 10).

Therefore, based on the above results, the increase in fluorescence intensity due to binding of the indolizino[3,2-c]quinoline compound to HSA was visualized using a plate well, which is shown in FIG. 10, and a method of screening a compound binding to HSA by a high throughput method was constructed.

Further, it was confirmed that 9 types of the indolizino [3,2-c]quinoline compound (IQ 3, 4, 7, 8, 9, 10, 16, 17 and 40) form complexes with HSA, thereby increasing fluorescence intensity, and as a result of measuring the quantum yields (QY) of fluorescent proteins using coumarin 153 (Φ=0.12 in water) as a reference material, as shown in FIG. 12, it was confirmed that, when binding to HSA, the compound (IQ 17) of Formula 10 below had a higher QY, that is, 0.4, than that of the compound only.

[FORMULA 10]

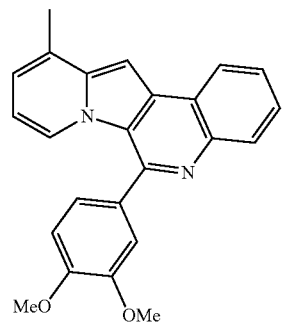

6-1. Confirmation of Target Protein (PDE-δ) using FRET 20 to 30% mutated K-Ras proteins were found in human cancer cells, and have been known to cause cancer. Therefore, a variety of studies on K-Ras proteins as anticancer target proteins have been progressing for the past several decades, the affinity between the K-Ras protein and GTP is at a picomolar level, which indicates strong binding, and since there is no allosteric site known in the protein, a therapeutic agent for directly inhibiting the K-Ras protein has not been developed. Recently, in the research on an intercellular position of the K-Ras protein and a cancer-causing mechanism, research on a target protein PDEδ, which can interrupt cell proliferation-related signaling of the K-Ras protein, has been conducted, but an inhibitor for PDEδ, other than deltarasin, has not been reported yet.

When irradiated with 280-nm light, the PDE protein exhibited the peak emission wavelength at 340 nm due to a tryptophan residue, and when binding to a ligand, the peak emission wavelength at 340 nm was reduced in intensity, or changed due to the FRET phenomenon.

Therefore, to confirm whether the fluorescent material is able to selectively bind to a specific protein in a cell, fluorescence of the recombinant PDE and/or indolizino[3, 2-c]quinoline compound, which is overexpressed in *E. coli* cells, followed by isolation and purification, was measured by being irradiated with 280-nm light.

As a result, as shown in FIG. 13, in buffer, the PDE protein (red dotted line) showed the peak emission wavelength at 340 nm, and the indolizino[3,2-c]quinoline compound (blue dotted line) showed the peak emission wavelength at approximately 500 nm. In addition, when the PDE was mixed with the indolizino[3,2-c]quinoline compound, and then fluorescence was measured (green line), it was confirmed that the peak emission wavelength at 340 nm of the PDE protein was decreased, the peak emission wavelength of the indolizino[3,2-c]quinoline compound shifted towards 475 nm, and the fluorescence intensity itself was also increased.

Through observation of the FRET phenomenon, it was first confirmed that the indolizino[3,2-c]quinoline compound binds to PDEδ, and experiments of confirming binding of PDEδ to compounds, other than the compounds having low fluorescence intensity such as the IQ 2 compound and no change in fluorescence such as the IQ 13 compound, were further performed.

6-2. Titration using Fluorescence Polarization

To confirm whether the indolizino[3,2-c]quinoline compound can bind to a specific intracellular protein, in the presence of 0.5 μM of the indolizino[3,2-c]quinoline compound, titration was performed by increasing the concentration of the PDEδ protein from 0 to 32 μM to measure a polarization degree.

As a result, as shown in Table 9 below and FIG. 14, it can be shown that the polarization degree was PDEδ concentration-dependently increased, and plotted in a hyperbolic shape. Accordingly, compounds having a high affinity at a level of 300 to 500 nM were identified by screening the indolizino[3,2-c]quinoline compounds, and to perform additional experiments, among these compounds, 8 types of compounds (IQ 1, 3, 4, 6, 8, 9, 10 and 42) were selected.

TABLE 9

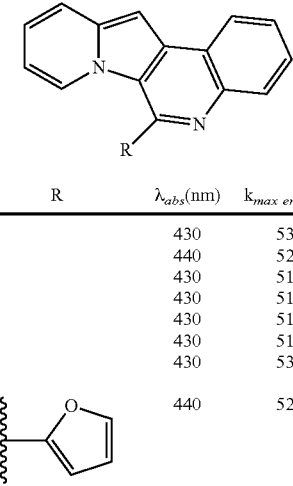

| Entry # | R | $\lambda_{abs}$(nm) | $k_{max\ em}$(nm) | $K_d$(μM) |
|---|---|---|---|---|
| 1 | | 430 | 530 | 0.284 |
| 3 | | 440 | 526 | 0.491 |
| 4 | | 430 | 515 | 0.505 |
| 6 | | 430 | 515 | 0.729 |
| 8 | | 430 | 515 | 1.285 |
| 9 | | 430 | 515 | 1.541 |
| 10 | | 430 | 530 | 0.643 |
| 42 | (furan) | 440 | 526 | 0.425 |

6-3. Confirmation of Binding of PDE-δ Protein using Competitive Binding

A complex of the indolizino[3,2-c]quinoline compound and the PDEδ protein was formed, when an excessive amount of non-fluorescent deltarasin was added, and the deltarasin and the IQ compound shared the same binding site, the IQ compound became a free form due to the excessive deltarasin, resulting in depolarization, and competitive binding experiments for the 8 types of compounds (IQ 1, 3, 4, 6, 8, 9, 10 and 42) deduced by fluorescence polarization screening used in Example 6-2 with respect to the deltarasin, known as a PDEδ inhibitor, were carried out.

As a result, as shown in FIG. 15, it was confirmed that a polarization level according to time, caused by the complex of the indolizino[3,2-c]quinoline compound and the PDEδ protein was not changed, but when the deltarasin was excessively added, the polarization degree was reduced, and therefore it can be seen that the deltarasin and the IQ compound bind to the same binding site. In addition, according to the graph showing that the polarization degree is decreased over time, the half-life of the compound to be detected may be measured in the presence of excessive amounts of competitive compounds, and therefore, it can be confirmed that the compound having a high affinity (Kd) has a longer half-life.

Therefore, in the present invention, the indolizino[3,2-c]quinoline compounds deduced by fluorescence screening had high affinity (Kd value) of 300 to 500 nM and exhibited fluorescence, and in research on the PDEδ inhibitor, they are expected to be used as probe compounds, and in terms of economic feasibility and efficiency, also expected to be used as an alternative to a detection method using an antibody.

Example 7: Actual Application of Characteristics as Fluorescent Protein

7-1. Confirmation of Target Specificity

To confirm binding between the IQ compound and the PDEδ protein, an experiment was carried out by adding the compound (IQ 3) of Formula 13 below (1: 0.5 mM, 2: 0.1 mM) to each protein fraction (Sol: Soluble, FT: Flow through, W1: Washing 1, WF: Washing final, M: Marker, E1-5: Elution), and as shown in FIG. 16, the protein was isolated and identified.

[FORMULA 13]

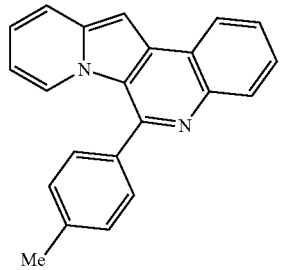

7-2. Confirmation of Interaction between PDES and Compound (IQ 3) of Formula 13

Based on the result of Example 7-1, binding to a protein was confirmed using a native gel. Specifically, (A) the analysis of fluorescence (Ex 312 nm, Em 585-625 nm) of the compound of Formula 13 with respect to a 12% native gel using ImageQuant LAS 4000 and (B) the analysis of fluorescence of the compound of Formula 13 with respect to a native gel through Coomassie blue staining were performed (1: the addition of DMSO to a lysate, 2: the addition of 35 μM of the compound to a lysate, 3: the addition of 350 μM of the compound to a lysate, M: Marker, 4: the addition of DMSO to purified PDEδ, 5: the addition of 35 μM of the compound to purified PDEδ, 6: the addition of 350 μM of the compound to purified PDEδ), and the results are shown in FIG. 17.

Such results demonstrate that a fluorescent protein can be separated and purified without using a separate reagent for detecting the protein, such as a conventional Bradford reagent.

Example 8: Analysis of Cell Permeability

An experiment carried out to confirm whether the indolizino[3,2-c]quinoline compounds of the present invention have excellent cell permeability was as follows.

8-1. Fluorescence Imaging

HeLa cells were seeded in a 96-well plate and incubated for 24 hours. The cells were treated with the indolizino[3,2-c]quinoline compounds, and incubated at 37° C. under a 5% $CO_2$ condition for 30 minutes. After removal of the medium, the cells were washed with 1×DPBS. The washed cells were fixed with 4% formaldehyde at room temperature for 10 minutes, and washed with 1×DPBS. A cell image was screened using an Operetta HTS imaging system (PerkinElmer).

8-2. Live Cell Confocal Imaging

After HeLa cells were seeded to account for 70 to 80% of the area of a confocal dish (SPL life science) and overnight cultured, the indolizino[3,2-c]quinoline compounds (10 μM) prepared by mixing fresh DMEM after removal of the existing DMEM medium were dispensed, and the cells were incubated for 30 minutes to 1 hour at 37° C. Afterward, if needed, LysoTracker (50 nM) was mixed with DMEM to remove the existing medium and then dispensed to the cells, and the cells were incubated for 30 minutes at 37° C. After incubation, without washing, the cells were examined by a confocal laser microscope (Leica TCS SP8 SMD, Leica, Mannheim, Germany). However, when co-stained with a LysoTracker, the cells were washed with DPBS twice before the microscopy. The indolizino[3,2-c]quinoline compounds were identified in the blue channel (ex:405 nm, em:409>nm) and the green channel (ex:488 nm, em:493>nm), and the LysoTracker was identified in the red channel (ex:561 nm, em:566>nm).

8-3. HeLa Cells

As a result, from FIG. 18, it was confirmed that the IQ compounds easily permeate the cell membrane to stain cells, and the permeation took approximately 5 minutes at 10 μM, which seems to be similar to that of DAPI which is commercially available as a DNA marker.

In addition, as shown in FIG. 19, depending on the types of intracellular organelles and molecules in which fluorescence is detected, the IQ compounds may be classified into A) compounds (IQ 7, 8, 16 and 17) stained intensively in the nuclear area, B) compounds (IQ 6 and 36) intensively distributed in cytoplasmic and nucleolus areas, C) a compound (IQ 18) distributed in the mitochondria, and D) compounds (IQ 56 and 57) intensively distributed in the lysosomal area. In addition, it was confirmed that the compounds (IQ 6 and 36) of group B recognized intracellular RNA and exhibited fluorescence, and the compounds (IQ 16 and 17) of group A recognized DNA. Here, compared to DAPI used for nuclear staining, which worked at a blue wavelength, it was confirmed that the compounds of group A worked at a green wavelength, and therefore, it was confirmed that the compounds sensed a specific material or condition in cells, and thus can be used as a sensitive probe turned on by even longer wavelength light.

Particularly, as shown in FIG. 20, it was confirmed that, according to live-cell confocal imaging of Example 8-2, the compounds (IQ 56 and 57) of Formulas 17 and 18 below were co-localized with the commercially available marker LysoTracker at a green wavelength and a blue wavelength, respectively. Therefore, it was confirmed that the fluorescent materials of the present invention may stain only selective intracellular organelles without removal of the fluorescent material, have excellent cell permeability, and recognize a different target according to the structure of the compound.

[FORMULA 17]

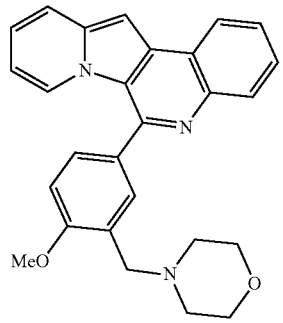

[FORMULA 18]

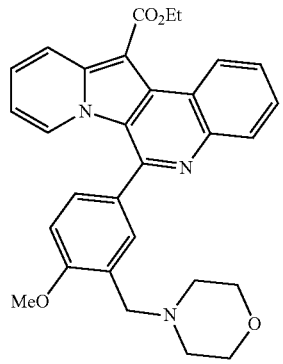

8-4. MCF7 Cells and NIH-3T3 Cells

Through live-cell confocal imaging of Example 8-2, it was confirmed that the same distribution aspect as described above is not only shown in HeLa but also breast cancer-related MCF7 cells (the upper panel of FIG. 21) and NIH3T3 cells, which are normal cells (the lower panel of FIG. 21).

8-5. Sf21 Cells

In addition, as shown in FIG. 22, it was confirmed that, by treating Sf21 cells with the indolizino[3,2-c]quinoline compound, the compounds (IQ 17, 16, and 18) of Formulas 10, 11 and 8 below are permeated into the cells to uniformly stain the entire cells or only the cytoplasm depending on a substituent.

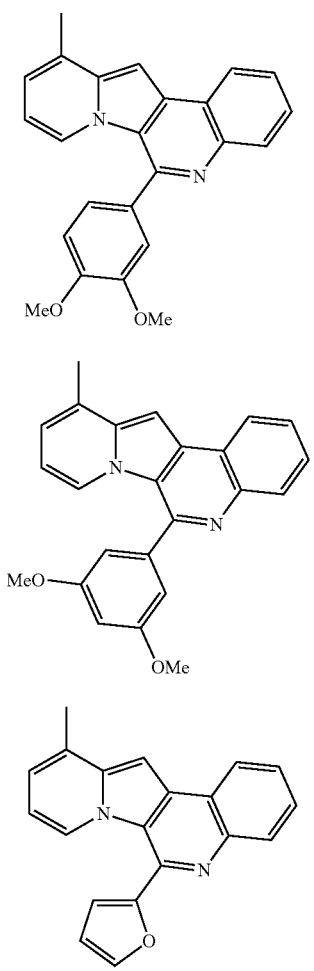

[FORMULA 10]

[FORMULA 11]

[FORMULA 8]

In addition, as a result of confirming whether the indolizino[3,2-c]quinoline compound of the present invention is also detected in live HeLa cells using a yellow wavelength filter (ex 514 nm, em 519 nm) and a red wavelength filter (ex 561 nm, em 566 nm), as shown in FIG. 23, the compound (IQ-B26) of Formula 33, the compound (IQ-B31) of Formula 34 and the compound (IQ-B37) of Formula 35 were detected.

Example 9: Comparison in Cell Permeability with Conventionally Developed Reagents Through co-staining with conventionally used DAPI for staining the nucleus, it was confirmed that the indolizino[3,2-c]quinoline compound of the present invention had excellent cell permeability, compared with other commercially available dyes, and as shown in FIG. 24, particularly, the compound (IQ 16) of Formula 11 performed staining almost similar to DAPI and exhibited green, compared to DAPI exhibiting blue, so that it is expected to be less damaging to cells. In addition, it was confirmed that the compounds (IQ 6 and 36) of Formula 2 and Formula 12 below show an aspect similar to RNA select for staining RNA, and among these, the compound of Formula 12 works as a complementary stain with respect to DAPI known to stain the nucleus.

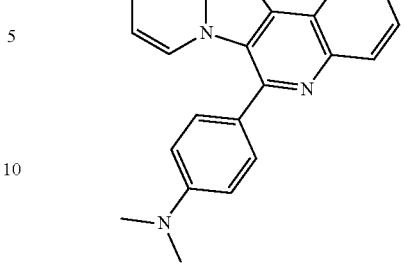

[FORMULA 12]

In addition, as shown in FIGS. 25A and 25B, it was confirmed that the compound (IQ 18) of Formula 8 has a Pearson's coefficient of 0.8 or more through a co-localization experiment with MitoTracker (FIG. 25A), and thus it can be seen that the compound of Formula 8 selectively stains the mitochondria. In addition, it can be confirmed that the compound of Formula 8 shows an aspect of increasing fluorescence by receiving light, and the compound (IQ 53) of Formula 15 having a furan group shows a similar tendency (FIG. 25B).

In addition, according to a co-localization experiment for the compound (IQ-B19) of Formula 27 with LysoTracker, it was confirmed that the compound of Formula 27 may be selectively present in the lysosome (FIG. 25C).

Example 10: Comparison of Fluorescence Stability with Conventionally-Developed Dyes Through a comparative experiment between the indolizino[3,2-c]quinoline compound of the present invention and other commercially available dyes, it was confirmed that the indolizino[3,2-c]quinoline compound of the present invention has excellent fluorescence stability, compared to Sytoselect or MitoTracker, and as shown in FIG. 26, particularly, the compound (IQ 36) of Formula 12 stains RNA in a pattern similar to the now currently available Sytoselect (RNA marker), and has superior stability, compared to Sytoselect. In addition, it was quantitatively identified that fluorescence is increased by irradiating the compound (IQ 18) of Formula 8 with light as described above.

Example 11: Confirmation of Cytotoxicity

As a candidate material applicable to a fluorescent probe, an experiment for the indolizino[3,2-c]quinoline compound was carried out to confirm a cytotoxic effect.

After $1 \times 10^4$ cells per well were seeded in a 96-well, the cells were incubated in a 37° C. incubator for 24 hours. Afterward, the indolizino[3,2-c]quinoline compound was treated at various concentrations (0.5, 1, 2, 5 and 10 μM), and cultured for 24 hours. After culture, the medium was replaced with 100 μl of a fresh medium, and 20 μl of an MTT reagent (5 mg/ml in DPBS) was added, and cultured for 3 hours. Finally, formazin was dissolved in DMSO, and absorbance was analyzed at 570 nm to examine an inhibitory effect of the drug on cell proliferation. As a control, 0.1% DMSO was used.

As a result, as shown in FIG. 27A, the compounds of the present invention did not show cytotoxicity even when treating A549 cells at a concentration of 10 μM or less for 24 hours, and as shown in FIG. 27B, the compounds of the present invention did not show cytotoxicity even when treating MCF7 cells at a concentration of 10 μM or less for 24 hours. Therefore, it was confirmed that the compounds of the present invention can be used as fluorescent materials suitable to be used in cell imaging.

It should be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

INDUSTRIAL APPLICABILITY

An indolizino[3,2-c]quinoline compound used in a fluorescent probe of the present invention is a water-soluble fluorescent compound whose fluorescence characteristics and application range vary greatly depending on the characteristics and position of a functional group binding to a hetero ring, can improve the shortcomings of a conventional organic fluorophore, and thus can be applied in various fields.

In addition, the fluorescent probe of the present invention binds to a nucleic acid or protein, so that it can be applied to various nucleic acid/protein function studies on its movement, drug-protein interaction, etc., and imaging technologies.

In addition, the fluorescent probe of the present invention can minimize self-quenching due to a large difference between an excitation wavelength and a fluorescence wavelength (Stokes shift).

In addition, since the fluorescent probe of the present invention has a different wavelength range of fluorescence and sensitivity to a surrounding environment depending on a substituent, it can be controlled to maximize fluorescence in an organic solvent and exhibit strong fluorescence in an aqueous solution (solvatochromic).

In addition, the fluorescent probe of the present invention can exhibit high fluorescence even in water or a buffer, have high solubility, and minimize a problem causing the aggregation of a protein.

In addition, the fluorescent probe of the present invention has excellent intracellular permeability, and is useful for imaging technologies in cells or tissue, and analysis of enzyme activity in cells.

The invention claimed is:

1. A fluorescent probe composition, comprising an indolizino[3,2-c]quinoline compound represented by Formula 1:

[Formula 1]

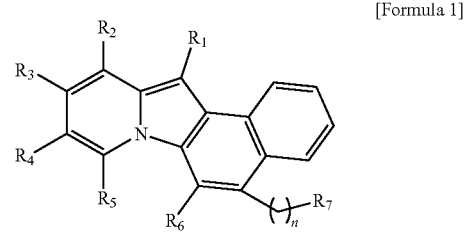

In Formula 1, $R_1$, $R_4$ and $R_5$ are each independently selected from the group consisting of hydrogen, halogen, $C_{1-12}$ alkyl, $C_{1-12}$ alkoxy group, $COOR_8$, substituted or unsubstituted $C_{6-20}$ aryl, substituted or unsubstituted $C_{2-20}$ heteroaryl,

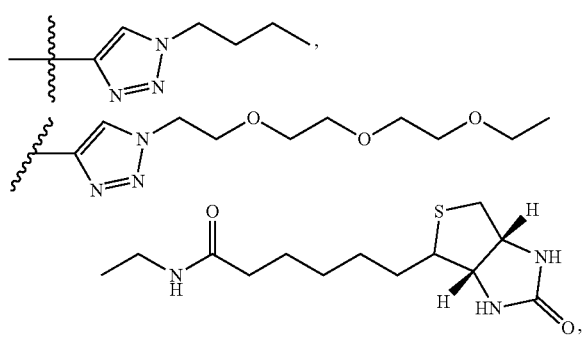

$C_{2-12}$ alkynyl, substituted $C_{2-12}$ alkenyl, amine, hydroxyl, aldehyde, nitrile, amide, phenoxy and boronic ester, $R_2$ and $R_3$ are bound with each other to form an aromatic ring, or each independently selected from the group consisting of hydrogen, halogen, $C_{1-12}$ alkyl, $C_{1-12}$ alkoxy, $COOR_8$, substituted or unsubstituted $C_{6-20}$ aryl, substituted or unsubstituted $C_{2-20}$ heteroaryl,

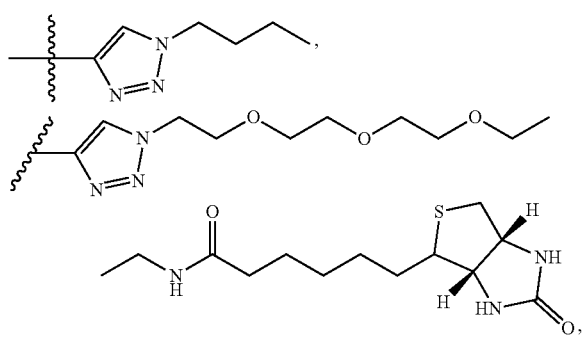

$C_{2-12}$ alkynyl, substituted $C_{2-12}$ alkenyl, amine, hydroxyl, aldehyde, nitrile, amide, phenoxy and boronic ester, $R_6$ is selected from the group consisting of $C_{1-12}$ alkyl, substituted $C_{2-12}$ alkenyl,

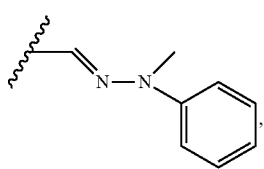 [SMILES: */C=N/N(C)c1ccccc1]

substituted or unsubstituted $C_{6-20}$ aryl, and substituted or unsubstituted $C_{2-20}$ heteroaryl, n is 0, 1, 2 or 3, $R_7$ is selected from the group consisting of hydrogen, hydroxyl, halogen and $C_{1-12}$ alkyl, and $R_8$ is selected from the group consisting of hydrogen, $C_{1-12}$ alkyl and $C_{2-12}$ alkynyl.

2. The composition of claim 1, wherein $R_1$, $R_4$ and $R_5$ are each independently selected from the group consisting of hydrogen, $C_{1-12}$ alkyl, $COOR_8$, and an amine, $R_2$ and $R_3$ are bound with each other to form an aromatic ring, or each independently selected from the group consisting of hydrogen, aldehyde, $C_{1-12}$ alkyl, substituted $C_{2-12}$ alkenyl, substituted or unsubstituted $C_{6-20}$ aryl, substituted or unsubstituted $C_{2-20}$ heteroaryl and a nitrile, $R_6$ is selected from the group consisting of $C_{1-12}$ alkyl, substituted $C_{2-12}$ alkenyl, substituted or unsubstituted $C_{6-20}$ aryl, and substituted or unsubstituted $C_{2-20}$ heteroaryl, n is 0, 1, 2 or 3, $R_7$ is selected from the group consisting of hydrogen, hydroxyl, halogen and $C_{1-6}$ alkyl, and $R_8$ is selected from the group consisting of hydrogen, $C_{1-12}$ alkyl and $C_{2-12}$ alkynyl.

3. The composition of claim 2, wherein the substituted $C_{2-12}$ alkenyl is linked to a substituent selected from the group consisting of aldehyde, substituted or unsubstituted $C_{6-20}$ aryl, substituted or unsubstituted $C_{2-20}$ heteroaryl, and nitrile.

4. The composition of claim 2, wherein the substituted $C_{6-20}$ aryl and substituted $C_{2-20}$ heteroaryl are prepared by linking one to three arbitrary carbon atoms each independently to a substituent selected from the group consisting of hydrogen, amine, hydroxyl, aldehyde, halogen, nitro, $C_{2-6}$ alkylester,

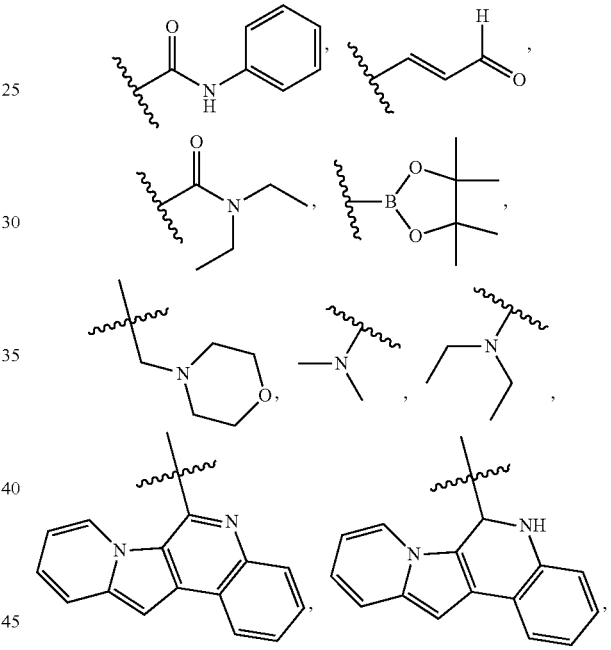

$CF_3$, COO—, $C_{1-6}$ alkyl and $C_{1-6}$ alkoxy.

5. The composition of claim 1, wherein the substituted $C_{2-12}$ alkenyl is linked to a substituent selected from the group consisting of aldehyde, substituted or unsubstituted $C_{6-20}$ aryl, substituted or unsubstituted $C_{2-20}$ heteroaryl, and nitrile.

6. The composition of claim 1, wherein the substituted $C_{6-20}$ aryl and substituted $C_{2-20}$ heteroaryl are prepared by linking one to three arbitrary carbon atoms each independently to a substituent selected from the group consisting of hydrogen, amine, hydroxyl, aldehyde, halogen, nitro, $C_{2-6}$ alkylester,

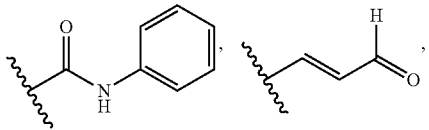

-continued

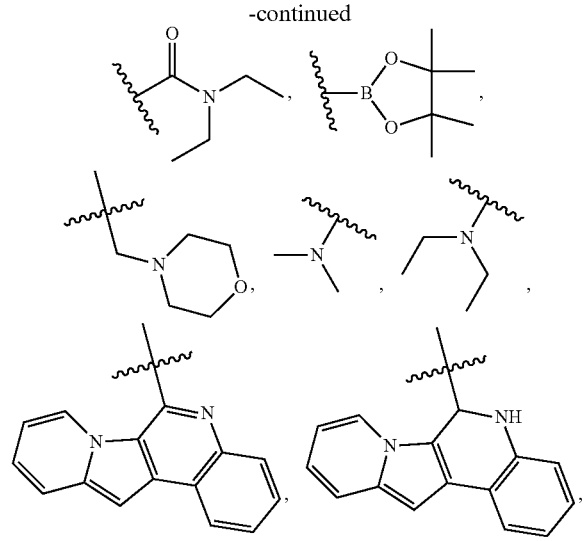

CF$_3$, COO—, C$_{1-6}$ alkyl and C$_{1-6}$ alkoxy.

7. The composition of claim 1, wherein the C$_{6-20}$ aryl is selected from the group consisting of phenyl, naphthyl, anthryl and biaryl.

8. The composition of claim 1, wherein the C$_{2-20}$ heteroaryl is selected from the group consisting of pyridyl, pyrimidyl, thiophenyl, pyrrolyl, furanyl, sulforanyl, morpholinyl, and triazolyl.

9. The composition of claim 1, wherein R$_1$ is selected from the group consisting of hydrogen, amine and COOR$_8$, R$_6$ is substituted or unsubstituted C$_{6-20}$ aryl or substituted or unsubstituted C$_{2-20}$ heteroaryl, and R$_8$ is hydrogen, C$_{1-12}$ alkyl or C$_{2-12}$ alkynyl.

10. A nucleic acid-, protein- or cell-detecting reagent, comprising the composition of claim 1.

11. A nucleic acid-, protein- or cell-imaging method using the composition of claim 1.

12. A fluorescent probe composition, comprising a compound selected from the group consisting of the following compounds:
  6-(4-Methoxyphenyl)indolizino[3,2-c]quinoline (Formula 2:IQ 6);
  6-(Naphthalen-1-yl)indolizino[3,2-c]quinoline (Formula 3:IQ 9);
  Methyl 6-(1H-pyrrol-2-yl)indolizino[3,2-c]quinoline-12-carboxylate (Formula 4:IQ 21);
  Ethyl 6-(3-fluorophenyl)indolizino[3,2-c]quinoline-12-carboxylate (Formula 5:IQ 28);
  Ethyl 6-(3,4-dimethoxyphenyl)indolizino[3,2-c]quinoline-12-carboxylate (Formula 6:IQ 30);
  11-Methyl-6-(p-tolyl)indolizino[3,2-c]quinoline (Formula 7:IQ 15);
  6-(Furan-2-yl)-11-methylindolizino[3,2-c]quinoline (Formula 8:IQ 18);
  6-(3,5-Dimethoxyphenyl)indolizino[3,2-c]quinoline (Formula 9:IQ 7);
  6-(3,4-Dimethoxyphenyl)-11-methylindolizino[3,2-c]quinoline (Formula 10:IQ 17);
  6-(3,5-Dimethoxyphenyl)-11-methylindolizino[3,2-c]quinoline (Formula 11:IQ 16);
  4-(Indolizino[3,2-c]quinolin-6-yl)-N,N-dimethylaniline (Formula 12:IQ 36);
  6-(p-Tolyl)indolizino[3,2-c]quinoline (Formula 13:IQ 3);
  11-methyl-6-(thiophen-2-yl)indolizino[3,2-c]quinoline (Formula 14:IQ 52);
  6-(5-chlorofuran-2-yl)-11-methylindolizino[3,2-c]quinoline (Formula 15:IQ 53);
  12-ethynyl-6-(4-methoxyphenyl)indolizino[3,2-c]quinoline (Formula 16:IQ 55);
  4-(5-(indolizino[3,2-c]quinolin-6-yl)-2-methoxybenzyl)morpholine (Formula 17:IQ 56);
  ethyl 6-(4-methoxy-3-(morpholinomethyl)phenyl)indolizino[3,2-c]quinoline-12-carboxylate (Formula 18:IQ 57);
  2,6-bis(indolizino[3,2-c]quinolin-6-yl)pyridine (Formula 19:IQ 5-D);
  6-(4-methoxyphenyl)-5-methylindolizino[3,2-c]quinolin-5-ium methyl sulfate (Formula 20:IQ 6-S1-Me);
  5-(2-chloroethyl)-6-(4-methoxyphenyl)indolizino[3,2-c]quinolin-5-ium trifluoromethanesulfonate (Formula 21:IQ 6-S2-Cl);
  6-(4-methoxyphenyl)indolizino[3,2-c]quinoline-10-carbonitrile (Formula 22:IQ 67);
  6-(4-methoxyphenyl)benzo[7,8]indolizino[3,2-c]quinoline (Formula 23:IQ 77);
  6-ethylbenzo[7,8]indolizino[3,2-c]quinoline (Formula 24:IQ 79);
  4-(indolizino[3,2-c]quinolin-6-yl)aniline (Formula 25:IQ-B1);
  4-(indolizino[3,2-c]quinolin-6-yl)phenol (Formula 26:IQ-B2);
  (E)-6-(4-methoxyphenyl)-10-styrylindolizino[3,2-c]quinoline (Formula 27:IQ-B19);
  (E)-10-(2-(1H-imidazol-1-yl)vinyl)-6-(4-methoxyphenyl)indolizino[3,2-c]quinoline (Formula 28:IQ-B20);
  4-(6-(4-methoxyphenyl)indolizino[3,2-c]quinolin-10-yl)benzaldehyde (Formula 29:IQ-B23);
  (E)-3-(6-(4-methoxyphenyl)indolizino[3,2-c]quinolin-10-yl)acrylaldehyde (Formula 30:IQ-B25);
  6-(4-methoxyphenyl)indolizino[3,2-c]quinoline-10-carbaldehyde (Formula 31:IQ-B11);
  (E)-6-(4-methoxystyryl)indolizino[3,2-c]quinoline (Formula 32:IQ-B12) 6,10-bis(4-methoxyphenyl)indolizino[3,2-c]quinoline (Formula 33:IQ-B26);
  (E)-3-(4-(6-(4-methoxyphenyl)indolizino[3,2-c]quinolin-10-yl)phenyl)acrylaldehyde (Formula 34:IQ-B31);
  4-(6-(4-methoxyphenyl)indolizino[3,2-c]quinolin-10-yl)-N,N-dimethylaniline (Formula 35:IQ-B37);
  4-(6-(4-methoxyphenyl)indolizino[3,2-c]quinolin-10-yl)-N-phenylbenzamide (Formula 36:IQ-B35); and
  N,N-diethyl-4-(6-(4-methoxyphenyl)indolizino[3,2-c]quinolin-10-yl)benzamide (Formula 37:IQ-B36).

13. An indolizino[3,2-c]quinoline compound represented by Formula 38:

[Formula 38]

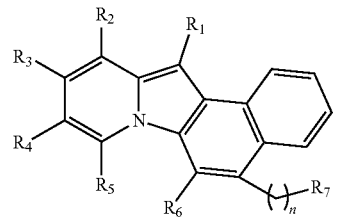

In Formula 38,
R$_1$ is hydrogen, C$_{2-12}$ alkynyl or amine,
R$_2$ and R$_3$ are bound with each other to form an aromatic ring, or each independently selected from the group consisting of hydrogen, substituted C$_{6-20}$ aryl, substituted $C_{2-12}$ alkenyl, amine, hydroxyl, aldehyde, nitrile, amide, phenoxy and boronic ester, $R_4$, $R_5$, and $R_7$ are each independently hydrogen, $R_6$ is selected from the group consisting of $C_{1-12}$ alkyl, substituted $C_{2-12}$ alkenyl,

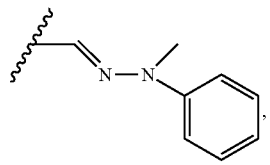 [SMILES: */C=N/N(C)c1ccccc1]

and substituted $C_{6-20}$ aryl, and n is 0, 1, 2 or 3, the substituted $C_{2-12}$ alkenyl is linked to a substituent selected from the group consisting of aldehyde, substituted or unsubstituted $C_{6-20}$ aryl, substituted or unsubstituted $C_{2-20}$ heteroaryl and nitrile, and the substituted or unsubstituted $C_{6-20}$ aryl and substituted $C_{2-20}$ heteroaryl are prepared by linking one to three arbitrary carbon atoms each independently to a substituent selected from the group consisting of hydrogen, amine, hydroxyl, aldehyde, halogen, nitro, $C_{2-6}$ alkylester,

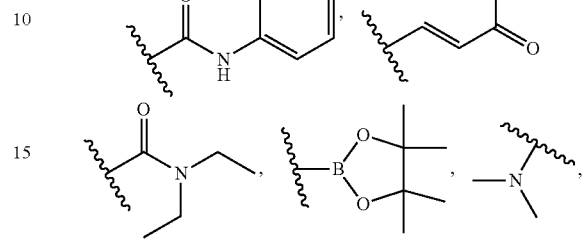

and $C_{1-6}$ alkoxy.

* * * * *

SEQUENCE LISTING

```
<160> NUMBER OF SEQ ID NOS: 2

<210> SEQ ID NO 1
<211> LENGTH: 48
<212> TYPE: DNA
<213> ORGANISM: Artificial Sequence
<220> FEATURE:
<223> OTHER INFORMATION: tetO1

<400> SEQUENCE: 1 cctaattttgttgacactctatcattgatagagttattttaccactc        48

<210> SEQ ID NO 2
<211> LENGTH: 48
<212> TYPE: DNA
<213> ORGANISM: Artificial Sequence
<220> FEATURE:
<223> OTHER INFORMATION: tetO2

<400> SEQUENCE: 2 gagtggtaaaataactctatcaatgatagagtgtcaacaaaaattagg        48
```